US012678456B1

(12) United States Patent
Lai et al.

(10) Patent No.: US 12,678,456 B1
(45) Date of Patent: Jul. 14, 2026

(54) PHOTOTHERMAL-RESPONSIVE INJECTABLE HYDROGEL FOR WOUND HEALING, HEALING, ANTIBACTERIAL AND OTHER BIOMEDICAL APPLICATIONS

(71) Applicants: Cheng-Yu Lai, Miami, FL (US); Daniela Rodica Radu, Miami, FL (US)

(72) Inventors: Cheng-Yu Lai, Miami, FL (US); Daniela Rodica Radu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 19/354,072

(22) Filed: Oct. 9, 2025

(51) Int. Cl.

| | |
|---|---|
| ***A61K 33/24*** | (2019.01) |
| ***A61K 9/06*** | (2006.01) |
| ***A61K 41/00*** | (2020.01) |
| ***A61P 31/04*** | (2006.01) |
| ***A61P 31/10*** | (2006.01) |
| ***C01G 47/00*** | (2006.01) |

(52) U.S. Cl.
CPC ................ *A61K 33/24* (2013.01); *A61K 9/06* (2013.01); *A61K 41/0057* (2013.01); *A61P 31/04* (2018.01); *A61P 31/10* (2018.01); *C01G 47/006* (2013.01); *C01P 2002/72* (2013.01); *C01P 2002/82* (2013.01); *C01P 2002/85* (2013.01); *C01P 2004/03* (2013.01); *C01P 2004/04* (2013.01)

(58) Field of Classification Search
CPC ...... A61K 33/24; A61K 9/06; A61K 41/0057; A61P 31/04; A61P 31/10; C01G 47/006; C01P 2002/72; C01P 2002/82; C01P 2002/85; C01P 2004/03; C01P 2004/04
See application file for complete search history.

(56) References Cited

FOREIGN PATENT DOCUMENTS

CN 117383619 A * 1/2024 ............. H10F 30/28

OTHER PUBLICATIONS

Machine translation for CN117383619A (46-pg. pdf). Published Jan. 12, 2024.*

* cited by examiner

*Primary Examiner* — Jeffrey T. Palenik
(74) *Attorney, Agent, or Firm* — SALIWANCHIK, LLOYD & EISENSCHENK

(57) ABSTRACT

The subject invention provides a novel class of mixed-metal chalcogenide compounds exhibiting POD-like catalytic activity, efficient photothermal conversion under NIR irradiation, and broad-spectrum antimicrobial properties. The invention further provides hydrogel formulations incorporating these compounds in a polymeric matrix, as well as their use in a range of biomedical applications, such as treating infected wounds, preventing surgical site infections, and delivering localized, non-antibiotic antimicrobial therapy.

13 Claims, 47 Drawing Sheets

1 Å = 0.1 nm

PHOTOTHERMAL-RESPONSIVE INJECTABLE HYDROGEL FOR WOUND HEALING, HEALING, ANTIBACTERIAL AND OTHER BIOMEDICAL APPLICATIONS

GOVERNMENT SUPPORT

This invention was made with government support under 2122078 awarded by the National Science Foundation. The government has certain rights in the invention.

BACKGROUND OF THE INVENTION

The skin is a natural protective barrier, shielding internal organs from direct exposure to external environmental factors and preventing dehydration. Skin damage compromises this protective function, exposing the body to potential microbial invasion. Microorganisms can colonize the wound site, resulting in infections that delay healing and, in extreme cases, lead to life-threatening complications.

Fungal infections represent a significant global public health challenge, causing over 1.5 million deaths annually and affecting more than one billion individuals worldwide. For example, overproduction of *Candida albicans* (*C. albicans*), a commensal fungus typically residing in small amounts on the skin, can lead to a wide range of infections. The persistent and escalating use of antibiotics has contributed to the emergence of multidrug-resistant pathogens, reducing the effectiveness of conventional antifungal therapies.

Nanomaterials have attracted growing interest for their potential use as antimicrobial agents. Among these, nanozymes—nanomaterials with enzyme-like behavior in biological systems—present an alternative to traditional enzymes and have emerged as a promising class of antimicrobial agents due to their broad-spectrum activity and negligible biotoxicity profiles.

Peroxidases (also known as peroxide reductases) belong to a large group of enzymes that catalyze the oxidation of a substrate by hydrogen peroxide ($H_2O_2$). The hydrogen peroxide is converted into water ($H_2O$) while oxidizing its substrate to the corresponding oxide form. Among various nanozymes, those mimicking peroxidase (POD) activity, known as POD nanozymes, are particularly of interest due to their impressive broad-spectrum antimicrobial properties, low biological toxicity, low risk of inducing multidrug resistance, and unique mechanisms of sterilization.

The wound healing process comprises a series of interdependent physiological events that can include, for example, homeostasis, inflammation, proliferation, and maturation. Homeostasis occurs in the event of a wound injury and involves the formation of blood clots with platelets to stop the bleeding. The inflammatory phase often lasts from three to twenty days, providing a new framework for blood vessels and cell growth. Inflammatory cells debride injured tissue through increased blood circulation within hours of the occurrence of the injury. The proliferation phase usually lasts from one to six weeks, during which granulation tissue is formed with cells migrating at the wound edges to contract the skin around the damaged area. This allows complete healing with the restoration of underlying tissue.

Excessive dehydration at the wound site disrupts the optimal moist environment required for effective healing, further prolonging recovery. Traditional dry dressings, such as cotton wool, bandages, and gauze, initially support wound management but cannot maintain necessary moisture levels. Furthermore, their tendency to adhere to the wound surface can cause trauma upon removal.

Advanced functional wet dressings have emerged to address these limitations. Hydrogels, characterized by their three-dimensional cross-linked structures and hydrophilic polymer networks, have been widely developed for use as wound dressings. These materials provide significant advantages: maintaining moisture, facilitating gas exchange, acting as microbial barriers, and absorbing excess exudate. Hydrogels demonstrate excellent biocompatibility, accelerate wound healing, and enable minimally traumatic removal. Beyond wound care, hydrogels have garnered significant attention in biomedical research for applications such as drug delivery, tissue engineering, biosensors, and antitumor and antibacterial therapies.

Stimuli-responsive hydrogels are smart materials capable of dynamically changing their physical properties (e.g., phase or volume) when exposed to specific external triggers. These stimuli can be physical (e.g., temperature, light, or magnetic fields) or chemical (e.g., pH or ionic strength), making them highly versatile for applications such as controlled drug delivery, responsive biosensors, and adaptive tissue scaffolds.

In recent years, hydrogels have been engineered to encapsulate antibiotics for preventing and treating bacterial infections; however, antibiotic overuse can lead to bacterial resistance. Photothermal therapy emerged as an alternative approach, demonstrating efficacy in treating malignant tumors and bacterial infections.

Despite advancements in these areas, there remains a critical need for novel antimicrobial agents that can serve as effective alternatives to traditional antibiotics for the treatment of microbial infections and improved wound healing. In addition, the development of robust strategies for integrating these agents into diverse platforms, including multifunctional compositions, is essential to expand their applicability across a wide range of biomedical applications.

BRIEF SUMMARY OF THE INVENTION

The subject invention provides a novel class of mixed-metal chalcogenide compounds exhibiting peroxidase-like (POD-like) catalytic activity, efficient photothermal conversion under NIR irradiation, and broad-spectrum antimicrobial properties. These compounds are incorporated into a biocompatible, thermoresponsive hydrogel that enables injectability, undergoes sol-gel transition at physiological temperature, and forms a conformal barrier over target sites, resulting in multifunctional compositions.

Advantageously, these compositions or hydrogel formulations can be used in various biomedical applications, including, for example, treating infected wounds, preventing surgical site infections, and delivering localized antimicrobial therapy. In preferred embodiments, the compounds, hydrogels, and compositions provided by the subject invention offer other advantages, including, for example, reducing dependence on conventional antibiotics, promoting faster and more effective healing through photothermal-assisted antimicrobial action, and conforming to irregular wound geometries to ensure targeted, localized treatment and improved therapeutic outcomes.

In certain embodiments, the subject invention provides a mixed-metal chalcogenide having a general formula of $M_xM'_{1-x}X_y$, wherein M and M' are distinct transition metal elements, preferably, each independently selected from the group consisting of Molybdenum (Mo), Tungsten (W), Rhenium (Re), Niobium (Nb), Tantalum (Ta), Vanadium (V), Titanium (Ti), Zirconium (Zr), and Hafnium (Hf); and X is a chalcogen element, preferably, selected from the group consisting of, for example, Oxygen (O), Sulfur(S), Selenium (Se), and Tellurium (Te); and wherein 0≤x≤1 and 1≤y≤3. In specific embodiments, where 0<x<1 and 1.5≤y≤2.5.

In some embodiments, the mixed-metal chalcogenide of the subject invention has a formula of $M_xM'_{1-x}S_y$. In some embodiments, the mixed-metal chalcogenide of the subject invention has a formula of $M_xRe_{1-x}S_y$. In some embodiments, the mixed-metal chalcogenide of the subject invention has a formula of $Mo_xRe_{1-x}S_y$ or $W_xRe_{1-x}S_y$. In specific embodiments, the mixed-metal chalcogenide has a formula of $Mo_{0.42}Re_{0.58}S_{1.94}$, $Mo_{0.66}Re_{0.34}S_{1.85}$, or $Mo_{0.81}Re_{0.19}S_{1.76}$.

In certain embodiments, the subject invention provides a method of synthesizing the mixed-metal chalcogenide of the subject invention using a hydrothermal process, comprising reacting one or more metal precursors and one or more chalcogen precursors under a hydrothermal condition.

In certain embodiments, the subject invention provides a hydrogel or hydrogel formulation (hydrogel/hydrogel formulation) comprising: (i) a mixed-metal chalcogenide of the subject invention having a general formula of $M_xM'_{1-x}X_y$, wherein M and M' are distinct transition metal elements, and X is a chalcogen element; and wherein 0≤x≤1 and 1≤y≤3; (ii) a thermo-responsive polymer; and (iii) a matrix polymer.

In some embodiments, the hydrogel/hydrogel formulation of the subject invention comprises a mixed-metal chalcogenide selected from the group consisting of, for example, $MoS_2$, $ReS_2$, $TiSe_2$, $WS_2$, $Mo_{0.42}Re_{0.58}S_{1.94}$, $Mo_{0.66}Re_{0.34}S_{1.85}$, and $Mo_{0.81}Re_{0.19}S_{1.76}$, or any combination thereof.

In some embodiments, the thermo-responsive polymer is selected from the Pluronic family of block copolymers, preferably selected from the group consisting of PF127, PF68, and PF87, or any combination thereof. In specific embodiments, the relative mass ratio between the thermo-responsive polymer and the mixed-metal chalcogenide may be varied within a range of about 300:1 to about 2,000:1.

In some embodiments, the matrix polymer is selected from saccharide-based biopolymers, preferably selected from the group consisting of, for example, carboxymethyl chitosan (CMC), chitosan, gelatin, polyethylene glycol (PEG), hyaluronic acid, alginate, dextran, and derivatives thereof. In specific embodiments, the relative mass ratio between the matrix polymer and the mixed-metal chalcogenide may be varied within a range of about 10:1 to about 500:1.

In some embodiments, the matrix polymer is engineered to incorporate one or more functional additives selected from the group consisting of pharmaceutical agents, imaging agents, aesthetic or preservation agents, bioactive compounds, protective or stabilizing agents, genetic materials, and functional fillers.

In certain embodiments, the subject invention provides a method of preparing the hydrogel or hydrogel formulation of the subject invention, comprising incorporating the mixed-metal chalcogenide of the subject invention into a network of a thermo-responsive polymer mixed with a matrix polymer.

In certain embodiments, the subject invention provides a composition comprising the mixed-metal chalcogenide, or hydrogel/hydrogel formulation, and optionally, a pharmaceutically acceptable carrier.

In certain embodiments, the subject invention provides a composition comprising (i) a mixed-metal chalcogenide of the subject invention having a general formula of $M_xM'_{1-x}X_y$, wherein M and M' are distinct transition metal elements, and X is a chalcogen element; and wherein 0≤x≤1 and 1≤y≤3; (ii) a thermo-responsive polymer; and (iii) a matrix polymer.

In certain embodiments, the subject invention provides a method of inhibiting the growth and/or reproduction of microbial pathogens, and/or killing microbial pathogens in a cell, tissue, or organism, the method comprising administering to the cell, tissue, or organism an effective amount of the mixed-metal chalcogenide, the hydrogel/hydrogel formulation, or the composition of the subject invention. In some embodiments, the microbial pathogens are selected from fungal pathogens, and bacterial pathogens.

In certain embodiments, the subject invention provides a method of treating a microbial infection in a subject in need thereof, the method comprising administering to the subject an effective amount of the mixed-metal chalcogenide, the hydrogel/hydrogel formulation, or the composition of the subject invention. In some embodiments, the microbial infection is caused by a fungus or bacterium.

In certain embodiments, the subject invention provides a method of managing a wound in a subject, comprising administering to the wound an effective amount of the mixed-metal chalcogenide, the hydrogel/hydrogel formulation, or the composition of the subject invention.

In some embodiments, the wound is associated, or not associated, with at least one of microbial infection, delayed healing, and impaired tissue regeneration.

DETAILED DESCRIPTION OF THE INVENTION

Figure 1:
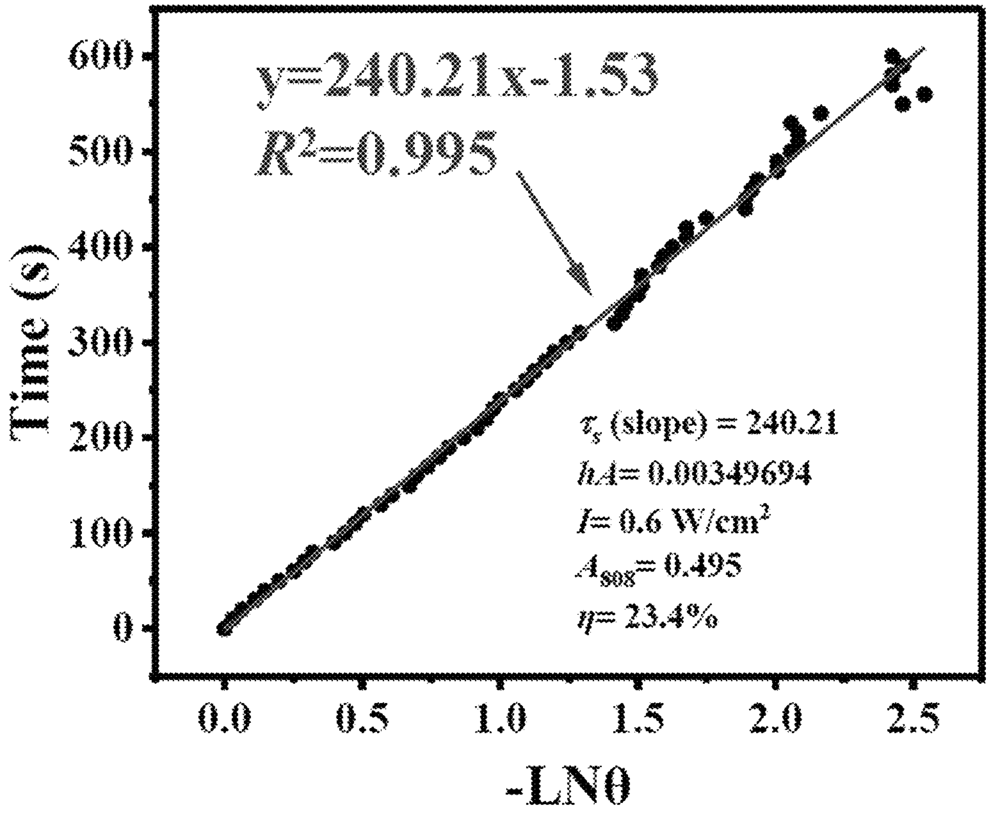
FIG. 1 shows calculation of the photothermal conversion efficiency (η) for the PF127/CMC/$Mo_{0.66}Re_{0.34}S_{1.85}$ hydrogel.

The subject invention provides compounds, compositions and methods for preventing or treating infections, promoting tissue regeneration and/or improving wound healing. In one embodiment, the subject invention provides effective wound care materials that prevent or treat infections, maintain optimal moisture levels and support tissue regeneration.

In one embodiment, the subject invention provides an injectable, thermoresponsive hydrogel that comprises one or more nanozymes or photothermal agents incorporated within a mixture of polymers, wherein at least one of the polymers is a thermoresponsive polymer and/or a matrix polymer.

Advantageously, the hydrogel of the subject invention offers a combination of antibacterial activity, thermo-responsiveness, dynamic mechanical properties, and biocompatibility, all contributing to improved wound healing outcomes. The thermo-responsiveness of such hydrogel pertains to the polymer property that allows the conversion of the hydrogel from liquid in ambient temperature to solid hydrogel when reaching a desired temperature, for example, body temperature. The shear-thinning properties support injectability. Thus, the photothermal-responsive injectable hydrogel of the subject invention can be used for advanced wound management, providing both antibacterial protection and photothermal-assisted healing.

In one embodiment, the nanozyme/photothermal agent comprises a mixed-metal chalcogenide compound. In specific embodiments, the mixed-metal chalcogenide compound exhibits peroxidase-like catalytic activity, efficient photothermal conversion under NIR irradiation, and broad-spectrum antimicrobial properties. These characteristics make the mixed-metal chalcogenide compounds particularly effective for infection control without the need for conventional antibiotics.

In one embodiment, the subject invention provides a multifunctional composition comprising a thermoresponsive hydrogel incorporating the mixed-metal chalcogenide as a photothermal and antimicrobial agent. The hydrogel is formulated with biocompatible polymers that collectively confer injectability, temperature-responsive sol-gel transition, moisture retention, and mechanical integrity. This enables the composition to be administered as a liquid at room temperature and to rapidly solidify into a conformal gel at physiological temperature, forming a protective and functional barrier at a target site, such as a wound.

In yet another aspect, the subject invention provides methods of using the mixed-metal chalcogenide compounds, or compositions comprising them, in various biomedical applications, including antimicrobial treatments, infection prevention, and wound care management.

Mixed-Metal Chalcogenides

The subject invention provides mixed-metal chalcogenide compounds that function as nanozymes exhibiting, for example, POD-like catalytic activity. These compounds demonstrate both potent antimicrobial effects and photothermal properties, offering a synergistic approach for the treatment of microbial infections, including, for example, bacterial and fungal infections.

In one embodiment, the subject invention provides a mixed-metal chalcogenide having a general formula of $M_xM'_{1-x}X_y$, wherein M and M' are distinct transition metal elements, and X is a chalcogen element; and wherein 0≤x≤1 and 1≤y≤3, preferably, 1.5≤y≤2.5, more preferably, 1≤y≤2.

In certain embodiments, M and M' are each independently selected from the group consisting of Molybdenum (Mo), Tungsten (W), Rhenium (Re), Niobium (Nb), Tantalum (Ta), Vanadium (V), Titanium (Ti), Zirconium (Zr), and Hafnium (Hf). In certain embodiments, X is a chalcogen element selected from the group consisting of Oxygen (O), Sulfur(S), Selenium (Se), and Tellurium (Te).

In certain embodiments, the mixed-metal chalcogenide has x being 0 or 1, resulting in a binary metal chalcogenide comprising a single transition metal element and a single chalcogen element. Examples of suitable binary metal chalcogenides include, but are not limited to, $MoS_2$, $ReS_2$, $TiSe_2$, and $WS_2$. In certain embodiments, the mixed-metal chalcogenide compound defines a ternary metal chalcogenide comprising two distinct transition metal elements and one chalcogen element when 0<x<1.

In certain embodiments, the value of y can be from about 1 to about 3. For example, y may fall within any of the following sub-ranges: 1.5≤y≤2.5, 1.5≤y≤2.4, 1.5≤y≤2.3, 1.5≤y≤2.2, 1.5≤y≤2.1, 1.6≤y≤2.5, 1.6≤y≤2.4, 1.6≤y≤2.3, 1.6≤y≤2.2, or 1.6≤y≤2.1. In some embodiments, y can be no greater than 2 and may, for example, fall within any of the following sub-ranges: 1.5≤y≤2, 1.6≤y≤2, 1.7≤y≤2, 1.8≤y≤2, 1.9≤y≤2, 1.5≤y≤1.9, 1.6≤y≤1.9, 1.7≤y≤1.9, 1.8≤y≤1.9, 1.5≤y≤1.8, 1.6≤y≤1.8, or 1.7≤y≤1.8. In some embodiments, y can be greater than 2 and may, for example, fall within any of the following sub-ranges: 2<y≤2.5, 2<y≤2.4, 2<y≤2.3, 2<y≤2.2, 2<y≤2.1, 2.1≤y≤2.3, 2.1<y≤2.2, or 2.2≤y≤2.3. In some embodiments, the value of y is no less than 1.6, 1.7, or 1.8. In some embodiments, the value of y is no greater than 2.3, 2.2, or 2.1.

Advantageously, the mixed-metal chalcogenide of the subject invention exhibits a range of desirable properties, including a large surface area and semiconducting characteristics such as tunable band gaps. In addition, it may possess peroxidase-like catalytic activity and demonstrate favorable biocompatibility, supporting its potential as an alternative to traditional antibiotics. These features make it suitable for various biomedical applications, including bactericidal treatment and photothermal therapy (PTT).

In certain embodiments, the mixed-metal chalcogenide of the subject invention has a formula of $M_xM'_{1-x}S_y$, wherein M and M' are distinct transition metal elements, each independently selected from the group consisting of Mo, W, Re, Nb, Ta, V, Ti, Zr, and Hf; and wherein 0≤x≤1 and 1≤y≤3. In specific embodiments, 0<x<1, and y can be no greater than 2 and may, for example, fall within any of the following sub-ranges: 1.5≤y≤2, 1.6≤y≤2, 1.7≤y≤2, 1.8≤y≤2, 1.9≤y≤2, 1.5≤y≤1.9, 1.6≤y≤1.9, 1.7≤y≤1.9, 1.8≤y≤1.9, 1.5≤y≤1.8, 1.6≤y≤1.8, or 1.7≤y≤1.8.

In certain embodiments, the mixed-metal chalcogenide of the subject invention has a formula of $M_xRe_{1-x}S_y$, wherein M is a transition metal element selected from the group consisting of Mo, W, Re, Nb, Ta, V, Ti, Zr, and Hf; and wherein 0≤x≤1, and 1.5≤y≤2.5. In specific embodiments, 0<x<1, and y can be no greater than 2 and may, for example, fall within any of the following sub-ranges: 1.5≤y≤2, 1.6≤y≤2, 1.7≤y≤2, 1.8≤y≤2, 1.9≤y≤2, 1.5≤y≤1.9, 1.6≤y≤1.9, 1.7≤y≤1.9, 1.8≤y≤1.9, 1.5≤y≤1.8, 1.6≤y≤1.8, or 1.7≤y≤1.8. In specific embodiments, x can be no less than 0.5 and may, for example, fall within any of the following sub-ranges: 0.5≤x<1, 0.6≤x<1, 0.7≤x<1, 0.8≤x<1, 0.9≤x<1, 0.5≤x≤0.9, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $M_xRe_{1-x}X_y$, wherein M is a transition metal element selected from the group consisting of Mo, W, Re, Nb, Ta, V, Ti, Zr, and Hf; X is a chalcogen element selected from the group consisting of O, S, Se, and Te; and wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x \leq 0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $Mo_xM'_{1-x}X_y$, wherein M' is a transition metal element selected from the group consisting of Mo, W, Re, Nb, Ta, V, Ti, Zr, and Hf; X is a chalcogen element selected from the group consisting of O, S, Se, and Te; and wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x \leq 0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $Mo_xM'_{1-x}S_y$, wherein M' is a transition metal element selected from the group consisting of Mo, W, Re, Nb, Ta, V, Ti, Zr, and Hf; and wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x \leq 0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $W_xM'_{1-x}X_y$, wherein M' is a transition metal element selected from the group consisting of Mo, W, Re, Nb, Ta, V, Ti, Zr, and Hf; X is a chalcogen element selected from the group consisting of O, S, Se, and Te; and wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x<0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $Mo_xRe_{1-x}X_y$, wherein X is a chalcogen element selected from the group consisting of O, S, Se, and Te; and wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x \leq 0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $Mo_xRe_{1-x}S_y$, wherein $0 \leq x \leq 1$, and $1 \leq y \leq 3$. In specific embodiments, $0<x<1$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$. In specific embodiments, x can be no less than 0.5 and may, for example, fall within any of the following sub-ranges: $0.5 \leq x<1$, $0.6 \leq x<1$, $0.7 \leq x<1$, $0.8 \leq x<1$, $0.9 \leq x<1$, $0.5 \leq x \leq 0.9$, $0.6 \leq x \leq 0.9$, $0.7 \leq x \leq 0.9$, $0.8 \leq x \leq 0.9$, $0.5 \leq x \leq 0.8$, $0.6 \leq x \leq 0.8$, $0.7 \leq x \leq 0.8$, $0.5 \leq x \leq 0.7$, $0.6 \leq x \leq 0.7$, or $0.5 \leq x \leq 0.6$.

In certain embodiments, the mixed-metal chalcogenide of the subject invention has a formula of $W_xRe_{1-x}S_y$, wherein $0 \leq x \leq 1$, and $1.5 \leq y \leq 2.5$. In specific embodiments, x can be no greater than 0.5 and may, for example, fall within any of the following sub-ranges: $0<x \leq 0.5$, $0<x \leq 0.4$, $0<x \leq 0.3$, $0<x \leq 0.2$, $0<x \leq 0.1$, $0.1 \leq x \leq 0.5$, $0.1 \leq x \leq 0.4$, $0.1 \leq x \leq 0.3$, $0.1 \leq x \leq 0.2$, $0.2 \leq x \leq 0.5$, $0.2 \leq x \leq 0.4$, $0.2 \leq x \leq 0.3$, $0.3 \leq x \leq 0.5$, $0.3 \leq x \leq 0.4$, or $0.4 \leq x \leq 0.5$, and y can be no greater than 2 and may, for example, fall within any of the following sub-ranges: $1.5 \leq y \leq 2$, $1.6 \leq y \leq 2$, $1.7 \leq y \leq 2$, $1.8 \leq y \leq 2$, $1.9 \leq y \leq 2$, $1.5 \leq y \leq 1.9$, $1.6 \leq y \leq 1.9$, $1.7 \leq y \leq 1.9$, $1.8 \leq y \leq 1.9$, $1.5 \leq y \leq 1.8$, $1.6 \leq y \leq 1.8$, or $1.7 \leq y \leq 1.8$.

In specific embodiments, the subject invention provides a mixed-metal chalcogenide having a formula of $Mo_{0.25}Re_{0.75}S_2$, $Mo_{0.5}Re_{0.5}S_2$, $Mo_{0.75}Re_{0.25}S_2$, $Mo_{0.42}Re_{0.58}S_{1.94}$, $Mo_{0.66}Re_{0.34}S_{1.85}$, or $Mo_{0.81}Re_{0.19}S_{1.76}$.

In certain embodiments, the mixed-metal chalcogenide has a metal-to-chalcogen molar ratio in a range from about 1:1 to 1:3, from about 1:1 to 1:2.9, from about 1:1 to 1:2.8, from about 1:1 to 1:2.7, from about 1:1 to 1:2.6, from about 1:1 to 1:2.5, from about 1:1 to 1:2.4, from about 1:1 to 1:2.3, from about 1:1 to 1:2.2, from about 1:1 to 1:2.1, from about 1:1 to 1:2, from about 1:1 to 1:1.95, from about 1:1 to 1:1.9, from about 1:1 to 1:1.85, from about 1:1 to 1:1.8, from about 1:1 to 1:1.75, from about 1:1 to 1:1.7, from about 1:1 to 1:1.65, from about 1:1 to 1:1.6, from about 1:1 to 1:1.55; from about 1:1 to 1:1.5, from about 1:1 to 1:1.45, from about 1:1 to 1:1.4, from about 1:1 to 1:1.35, or from about 1:1 to 1:1.3. In specific embodiments, the mixed-metal chalcogenide has a metal-to-chalcogen molar ratio about 1:2, about 1:1.94, about 1:1.85, or about 1:1.76.

In certain embodiments, the mixed-metal chalcogenide has a M-to-M' molar ratio in a range from about 0:1 to 1:0, from about 0.05:0.95 to 0.95:0.05, from about 0.1:0.9 to 0.9:0.1, from about 0.15:0.85 to 0.85:0.15, from about 0.2:0.8 to 0.8:0.2, from about 0.25:0.75 to 0.75:0.25, from about 0.3:0.7 to 0.7:0.3, from about 0.35:0.65 to 0.65:0.35, from about 0.4:0.6 to 0.6:0.4, or from 0.45:0.55 to 0.55:0.45. In some embodiments, the mixed-metal chalcogenide has a M-to-M' molar ratio selected from, for example, about 0:1, about 0.05:0.95, about 0.1:0.9, about 0.15:0.85, about 0.2:0.8, about 0.25:0.75, about 0.3:0.7, about 0.35:0.65, about 0.4:0.6, about 0.45:0.55, about 0.5:0.5, about 0.55:0.45, about 0.6:0.4, about 0.65:0.35, about 0.7:0.3, about 0.75:0.25, about 0.8:0.2, about 0.85:0.15, about 0.9:0.1, about 0.95:0.05, or about 1:0.

In certain embodiments, the specific stoichiometries of the mixed-metal chalcogenides may be selected or adjusted based on the desired balance of properties, such as photothermal conversion efficiency, peroxidase-like catalytic activity, dispersion stability, or biocompatibility. For example, a higher proportion of rhenium may enhance photothermal performance, while molybdenum-rich compositions may offer more favorable enzyme-mimetic and antimicrobial properties. Chalcogen stoichiometry (i.e., the value of y) may also be tuned to introduce vacancies or defects that enhance surface activity and reactivity in biological or photonic environments.

In certain embodiments, the mixed-metal chalcogenide of the subject invention has a two-dimensional (2D) nanostructure. Specifically, the mixed-metal chalcogenide exhibits a flower-like morphology composed of self-assembled nanosheets. The layered nanosheet structure provides a high surface area and a well-defined nanoscale architecture, which is advantageous for catalytic, electronic, or biomedical applications.

In certain embodiments, the mixed-metal chalcogenide of the subject invention having a general formula of $M_xM'_{1-x}X_y$ comprises uniformly distributed M, M', and X elements throughout the nanostructure.

In certain embodiments, the mixed-metal chalcogenide of the subject invention exhibits a crystalline structure. The incorporation of both metal species M and M' can result in subtle shifts in lattice parameters and vibrational modes, indicative of solid-solution formation and lattice modulation. These structural characteristics are tunable based on the selected composition.

In certain embodiments, the optical absorption properties of the mixed-metal chalcogenide can be adjusted based on the composition. Increasing the proportion of rhenium can lead to bandgap narrowing and a red shift in the absorption spectrum. Such tunable optoelectronic properties make these materials suitable for applications such as photothermal therapy, sensing, or energy harvesting.

In certain embodiments, the mixed-metal chalcogenide of the subject invention has a particle size in the nanometer range, for example, from about 50 nm to 500 nm, from about 60 nm to 450 nm, from about 70 nm to 400 nm, from about 80 nm to 350 nm, from about 80 nm to 300 nm, from about 90 nm to 250 nm, from about 90 nm to 200 nm, from about 100 nm to 200 nm, from about 100 nm and 300 nm, from about 150 nm to 300 nm, from about 200 nm to 300 nm, from about 50 nm to 150 nm, or from about 80 nm to 150 nm.

In certain embodiments, the 2D nanomaterial comprising the mixed-metal chalcogenide of the subject invention exhibits a negative surface charge, which contributes to dispersion stability and reduces the likelihood of disrupting healthy cell membranes. These properties enhance the suitability for therapeutic or antimicrobial applications.

Hydrogel Formulations and Compositions

In certain embodiments, the subject invention provides a hydrogel/hydrogel formulation comprising: (i) one or more nanozymes and/or photothermal agents, wherein at least one nanozyme and/or photothermal agent is a 2D nanomaterial comprising a mixed-metal chalcogenide of the subject invention having a general formula of $M_xM'_{1-x}X_y$, wherein M and M' are distinct transition metal elements, and X is a chalcogen element; and wherein $0 \le x \le 1$ and $1 \le y \le 3$; (ii) a thermo-responsive polymer; and (iii) a matrix polymer.

In certain embodiments, the 2D nanomaterial exhibits strong photothermal conversion efficiency, peroxidase-like catalytic activity, and broad-spectrum antimicrobial properties. In certain embodiments, the thermo-responsive polymer provides biocompatability and phase-change abilities. In certain embodiments, the matrix polymer provides water solubility, moisture retention, and additional antimicrobial activities.

Advantageously, in some embodiments, the hydrogel/hydrogel formulation of the subject invention demonstrates significant antibacterial efficacy along with remarkable photothermal responsiveness, and excellent cytocompatibility. The term "cytocompatibility" refers to the ability of a material or substance, e.g., the hydrogel/hydrogel formulation of the subject invention, to interact with cells without causing harmful effects. Also, the hydrogel/hydrogel formulation of the subject invention enhances cell migration and promotes tissue regeneration. Thus, the hydrogel/hydrogel formulation of the subject invention is a photothermal-responsive injectable hydrogel that can be used for advanced wound management, providing both antibacterial protection and photothermal-assisted healing.

In specific embodiments, the hydrogel/hydrogel formulation comprises one or more photothermal agents (e.g., gold nanoparticles, polydopamine, or graphene oxide) that convert NIR light into localized heat, enabling controlled release of encapsulated therapeutic agents and thermal eradication of microbes.

In certain embodiments, the subject invention provides an injectable hydrogel/hydrogel formulation comprising a 2D nanomaterial incorporated into a polymeric matrix, wherein the 2D nanomaterial comprises a mixed-metal chalcogenide of the subject invention having a general formula of $M_xM'_{1-x}X_y$, wherein M and M' are distinct transition metal elements, and X is a chalcogen element; and wherein $0 \le x \le 1$ and $1 \le y \le 3$; and wherein the polymeric matrix comprises at least a thermo-responsive polymer, and a matrix polymer.

In certain embodiments, the subject invention provides a hydrogel formulation in a liquid form. In certain embodiments, the subject invention provides a solid hydrogen comprising a 2D nanomaterial encapsulated in a polymeric matrix, wherein the 2D nanomaterial comprises a mixed-metal chalcogenide of the subject invention having a general formula of $M_xM'_{1-x}X_y$, wherein M and M' are distinct transition metal elements, and X is a chalcogen element; and wherein $0 \le x \le 1$, and $1 \le y \le 3$; and wherein the polymeric matrix comprises at least a thermo-responsive polymer and a matrix polymer in a cross-linked network.

In certain embodiments, the subject invention provides a solid hydrogel comprising a polymeric matrix that encapsulates mixed-metal chalcogenides of the subject invention, wherein the polymeric matrix comprises at least a thermo-responsive polymer and a matrix polymer in a cross-linked network.

In certain embodiments, the hydrogel/hydrogel formulation of the subject invention comprises any single mixed-metal chalcogenide described herein or a combination of two or more thereof. In certain embodiments, the hydrogel/hydrogel formulation of the subject invention comprises at least one binary metal chalcogenide having a formula of $M_xM'_{1-x}X_y$, wherein x=0 or x=1 and $1.5 \le y \le 2.5$. Examples of suitable binary metal chalcogenides include, but are not limited to, $MoS_2$, $ReS_2$, $TiSe_2$, and $WS_2$. In certain embodiments, the hydrogel/hydrogel formulation of the subject invention is free of binary metal chalcogenides.

In certain embodiments, the hydrogel/hydrogel formulation of the subject invention comprises at least one ternary metal chalcogenide having a formula of $M_xM'_{1-x}X_y$, wherein $0<x<1$ and $1.5\leq y\leq 2.5$. In certain embodiments, the hydrogel/hydrogel formulation of the subject invention is free of ternary metal chalcogenides. In certain embodiments, the hydrogel/hydrogel formulation of the subject invention comprises at least one binary metal chalcogenide and at least one ternary metal chalcogenide.

The mixed-metal chalcogenide of the subject invention, whether a binary or ternary metal chalcogenide, may exhibit both POD-like catalytic activity and photothermal properties. This dual functionality enables its use in the treatment of various microbial infections. In particular, the synergistic effect of its POD-like activity and photothermal capabilities enhance antimicrobial efficacy, offering promising strategies for broad biomedical applications.

In specific embodiments, the hydrogel/hydrogel formulation of the subject invention comprises a mixed-metal chalcogenide selected from the group consisting of $MoS_2$, $ReS_2$, $TiSe_2$, $WS_2$, $Mo_{0.25}Re_{0.75}S_2$, $Mo_{0.5}Re_{0.5}S_2$, $Mo_{0.75}Re_{0.25}S_2$, $Mo_{0.42}Re_{0.58}S_{1.94}$, $Mo_{0.66}Re_{0.34}S_{1.85}$, and $Mo_{0.81}Re_{0.19}S_{1.76}$.

In certain embodiments, the thermo-responsive polymer is introduced into the hydrogel/hydrogel formulation to impart thermo-responsiveness, preferably characterized by a temperature-dependent sol-gel transition. In certain embodiments, the thermo-responsive polymer can be any polymer selected from nonionic, amphiphilic triblock copolymers that undergo a reversible sol-to-gel phase transition upon an increase in temperature. In specific embodiments, the thermo-responsive polymer can be any triblock copolymer comprising poly(ethylene oxide) (PEO) and poly(propylene oxide) (PPO) segments.

In specific embodiments, the thermo-responsive polymer is selected from the Pluronic family of block copolymers (also known as Pluronics or poloxamers), which are nonionic, amphiphilic triblock copolymers composed of a central hydrophobic block of poly(propylene oxide) (PPO) flanked by two hydrophilic blocks of poly(ethylene oxide) (PEO), forming a PEO-PPO-PEO structure. Examples of suitable thermo-responsive polymers include, but are not limited to, Pluronic F-127 (PF127), Pluronic F-68 (PF68), and Pluronic F-87 (PF87). These copolymers have excellent thermoreversible properties, enabling reversible sol-gel transitions in response to temperature changes. This thermosensitive behavior, defined by a critical gelation temperature (CGT), makes them highly suitable for a wide range of biomedical and industrial applications, particularly those involving controlled release or stimulus-responsive performance.

Other thermos-responsive polymers that may be used in the hydrogel/hydrogel formulation of the subject invention include both synthetic and natural polymers, as well as copolymers and polymer blends. Examples include poly(N-isopropylacrylamide) (PNIPAAm) and its copolymers; poly (N-vinylcaprolactam) (PVCL); poly(oligo (ethylene glycol) methacrylate) (POEGMA)-based systems; and poly(ethylene glycol)-poly(lactic acid) (PEG-PLA) or PEG-poly (caprolactone) (PEG-PCL) copolymers. Natural or semi-synthetic thermo-responsive systems may include chitosan/β-glycerophosphate, gelatin, methylcellulose, and xyloglucan derivatives. These polymers may be used individually or in combination to tailor gelation temperature, mechanical strength, degradation rate, and drug release kinetics. The thermo-responsive behavior of these polymers makes them particularly suitable for applications such as injectable hydrogels, controlled drug delivery systems, tissue engineering scaffolds, and minimally invasive medical implants.

In certain embodiments, the hydrogel/hydrogel formulation of the subject invention comprises a thermo-responsive polymer selected from the group consisting of PF127, PF68, and PF87, or any combination thereof. In preferred embodiments, the hydrogel/hydrogel formulation comprises PF127 due to its advantageous properties, including a higher gelation temperature, improved gel strength, enhanced stability, and pronounced thermoreversible behavior. These characteristics render PF127 particularly suitable for biomedical applications such as injectable hydrogels, controlled drug delivery systems, wound healing, and tissue engineering. PF127 is a thermoreversible, biocompatible, and bioabsorbable polymer suitable to be employed in the formulation of temperature-sensitive hydrogels. Its ability to undergo a reversible sol-gel transition in response to temperature changes, combined with its excellent solubilizing capacity and low toxicity, further supports its utility in applications such as regenerative medicine.

In certain embodiments, the hydrogel/hydrogel formulation of the subject invention comprises the thermo-responsive polymer in any suitable amount. In certain embodiments, the relative mass ratio between the thermo-responsive polymer and the mixed-metal chalcogenide may be varied within a range of about 300:1 to about 2,000:1, about 500:1 to about 1,800:1, about 500:1 to about 1,500:1, about 700:1 to about 1,200:1, about 700:1 to about 1,000:1, or about 800:1 to about 900:1. Examples of suitable relative mass ratios between the thermo-responsive polymer and the mixed-metal chalcogenide include, but are not limited to, about 400:1, about 500:1, about 600:1, about 700:1, about 750:1, about 800:1, about 850:1, about 900:1, about 950:1, about 1,000:1, about 1,100:1, about 1,200:1, about 1,300:1, about 1,500:1, and about 1,800:1.

In certain embodiments, the matrix polymer is incorporated into the hydrogel/hydrogel formulation to provide a supportive network that enhances gel structure, biocompatibility, and/or mechanical integrity. In certain embodiments, the matrix polymer is selected to improve the structural, biological, and mechanical properties of the resulting hydrogel system.

In specific embodiments, the matrix polymer is selected from saccharide-based biopolymers, preferably hydrophilic polysaccharides. Examples of suitable matrix polymers include, but are not limited to, carboxymethyl chitosan (CMC), chitosan, gelatin, polyethylene glycol (PEG), hyaluronic acid, alginate, dextran, and derivatives thereof. These saccharide-based biopolymers are highly valued in hydrogel applications for their biocompatibility, biodegradability, and functional versatility, making them particularly suitable for drug delivery, wound healing, and tissue engineering. Among these, CMC is notable for its intrinsic antibacterial properties, which helps reduce infection risks in biomedical applications, such as wound healing or drug delivery applications. Additionally, CMC supports cell adhesion and promotes tissue regeneration due to its biological activity.

In certain embodiments, the matrix polymer is selected from the group consisting of CMC, chitosan, gelatin, PEG, hyaluronic acid, pectin, alginate, oxidized cellulose, guar gum, dextran, and derivatives thereof, or any combination thereof. In certain embodiments, synthetic polymers may be used in the formulation, which include, for example, poly (acrylic acid) and its copolymers (e.g., Carbopol®), poly (vinyl alcohol) (PVA), poly(methacrylic acid) or methacrylate copolymers, poly(ethylene glycol), and derivatives thereof.

In preferred embodiments, the hydrogel/hydrogel formulation comprises CMC due to its advantageous properties. As a biodegradable derivative of chitosan, CMC offers improved water solubility, enhanced biocompatibility, superior moisture retention, and strong mucosal adhesion compared to its parent polymer. Additionally, CMC exhibits lower immunogenicity and enhanced antibacterial activity, which is believed to arise from its ability to interact with and disrupt bacterial cell membranes. These unique characteristics make CMC particularly well-suited for various biomedical applications.

In certain embodiments, the matrix polymer is engineered to incorporate one or more functional additives that impart desired properties, such as therapeutic, diagnostic, aesthetic, protective, or performance-enhancing characteristics, tailored to the intended application. Examples of suitable functional additives include, but are not limited to, pharmaceutical agents such as antibiotics, antiviral agents, antifungal agents, chemotherapeutic agents, anti-inflammatory agents, analgesics, and immunomodulators; imaging agents such as fluorescent molecules, luminescent dyes, radiolabels, contrast agents, and nanoparticles (e.g., gold, quantum dots, iron oxide, silica, or upconversion nanoparticles); aesthetic or preservation agents such as pigments, dyes, colorants, fragrances, and preservatives; bioactive compounds such as antimicrobial compounds (e.g., silver nanoparticles, copper ions, or chlorhexidine), growth factors, cytokines, hormones, vitamins, probiotics, prebiotics, and enzymes; protective or stabilizing agents such as antioxidants, UV-blockers, flame retardants, corrosion inhibitors, moisture absorbers, and antistatic agents; genetic materials such as nucleic acids (DNA, RNA, aptamers, or CRISPR-associated components); and functional fillers such as plasticizers, conductive fillers (e.g., carbon nanotubes, graphene, metal nanowires), piezoelectric materials, and magnetic particles.

In certain embodiments, the hydrogel/hydrogel formulation of the subject invention may comprise the matrix polymer in any suitable amount. In certain embodiments, the relative mass ratio between the matrix polymer and the mixed-metal chalcogenide may be varied within a range of about 10:1 to about 500:1, about 10:1 to about 400:1, about 10:1 to about 300:1, about 10:1 to about 200:1, about 10:1 to about 100:1, about 20:1 to about 400:1, about 20:1 to about 300:1, about 20:1 to about 200:1, about 20:1 to about 100:1, about 30:1 to about 400:1, about 30:1 to about 300:1, about 30:1 to about 200:1, about 30:1 to about 100:1, about 40:1 to about 400:1, about 40:1 to about 300:1, about 40:1 to about 200:1, about 40:1 to about 100:1, about 50:1 to about 250:1, about 50:1 to about 200:1, about 50:1 to about 100:1, about 20:1 to about 80:1, about 30:1 to about 70:1, about 40:1 to about 60:1, or about 100:1 to about 200:1. Examples of suitable relative mass ratios between the matrix polymer and the mixed-metal chalcogenide include, but are not limited to, about 20:1, about 30:1, about 40:1, about 50:1, about 60:1, about 70:1, about 80:1, about 90:1, about 100:1, about 150:1, about 200:1, about 250:1, about 300:1, about 350:1, about 400:1, about 450:1, and about 500:1.

In certain embodiments, the hydrogel/hydrogel formulation of the subject invention comprises the thermo-responsive polymer and the matrix polymer at a relative mass ratio of about 30:1 to 1:1, about 28:1 to 2:1, about 25:1 to 5:1, about 22:1 to 8:1, about 20:1 to 10:1, about 19:1 to 12:1, about 20:1 to 15:1, or about 20:1 to 18:1. Examples of suitable relative mass ratios between the thermo-responsive polymer and the matrix polymer include, but are not limited to, about 19:1, about 18:2, about 17:3, about 16:4, about 15:5, about 14:6, about 13:7, about 12:8, about 11:9, and about 1:1.

In certain embodiments, the thermo-responsive polymer and the matrix polymer form the polymeric matrix, in which interactions between thermo-responsive polymer and the matrix polymer (e.g., hydrogen bonding and electrostatic interactions) enhance the structural integrity of the hydrogel and encapsulation of the mixed-metal chalcogenides in the hydrogel.

In certain embodiments, the hydrogel/hydrogel formulation of the subject invention may further comprise a solvent, such that the concentration of the mixed-metal chalcogenide is maintained within a range of about 0.01% to about 50%, about 0.02% to about 40%, about 0.05% to about 30%, about 0.1% to about 20%, about 0.2% to about 10%, about 0.5% to about 5%, about 0.01% to about 1%, about 0.02% to about 2%, about 0.05% to about 5%, about 0.1% to about 10%, about 0.2% to about 20%, about 0.5% to about 30%, about 1% to about 40%, or about 5% to about 50% (w/v). Examples of suitable mixed-metal chalcogenide concentrations include, but are not limited to, about 0.01%, about 0.02%, about 0.05%, about 0.1%, about 0.5%, about 1%, about 5%, about 10%, about 15%, about 20%, about 25%, about 30%, about 35%, about 40%, about 45%, and about 50% (w/v).

In certain embodiments, the concentration of the thermo-responsive polymer in the hydrogel/hydrogel formulation may be maintained within a range of about 1% to about 90%, about 2% to about 80%, about 5% to about 70%, about 5% to about 60%, about 5% to about 50%, about 5% to about 40%, about 5% to about 30%, about 5% to about 20%, about 10% to about 50%, about 10% to about 40%, about 10% to about 30%, or about 10% to about 20% (w/v). Examples of suitable thermo-responsive polymer concentrations include, but are not limited to, about 5%, about 10%, about 15%, about 16%, about 17%, about 18%, about 19%, about 20%, about 25%, about 30%, about 35%, about 40%, about 45%, and about 50% (w/v).

In certain embodiments, the concentration of the matrix polymer in the hydrogel/hydrogel formulation of the subject invention may be maintained within a range of about 0.1% to about 50%, about 0.5% to about 40%, about 1% to about 30%, about 1% to about 20%, about 1% to about 10%, or about 1% to 5% (w/v). Examples of suitable matrix polymer concentrations include, but are not limited to, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, and about 50% (w/v).

In certain embodiments, the combined concentration of the thermo-responsive polymer and the matrix polymer may be maintained within a range of about 1% to about 99.99%, about 1% to about 99.9%, about 1% to about 99%, about 1% to about 95%, about 1% to about 90%, about 5% to about 80%, about 10% to about 60%, about 15% to about 40%, or about 15% to about 30% (w/v). Examples of suitable combined concentrations of the thermo-responsive polymer and the matrix polymer include, but are not limited to, about 1%, about 5%, about 10%, about 15%, about 20%, about 25%, about 30%, about 35%, about 40%, about 45%, and about 50% (w/v).

In certain embodiments, the subject invention provides a composition comprising: (i) a 2D nanomaterials comprising a mixed-metal chalcogenide of the subject invention having a general formula of $M_xM'_{1-x}X_y$, wherein M and M' are distinct transition metal elements, and X is a chalcogen element; and wherein 0≤x≤1 and 1≤y≤3; (ii) a thermo-responsive polymer; and (iii) a matrix polymer.

In certain embodiments, the subject invention provides a composition comprising a hydrogel/hydrogel formulation of the subject invention. In certain embodiments, the composition of the subject invention further comprises a pharmaceutically acceptable carrier.

In certain embodiments, the composition of the subject invention comprises (i) a mixed-metal chalcogenide of the subject invention having a general formula of $M_xM'_{1-x}X_y$, wherein M and M' are distinct transition metal elements, and X is a chalcogen element; and wherein 0≤x≤1 and 1≤y≤3; (ii) a thermo-responsive polymer; (iii) a matrix polymer, and (iv) a pharmaceutically acceptable carrier.

As used herein, a "pharmaceutically acceptable carrier" refers to a diluent, adjuvant or excipient with which the composition disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith. Examples of pharmaceutically acceptable carriers suitable for use in the compositions are known in the art and such embodiments are within the purview of the invention.

In certain embodiments, the composition of the subject invention comprises a pharmaceutically acceptable carrier suitable for topical or dermal application, particularly for wound management. Such pharmaceutically acceptable carriers, whether used individually or in combination, may facilitate formulation, enhance delivery of the active components, improve retention at the application site, and support skin compatibility and overall biocompatibility.

Examples of suitable pharmaceutically acceptable carriers include, but are not limited to, aqueous carriers, such as purified water, saline (0.9% NaCl solution), buffered saline solutions (e.g., phosphate-buffered saline, PBS); polymeric gelling or thickening agents, such as carbomers (e.g., Carbopol®), hydroxypropyl methylcellulose (HPMC), hydroxyethyl cellulose (HEC), or xanthan gum; emollients and moisturizers, such as glycerin (glycerol), propylene glycol, or dimethicone (a silicone-based emollient); surfactants and penetration enhancers, such as polysorbates (e.g., Tween 20, Tween 80), lecithin, or fatty alcohols (e.g., cetyl alcohol, stearyl alcohol); preservatives, such as benzalkonium chloride, methylparaben/propylparaben, or phenoxyethanol; and pH adjusters/buffers, such as citric acid/sodium citrate, lactic acid/sodium lactate, or acetic acid/sodium acetate.

In certain embodiments, the composition of the subject invention may further comprise one or more additional therapeutic agents. The inclusion of such agents may offer various advantages, including synergistic or additive therapeutic effects, dose reduction (sparing effect), multi-targeted action, overcoming drug resistance or tolerance, enhanced bioavailability or pharmacokinetic profile, mitigation of side effects, and/or providing sequential or complementary therapeutic effects. Examples of suitable additional therapeutic agents include, but are not limited to, antibiotics, such as mupirocin, neomycin, bacitracin, gentamicin, or silver sulfadiazine; anti-inflammatory agents, such as corticosteroids (e.g., hydrocortisone, dexamethasone), or non-steroidal anti-inflammatory drugs (NSAIDs, e.g., diclofenac, ibuprofen); analgesics/local anesthetics, such as lidocaine, benzocaine, or pramoxine; growth factors and cytokines, such as epidermal growth factor (EGF), fibroblast growth factor (FGF), vascular endothelial growth factor (VEGF), or transforming growth factor-beta (TGF-β); antioxidants, such as vitamin E (tocopherol), vitamin C (ascorbic acid), glutathione, or N-acetylcysteine; antiseptics/antimicrobial agents, such as chlorhexidine, iodine (e.g., povidone-iodine), or silver nanoparticles; antifungal agents, such as clotrimazole, miconazole, or nystatin; immunomodulatory agents, such as tacrolimus or pimecrolimus; chelating agents, such as EDTA; probiotics or microbiome modulators; hemostatic agents, such as thrombin or fibrinogen; cell signaling modulators or small molecules, such as nitric oxide donors, retinoids, or siRNAs.

In certain embodiments, the composition of the subject invention can be formulated for administration via routes suitable for localized or systemic therapeutic delivery, with particular preference for topical, transdermal, intradermal, or subcutaneous application. These routes are especially suitable for treating skin disorders, chronic and acute wounds (e.g., diabetic ulcers, pressure sores, surgical wounds, or burns), and for promoting tissue regeneration and repair of epithelial or soft connective tissues. The thermo-responsive hydrogel properties of the composition allow it to be administered as a liquid at ambient temperature and undergo in situ gelation at physiological temperatures, facilitating improved retention, targeted release, and/or patient comfort.

To facilitate administration, the composition may be delivered using a variety of medical or drug delivery devices, including but being not limited to, pre-filled syringes or injectors for subcutaneous or intradermal injection; topical applicators, such as spreaders, spray nozzles, or gel dispensers for direct skin application; hydrogel patches or wound dressings designed to maintain a moist environment and sustained release of therapeutic agents; microneedle arrays or dermal rollers for enhanced skin penetration and localized drug delivery; and transdermal delivery systems, such as medicated adhesive patches, when used in combination with a permeation enhancer or skin-compatible carrier.

In certain embodiments, the composition may also be adapted for buccal, sublingual, nasal, or injectable delivery routes, such as intramuscular, intraperitoneal, or intra-arterial injection, provided the composition maintains hydrogel integrity, dispersibility, and biocompatibility under the relevant physiological conditions.

In certain embodiments, the composition of the subject invention may be formulated into pharmaceutical preparations suitable for a variety of delivery routes and clinical applications. Due to the thermo-responsive hydrogel nature of the composition, it is particularly suitable for semi-solid formulations, injectable hydrogels, topical applications, and in situ gelling systems, which can transition from a liquid to a gel state at physiological temperature to facilitate localized retention and sustained release.

Although the composition may be adaptable for other formats, including solutions, suspensions, emulsions, aerosols, or solid dosage forms, its preferred use is in topical, transdermal, intradermal, or subcutaneous applications, especially for the treatment of skin disorders, wounds, burns, and soft tissue injuries. In specific embodiments, the composition may be applied as a wound dressing, patch, or injectable formulation to form a protective, bioactive barrier at the target site.

In certain embodiments, the composition can be formulated as a solution or suspension suitable for injection, including subcutaneous, intramuscular, intraperitoneal, or intravenous delivery, depending on the disease target and therapeutic agent. Parenteral formulations may comprise non-toxic, pharmaceutically acceptable diluents or solvents, such as water for injection (WFI), isotonic sodium chloride, Ringer's solution, glycerol, or mannitol. Suitable emulsifying or suspending agents may include polyethylene glycol (PEG), propylene glycol, or phosphate-buffered saline (PBS). Biocompatible oil-in-water emulsions (e.g., based on squalene or parenteral-grade vegetable oils) may also be used for hydrophobic therapeutic agents incorporated into the hydrogel matrix. Illustrative examples of suitable carriers include, but are not limited to, for intravenous use: mixtures of 10% USP ethanol, 40% polyethylene glycol 600 or propylene glycol, and USP WFI; or 0.01-0.2% phospholipids (e.g., dipalmitoyl diphosphatidylcholine) in WFI; and for subcutaneous or intramuscular use: PBS, 5% dextrose in WFI, 0.9% sodium chloride, and mild surfactants or dispersing agents compatible with hydrogel systems.

In certain embodiments, the composition can be presented in unit dose formats such as pre-filled syringes, ampoules, or sterile vials, or in multi-dose containers with or without added preservatives, depending on clinical and storage requirements. In certain cases, the composition may be lyophilized and reconstituted prior to use to provide long-term stability.

In some embodiments, the composition of the subject invention is provided in a unit dosage form, wherein the composition is subdivided into individual doses containing therapeutically appropriate quantities of one or more biologically active agents. The unit dosage form may be tailored to the specific route of administration, formulation type, and clinical indication, and may include pre-filled syringes, ampoules, vials, sachet-packaged gels, or hydrogel patches for topical or injectable use.

In certain embodiments, the unit dosage form may comprise a premeasured volume of injectable thermos-responsive hydrogel, for example, 0.1 mL to 10 mL per unit, containing predefined concentrations of the active components, such as the mixed-metal chalcogenide and optionally, one or more additional therapeutic agents. For topical or dermal applications, the unit dosage may include pre-formed or in situ forming hydrogels packaged in single-use sterile applicators, wound dressings, or biodegradable film formulations.

The amount of a therapeutically active agent (e.g., the mixed-metal chalcogenide and optionally, one or more additional therapeutic agents) contained in each unit dose may vary depending on the disease indication, target tissue, and method of delivery. In various embodiments, the dosage amount of the mixed-metal chalcogenide and optionally, additional therapeutic agents in a single administration may range from about 0.1 mg to about 5000 mg, including about 0.1 mg to 1000 mg, 0.5 mg to 250 mg, or 1 mg to 100 mg. The precise dosage may be determined based on factors such as bioavailability, local vs. systemic delivery, wound size, treatment frequency, and patient-specific parameters.

Method of Preparation

The subject invention provides methods for preparing the mixed-metal chalcogenide compounds of the subject invention. In certain embodiments, the subject invention provides a method of synthesizing the mixed-metal chalcogenide of the subject invention. Synthesis of the mixed-metal chalcogenide can be achieved by a reaction between metal precursor(s) and chalcogen precursor(s) under a hydrothermal condition.

In certain embodiments, the subject invention provides a method of synthesizing the mixed-metal chalcogenide using a hydrothermal process, comprising reacting one or more metal precursors and one or more chalcogen precursors under a hydrothermal condition. In specific embodiments, the method comprises mixing one or more metal precursors and one or more chalcogen precursors in an aqueous solution, and subjecting the solution to a hydrothermal treatment for a defined period of time to yield the desired mixed-metal chalcogenide. In specific embodiments, the method further comprises, following the reaction, recovering, purifying, and optionally drying the resulting product.

In certain embodiments, the synthesis of the mixed-metal chalcogenide of the subject invention involves the use of one or more metal precursors that are water-soluble or hydrothermally reactive. Depending on the desired transition metal elements M and M' to be incorporated into the resulting chalcogenide product, suitable metal precursors may include compounds containing Mo, W, Re, Nb, Ta, V, Ti, Zr, and Hf. In some embodiments, the metal precursors may include, but are not limited to, molybdenum precursors such as ammonium orthomolybdate ($(NH_4)_2MoO_4$) and sodium molybdate ($Na_2MoO_4$), tungsten precursors such as ammonium metatungstate ($(NH_4)_6[H_2W_{12}O_{40}]$) and sodium tungstate ($Na_2WO_4$), rhenium precursors such as ammonium perrhenate ($NH_4ReO_4$) and rhenium trioxide ($ReO_3$), niobium precursors such as niobium (V) chloride ($NbCl_5$) and niobium oxalate, tantalum precursors such as tantalum (V) ethoxide and tantalum pentachloride ($TaCl_5$), vanadium precursors such as vanadyl sulfate ($VOSO_4$) and ammonium metavanadate ($NH_4VO_3$), titanium precursors such as titanium (IV) isopropoxide and titanium oxysulfate ($TiOSO_4$), zirconium precursors such as zirconium (IV) oxychloride octahydrate ($ZrOCl_2 \cdot 8H_2O$) and zirconium (IV) nitrate pentahydrate ($Zr(NO_3)_4 \cdot 5H_2O$), and hafnium precursors such as hafnium (IV) chloride ($HfCl_4$) and hafnium (IV) oxychloride octahydrate ($HfOCl_2 \cdot 8H_2O$). The selected metal precursors may be used individually or in combination to achieve the desired metal composition and stoichiometry of the resulting chalcogenide product. In certain embodiments, two or more distinct metal precursors are combined to produce a mixed-metal chalcogenide comprising multiple transition metal elements.

In certain embodiments, the synthesis of the mixed-metal chalcogenide of the subject invention involves the use of one or more chalcogen precursors selected to provide chalcogen elements such as O, S, Se, and Te. Suitable chalcogen precursors may include, but are not limited to, oxygen precursors such as hydrogen peroxide ($H_2O_2$) and metal oxides; sulfur precursors such as thiourea, thioacetamide, elemental sulfur, and hydrogen sulfide ($H_2S$); selenium precursors such as sodium selenite ($Na_2SeO_3$), sodium selenide ($Na_2Se$), and selenourea; and tellurium precursors such as tellurium dioxide ($TeO_2$), sodium tellurite ($Na_2TeO_3$), and elemental tellurium. These chalcogen precursors may be used individually or in combination, depending on the desired chalcogen content and stoichiometry of the resulting chalcogenide product. In certain embodiments, the chalcogen precursors are selected to match or complement the metal precursor reactivity under hydrothermal conditions.

The ratio of the metal precursors to the chalcogen precursors may be varied to produce different stoichiometries of the resulting mixed-metal chalcogenide. In certain embodiments, the relative molar ratio between the total metal precursors and the total chalcogen precursors may be controlled to fall within a range suitable for forming layered or crystalline chalcogenide structures. For example, the metal-to-chalcogen molar ratio used in the synthesis process may be about 1:1.8, about 1:1.85, about 1:1.9, about 1:1.95, about 1:2, about 1:2.05, about 1:2.1, about 1:2.15, about 1:2.2, about 1.2.25, about 1:2.3, about 1:2.35, about 1:2.4, about 1:2.45, or about 1:2.5, depending on the specific metal and chalcogen precursors used, their reactivity, and the desired composition of the final product. In certain embodiments, the metal-to-chalcogen molar ratio is in a range from about 1:1 to 1:3, from about 1:1 to 1:2.9, from about 1:1 to 1:2.8, from about 1:1 to 1:2.7, from about 1:1 to 1:2.6, from about 1:1 to 1:2.5, from about 1:1 to 1:2.4, from about 1:1 to 1:2.3, from about 1:1 to 1:2.2, from about 1:1 to 1:2.1, from about 1:1 to 1:2, from about 1:1 to 1:1.95, from about 1:1 to 1:1.9, from about 1:1 to 1:1.85, from about 1:1 to 1:1.8, from about 1:1 to 1:1.75, from about 1:1 to 1:1.7, from about 1:1 to 1:1.65, from about 1:1 to 1:1.6, from about 1:1 to 1:1.55; from about 1:1 to 1:1.5, from about 1:1 to 1:1.45, from about 1:1 to 1:1.4, from about 1:1 to 1:1.35, or from about 1:1 to 1:1.3. In specific embodiments, the metal-to-chalcogen molar ratio is about 1:2, about 1:1.94, about 1:1.85, or about 1:1.76.

In specific embodiments, for synthesizing the mixed-metal chalcogenide of the subject invention, the relative molar ratio between the M precursor and the M' precursor may be varied to achieve the desired mixed-metal composition of the final product. In certain embodiments, the M-to-M' molar ratio is in a range from about 0:1 to 1:0, from about 0.05:0.95 to 0.95:0.05, from about 0.1:0.9 to 0.9:0.1, from about 0.15:0.85 to 0.85:0.15, from about 0.2:0.8 to 0.8:0.2, from about 0.25:0.75 to 0.75:0.25, from about 0.3:0.7 to 0.7:0.3, from about 0.35:0.65 to 0.65:0.35, from about 0.4:0.6 to 0.6:0.4, or from 0.45:0.55 to 0.55:0.45. In some embodiments, the M-to-M' molar ratio may be selected from, for example, about 0:1, about 0.05:0.95, about 0.1:0.9, about 0.15:0.85, about 0.2:0.8, about 0.25:0.75, about 0.3:0.7, about 0.35:0.65, about 0.4:0.6, about 0.45:0.55, about 0.5:0.5, about 0.55:0.45, about 0.6:0.4, about 0.65:0.35, about 0.7:0.3, about 0.75:0.25, about 0.8:0.2, about 0.85:0.15, about 0.9:0.1, about 0.95:0.05, or about 1:0.

In certain embodiments, a reducing agent can be added to the reaction mixture to facilitate the reduction of metal precursors, for example, by converting transition metal ions from higher oxidation states (e.g., $Mo^{6+}$, $Re^{7+}$) to lower oxidation states (e.g., $Mo^{4+}$, $Re^{4+}$), which are more favorable for the formation of layered transition metal chalcogenide (TMC) structures. This redox control promotes the formation of the desired crystalline phase and may enhance the uniformity, purity, and crystallinity of the resulting chalcogenide product. In some embodiments, the presence of the reducing agent may also suppress the formation of undesired metal oxides or hydroxides and improve the overall stability of the reaction environment. Suitable reducing agents may be selected from, for example, hydroxylamine hydrochloride ($NH_2OH \cdot HCl$), ascorbic acid, sodium borohydride, hydrazine hydrate, or any other reductants compatible with aqueous or hydrothermal reaction systems.

The amount of the reducing agent may be adjusted relative to the total amount of the metal precursors to tune the redox conditions and optimize product formation. In certain embodiments, for providing a favorable redox environment for the hydrothermal crystallization process and results in enhanced yield, crystallinity, and phase uniformity of the resulting chalcogenide product, the molar amount of the reducing agent used in the reaction may range from about 1.2 to about 2.0 equivalents relative to the total moles of the metal precursors. In specific embodiments, the relative molar ratio between the reducing agent and the total metal precursors may be, for example, about 1.2:1, about 1.3:1, about 1.4:1, about 1.5:1, about 1.6:1, about 1.7:1, about 1.8:1, about 1.9:1, or about 2:1.

In certain embodiments, the hydrothermal treatment may be carried out by sealing an aqueous solution comprising the one or more metal precursors and one or more chalcogen precursors within a pressure-resistant reaction vessel, such as a sealed Teflon-lined autoclave, and heating to an elevated temperature under autogenous pressure. In specific embodiments, the pressure-resistant reaction vessel may be heated to a temperature from about 180° C. to about 250° C. In specific embodiments, the temperature can be, for example, about 180° C., about 190° C., about 200° C., about 210° C., about 220° C., about 230° C., about 240° C., or about 250° C., depending on the reactivity of the selected precursors and the desired physicochemical properties of the resulting mixed-metal chalcogenide product.

In certain embodiments, the duration of the hydrothermal treatment may be from about 6 hours to about 36 hours, for example, about 6 hours, about 9 hours, about 12 hours, about 15 hours, about 18 hours, about 21 hours, about 24 hours, about 27 hours, about 30 hours, about 33 hours, or about 36 hours, to allow sufficient time for crystallization, phase development, and nanostructure formation of the target chalcogenide material.

In certain embodiments, the method of synthesizing the mixed-metal chalcogenide of the subject invention may further comprise, following completion of the reaction, recovering the resulting product, for example, by centrifugation. In certain embodiments, the method may further comprise purifying the resulting product of the reaction through one or more washing steps, for example, washing with water, to remove any unreacted precursors, soluble byproducts, or residual impurities. In certain embodiments, the method may also comprise drying the product, for example, under vacuum, in a low-temperature oven, or by air drying, to yield the final mixed-metal chalcogenide material in solid form.

In certain embodiments, the subject invention further provides a method of preparing the hydrogel/hydrogel formulation of the subject invention, comprising incorporating the mixed-metal chalcogenide of the subject invention into a thermo-responsive polymer mixed with a matrix polymer. In certain embodiments, the method comprises, prior to mixing with the thermo-responsive polymer and the matrix polymer, preparing a dispersion solution of the mixed-metal chalcogenide.

In certain embodiments, the dispersion solution of the mixed-metal chalcogenide can be prepared by adding the mixed-metal chalcogenide to a dispersive solvent, and mixing through, for example, stirring and/or sonication, to achieve a homogeneous dispersion. Examples of suitable dispersive solvents include, but are not limited to, ethanol, N-methyl-pyrrolidone (NMP), isopropanol (IPA), or dimethyl sulfoxide (DMSO). In certain embodiments, the concentration of the mixed-metal chalcogenide in the dispersion solution may be from about 1% to about 10% weight/volume (w/v), while maintaining good dispersibility and stability.

In specific embodiments, the mixing of the mixed-metal chalcogenide and the dispersive solvent can be performed through probe sonication for a period of, for example, about 30 minutes, followed by further agitation using a mixer or magnetic stirrer operated at a rotational speed of, for example, 20 to 200 rpm. The mixing process can be continued for a sufficient duration, for example, ranging from about 30 minutes to about 24 hours, until the mixed-metal chalcogenide is fully dispersed within the dispersive solvent.

In certain embodiments, the method further comprises dissolving the thermo-responsive polymer and the matrix polymer in a hydrophilic solvent to form a homogeneous mixed solution. The hydrophilic solvent may be selected from aqueous solvents, such as water or aqueous buffer, as well as alcohols, such as ethanol, or any other cell-compatible media, depending on the intended in vitro or in vivo biological application of the resulting composition. In specific embodiments, the cell-compatible medium may be a cell culture medium, for example, a complete Dulbecco's Modified Eagle Medium (DMEM) supplemented with fetal bovine serum (FBS), penicillin/streptomycin (P/S), and non-essential amino acids (NEAA).

In certain embodiments, the method further comprises mixing the prepared dispersion solution of the mixed-metal chalcogenide with the mixed solution of the thermo-responsive polymer and the matrix polymer to achieve a homogeneous hydrogel formulation. In specific embodiments, mixing 1) the dispersion solution of the mixed-metal chalcogenide and 2) the mixed solution of the thermo-responsive polymer and the matrix polymer may be performed within an airtight container through agitation using a mixer or magnetic stirrer operated at a rotational speed of, for example, 20 to 200 rpm for a sufficient duration, for example, ranging from about 30 minutes to about 24 hours to ensure homogeneity. Optionally, the method may comprise adding an appropriate amount of the aqueous solvent to adjust the final concentrations of the mixed-metal chalcogenide, the thermo-responsive polymer, and the matrix polymer as desired.

In specific embodiments, the method of preparing the hydrogel/hydrogel formulation of the subject invention comprises steps of:

1) Preparing a dispersion solution of mixed-metal chalcogenides;
2) Dissolving the thermo-responsive polymer and the matrix polymer in a hydrophilic solvent to form a mixed solution; and
3) Mixing the dispersion solution obtained in step 1) and the mixed solution obtained in step 2), and optionally, adding a solvent, to achieve a homogeneous hydrogel formulation.

In certain embodiments, after mixing, the hydrogel formulation solution is stored as liquid status.

Applications

The antimicrobial activity, photothermal property, and biocompatibility of the mixed-metal chalcogenides and the hydrogels of the subject invention make them well-suited for a wide range of biomedical applications, including, but being not limited to, antibacterial or antifungal treatments, and photothermal therapy. Accordingly, the subject invention provides methods and strategies of utilizing the mixed-metal chalcogenides and hydrogels across diverse therapeutic and diagnostic settings.

In certain embodiments, the subject invention provides a method of inhibiting the growth and/or reproduction of microbial pathogens, and/or killing microbial pathogens in a cell, tissue, or organism, the method comprising administering to the cell, tissue, or organism an effective amount of the mixed-metal chalcogenide of the subject invention, the hydrogel/hydrogel formulation of the subject invention, or the composition of the subject invention.

Administration may be carried out either in vitro or in vivo and may be selected and/or optimized based on factors such as the type of microbial pathogen, the site of infection, and the desired therapeutic effect. In specific embodiments, administering to the cell, tissue, or organism an effective amount of the mixed-metal chalcogenide of the subject invention, the hydrogel/hydrogel formulation of the subject invention, or the composition of the subject invention comprises introducing the mixed-metal chalcogenide of the subject invention, the hydrogel/hydrogel formulation of the subject invention, or the composition of the subject invention into a culture containing the cell, tissue, or organism, or delivering the mixed-metal chalcogenide of the subject invention, the hydrogel/hydrogel formulation of the subject invention, or the composition of the subject invention into the cell, tissue, or organism via any pharmaceutically acceptable route, including but not limited to topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites).

In specific embodiments, the method comprises injecting the mixed-metal chalcogenide of the subject invention, the hydrogel/hydrogel formulation of the subject invention, or the composition of the subject invention into a culture containing the cell, tissue, or organism, or injecting the mixed-metal chalcogenide of the subject invention, the hydrogel/hydrogel formulation of the subject invention, or the composition of the subject invention into or onto the cell, tissue, or organism.

In certain embodiments, the method comprises applying the mixed-metal chalcogenide of the subject invention, the hydrogel/hydrogel formulation of the subject invention, or the composition of the subject invention to a target site including, but being not limited to, a wound, an infected or inflamed tissue, a tumor, a surgical site, and a specific organ or cavity (e.g., joint, eye, nasal passage).

The mixed-metal chalcogenide of the subject invention, the hydrogel/hydrogel formulation of the subject invention, or the composition of the subject invention can target a broad range of microbial pathogens due to, for example, the POD-like activity and the photothermal property, which disrupt microbial membranes, generate reactive oxygen species (ROS), and/or induce thermal damage under NIR irradiation.

In certain embodiments, the microbial pathogens that are targeted by the method of the subject invention include, but are not limited to, fungal pathogens, such as yeasts (e.g., *Candida albicans*), molds (e.g., *Aspergillus fumigatus, Trichophyton rubrum*), or dermatophytes; bacterial pathogens, such as gram-positive bacteria (e.g., *Staphylococcus aureus, Streptococcus pneumoniae*), or gram-negative bacteria (e.g., *Escherichia coli, Pseudomonas aeruginosa, Klebsiella pneumoniae*); biofilm-forming pathogens, such as *Staphylococcus epidermidis*, or *Candida* spp. biofilms; opportunistic pathogens, such as *Cryptococcus neoformans, Nocardia* spp., or *Acinetobacter baumannii*; and drug-resistant microbes, such as multidrug-resistant (MDR) *Pseudomonas aeruginosa*, extended-spectrum β-lactamase (ESBL)-producing *E. coli*, or fluconazole-resistant *Candida glabrata.*

The subject invention is not limited by the specific type, source, or physiological state of the cell, tissue, or organism. The cell, tissue, or organism may be living or non-living, derived from any biological source, and may be healthy, diseased, or in any intermediate condition. In certain embodiments, the cell is of mammalian origin, preferably a human or mouse cell. In specific embodiments, the cell may be a HeLa cell or a mouse embryonic fibroblast cell, such as an NIH 3T3-GFP cell.

In certain embodiments, the method of the subject invention may utilize one or more reactive oxygen species (ROS)-generating agents to activate or enhance the catalytic activity of the mixed-metal chalcogenide nanozymes or the compositions comprising the same, particularly their POD-like behavior. As used herein, a "ROS-generating agent" refers to a chemical compound, biological system, or catalytic reagent that, upon activation or under suitable reaction conditions, produces reactive oxygen species such as hydrogen peroxide ($H_2O_2$), superoxide anion ($O_2^{-}\cdot$), hydroxyl radical ($\cdot OH$), singlet oxygen ($^1O_2$), or other oxygen-centered radicals or oxidizing species.

In certain embodiments, the ROS-generating agents suitable for use in the present invention may function either by directly releasing ROS or by participating in redox reactions that give rise to ROS. Examples of such ROS-generating agents include, but are not limited to, peroxides, such as hydrogen peroxide ($H_2O_2$), tert-butyl hydroperoxide, and cumene hydroperoxide; peracids, including peracetic acid and m-chloroperbenzoic acid (m-CPBA); ozonides and ozone-releasing compounds; photosensitizers, such as methylene blue, rose bengal, or porphyrin derivatives, which produce ROS (e.g., singlet oxygen) upon exposure to light; redox enzyme systems, including, but not limited to, glucose oxidase in the presence of glucose, which generates hydrogen peroxide enzymatically; metal-catalyzed systems, such as Fenton-type reagents (e.g., $Fe^{2+}/H_2O_2$), capable of generating hydroxyl radicals; and other organic or inorganic oxidants that can induce or amplify oxidative processes under biological or experimental conditions.

Advantageously, the mixed-metal chalcogenide of the subject invention, the hydrogel/hydrogel formulation of the subject invention, or the composition of the subject invention exhibits POD-like activity in the presence of one or more ROS-generating agents, and additionally exhibit a photothermal effect upon irradiation, such as near-infrared (NIR) light. Both the POD-like catalytic activity and the photothermal property contribute independently or synergistically to the inhibition and/or killing of microbial pathogens, including fungi and bacteria.

In certain embodiments, the method of the subject invention comprises, before, after, or simultaneously with the administering step, treating the cell, tissue, or organism with one or more ROS-generating agents and/or exposing the cell, tissue, or organism to NIR irradiation. These treatments can be carried out either in vitro or in vivo and may be selected and/or optimized based on factors such as the type of microbial pathogen, the site of infection, and the desired therapeutic effect.

In specific embodiments, treating the cell, tissue, or organism with one or more ROS-generating agents comprises introducing the agent(s) into a culture containing the cell, tissue, or organism, or delivering the agent(s) into the cell, tissue, or organism via any pharmaceutically acceptable route, including but not limited to topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites).

In certain embodiments, the method further comprises applying NIR irradiation to a culture containing the cell, tissue, or organism, or directly to at least a portion of the cell, tissue, or organism, for a period of time, such as about 10 minutes, to induce photothermal activity and enhance microbial killing. In certain embodiments, the method comprises repeating cycles of NIR irradiation and passive cooling, preferably, for 3 to 5 cycles, to verify the reproducibility and sustained efficacy of the photothermal effect.

In certain embodiments, the method of the subject invention may comprise, in the presence of one or more ROS-generating agents and/or under NIR irradiation, administering to the cell, tissue, or organism an effective amount of the mixed-metal chalcogenide of the subject invention, the injectable hydrogel/hydrogel formulation of the subject invention, or the composition of the subject invention.

The mixed-metal chalcogenide, the injectable hydrogel/hydrogel formulation, or the composition of the subject invention exhibits antimicrobial activity by inhibiting the growth and/or reproduction of microbial pathogens, and/or by directly killing the pathogens, even without any ROS-generating agent and/or NIR irradiation.

In certain embodiments, the method further comprises, before, after, or simultaneously with the administering step, measuring the local or systemic temperature at the site of application to monitor photothermal activation of the mixed-metal chalcogenide, the injectable hydrogel/hydrogel formulation, or the composition of the subject invention, and to prevent overheating of surrounding cells or tissues.

In certain embodiments, the method of the subject invention further comprises, before, after, or simultaneously with the administering step, testing the photothermal conversion efficiency of the injectable hydrogel/hydrogel formulation or the composition of the subject invention to confirm sufficient energy conversion for effective microbial inactivation. In certain embodiments, the method may further comprise adjusting one or more parameters of the NIR irradiation, such as intensity, exposure duration, or beam diameter, to optimize photothermal activation based on the treatment site, microbial load, and/or patient-specific conditions.

In certain embodiments, the method of the subject invention further comprises, before, after, or simultaneously with the administering step, detecting or quantifying POD-like catalytic activity of the mixed-metal chalcogenide, the injectable hydrogel/hydrogel formulation, or the composition of the subject invention.

In certain embodiments, the method of the subject invention further comprises, before, after, or simultaneously with the administering step, monitoring the viability of cells or cells from the tissue or the organism exposed to the mixed-metal chalcogenide, the injectable hydrogel/hydrogel formulation, or the composition of the subject invention, such as through in vitro cell viability assays (e.g., CCK-8 assay), to evaluate biocompatibility and minimize cytotoxic effects.

In certain embodiments, the method of the subject invention further comprises, before, after, or simultaneously with the administering step, examining the morphology of microbial pathogens, such as using electron microscopy (e.g., SEM or TEM), to detect structural changes indicative of antimicrobial action, such as membrane rupture or surface collapse. In certain embodiments, the method of the subject invention may further comprise, before, after, or simultaneously with the administering step, quantifying microbial viability, such as by determining colony forming units (CFUs) through a spread plate assay under various treatment conditions.

In certain embodiments, the method of the subject invention further comprises, before, after, or simultaneously with the administering step, characterizing the pore structure and morphological integrity of the mixed-metal chalcogenide, the injectable hydrogel/hydrogel formulation, or the composition of the subject invention, such as using imaging techniques, to monitor physical changes resulting from mechanical stress, thermal exposure, or biological interactions.

In certain embodiments, the method of the subject invention further comprises, before, after, or simultaneously with the administering step, selecting or adjusting the composition of the mixed-metal chalcogenide based on their cytotoxicity profiles, photothermal efficiency, and/or biocompatibility in specific application settings.

In certain embodiments, the subject invention provides a method of treating or preventing microbial infections in a subject in need thereof, the method comprising administering to the subject an effective amount of the mixed-metal chalcogenide, the injectable hydrogel/hydrogel formulation, or the composition of the subject invention.

As used herein, a "subject in need thereof" refers to any subject requiring treatment for a microbial infection, including those diagnosed with or suspected of having such an infection. The subject invention is not limited by the specific type, origin, or physiological condition of the subject to which the mixed-metal chalcogenide, the injectable hydrogel/hydrogel formulation, or the composition of the subject invention is administered. In certain embodiments, the subject is a mammal, including but not limited to a human or a mouse.

Administration of the mixed-metal chalcogenide, the injectable hydrogel/hydrogel formulation, or the composition of the subject invention may be selected and/or optimized based on factors such as the type of microbial pathogen, the site of infection, and the desired therapeutic effect. In specific embodiments, administering to the subject an effective amount of the mixed-metal chalcogenide, the injectable hydrogel/hydrogel formulation, or the composition of the subject invention comprises introducing or delivering the mixed-metal chalcogenide, the injectable hydrogel/hydrogel formulation, or the composition of the subject invention into the subject via any pharmaceutically acceptable route, including but not limited to topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites).

In specific embodiments, the method may comprise injecting the mixed-metal chalcogenide, the injectable hydrogel/hydrogel formulation, or the composition of the subject invention into or onto the subject. In certain embodiments, the method may comprise applying the mixed-metal chalcogenide, the injectable hydrogel/hydrogel formulation, or the composition of the subject invention only to a target site including, but being not limited to, a wound, an infected or inflamed tissue, a tumor, a surgical site, or a specific organ or cavity (e.g., joint, eye, nasal passage).

In certain embodiments, the microbial infection is an infection caused by microbial pathogens including, but being not limited to, fungal pathogens, such as yeasts (e.g., *Candida albicans*), molds (e.g., *Aspergillus fumigatus, Trichophyton rubrum*), or dermatophytes; bacterial pathogens, such as gram-positive bacteria (e.g., *Staphylococcus aureus, Streptococcus pneumoniae*), or gram-negative bacteria (e.g., *Escherichia coli, Pseudomonas aeruginosa, Klebsiella pneumoniae*); biofilm-forming pathogens, such as *Staphylococcus epidermidis*, or *Candida* spp. biofilms; opportunistic pathogens, such as *Cryptococcus neoformans, Nocardia* spp., or *Acinetobacter baumannii*; and drug-resistant microbes, such as MDR *Pseudomonas aeruginosa*, ESBL-producing *E. coli*, or fluconazole-resistant *Candida glabrata*.

In certain embodiments, the method of the subject invention comprises, before, after, or simultaneously with the administering step, treating the subject with one or more ROS-generating agents and/or exposing the subject to NIR irradiation. These treatments may be selected and/or optimized based on factors such as the type of microbial pathogen, the site of infection, and the desired therapeutic effect. In specific embodiments, treating the subject with one or more ROS-generating agents comprises administering the agent(s) to the subject via any pharmaceutically acceptable route, including but not limited to topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites).

In certain embodiments, the method of the subject invention comprises applying NIR irradiation to the subject for a period of time, such as about 10 minutes, to induce photothermal activity and enhance microbial killing. In certain embodiments, the method comprises repeating cycles of NIR irradiation and passive cooling, for example, for 3 to 5 cycles, to verify the reproducibility and sustained efficacy of the photothermal effect.

In certain embodiments, the method of the subject invention comprises, in the presence of one or more ROS-generating agents and/or under NIR irradiation, administering to the subject an effective amount of the mixed-metal chalcogenide, the hydrogel/hydrogel formulation, or the composition of the subject invention.

In certain embodiments, the method of the subject invention further comprises, before, after, or simultaneously with the administering step, measuring the local or systemic temperature at the site of application to monitor photothermal activation of the mixed-metal chalcogenide, the injectable hydrogel/hydrogel formulation, or the composition, and to prevent overheating of surrounding tissues.

In certain embodiments, the method of the subject invention further comprises, before, after, or simultaneously with the administering step, monitoring the viability of a cell of the subject exposed to the mixed-metal chalcogenide, the injectable hydrogel/hydrogel formulation, or the composition of the subject invention, such as through in vitro cell viability assays (e.g., CCK-8 assay), to evaluate biocompatibility and minimize cytotoxic effects.

In certain embodiments, the subject invention provides a method of managing a wound in a subject, comprising administering to the wound an effective amount of the mixed-metal chalcogenide of the subject invention, the hydrogel/hydrogel formulation of the subject invention, or the composition of the subject invention.

As used herein, "managing a wound" refers to any therapeutic intervention directed toward improving the condition of a wound. This includes, but is not limited to, treating a wound, promoting wound healing, facilitating wound care, addressing a wound, or providing therapeutic care for a wound. Such management involves preventing or controlling infection, enhancing tissue regeneration, reducing inflammation, or maintaining a suitable wound environment.

In certain embodiments, the subject invention provides a method for preventing or treating an infection at a wound, the method comprising administering to the wound an effective amount of the mixed-metal chalcogenide of the subject invention, the hydrogel/hydrogel formulation of the subject invention, or the composition of the subject invention.

In certain embodiments, the subject invention provides a method for protecting a wound from an infection (e.g., microbial infection), the method comprising administering to the wound an effective amount of the mixed-metal chalcogenide of the subject invention, the hydrogel/hydrogel formulation of the subject invention, or the composition of the subject invention.

In certain embodiments, the subject invention provides a method for promoting wound healing in a subject, the method comprising administering to a subject having a wound an effective amount of the mixed-metal chalcogenide of the subject invention, the hydrogel/hydrogel formulation of the subject invention, or the composition of the subject invention.

In certain embodiments, the subject invention provides a method for promoting tissue regeneration at a wound site, the method comprising administering to the wound site an effective amount of the mixed-metal chalcogenide of the subject invention, the hydrogel/hydrogel formulation of the subject invention, or the composition of the subject invention.

The wound in the subject may be any disruption or damage to the anatomical or functional integrity of tissues, including but not limited to skin, mucosal surfaces, or internal tissues. In certain embodiments, the wound may result from physical trauma (e.g., cuts, abrasions, punctures, burns, or surgical incisions), pathological processes (e.g., infections, ulcers, or chronic inflammation), or external interventions. In certain embodiments, the wound can be acute or chronic, open or closed, superficial or deep, and may vary in size, cause, and healing progression. In certain embodiments, the wound may be associated or not associated with at least one of microbial infection, delayed healing, and impaired tissue regeneration.

Administration of the mixed-metal chalcogenide, the hydrogel/hydrogel formulation, or the composition of the subject invention may be selected and/or optimized based on factors such as the type of microbial pathogen, the site of infection, and the desired therapeutic effect. In specific embodiments, administering to the wound an effective amount of the mixed-metal chalcogenide, the hydrogel/hydrogel formulation or the composition of the subject invention may comprise introducing or delivering the mixed-metal chalcogenide, the hydrogel/hydrogel formulation, or the composition to the wound via any pharmaceutically acceptable route, including, but not limited to, topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites). In specific embodiments, the method may comprise injecting the mixed-metal chalcogenide, the hydrogel/hydrogel formulation, or the composition into or onto the wound.

In certain embodiments, the hydrogel/hydrogel formulation of the subject invention having thermoresponsive and injectable properties converts from a liquid form in ambient temperature or lower to solid hydrogel when reaching a desired temperature, for example, body temperature. Thus, upon administering or applying the injectable hydrogel/hydrogel formulation or the composition comprising the injectable hydrogel/hydrogel formulation to a wound, the injectable hydrogel/hydrogel formulation solidifies and serves as a wet wound dressing for infection control and enhanced healing as well as controlled release of any agents encapsulated in the polymeric matrix network of the hydrogel.

In certain embodiments, the method of the subject invention may utilize one or more ROS-generating agents to activate or enhance the catalytic activity of the mixed-metal chalcogenide nanozymes, the hydrogel/hydrogel formulation, or the compositions of the subject invention, particularly, their POD-like behavior.

Advantageously, the mixed-metal chalcogenide, the hydrogel/hydrogel formulation. or the composition of the subject invention exhibits POD-like activity in the presence of one or more ROS-generating agents, and exhibits a photothermal effect upon irradiation, such as near-infrared (NIR) light. Both the POD-like catalytic activity and the photothermal property contribute independently or synergistically to the inhibition and/or killing of microbial pathogens, including fungi and bacteria, thereby facilitating or accelerating wound healing.

In certain embodiments, the method of the subject invention comprises, before, after, or simultaneously with the administering step, treating the wound with one or more ROS-generating agents and/or exposing the wound to NIR irradiation. These treatments may be selected and/or optimized based on factors such as the type of the wound, site of the wound, status of the infection, and the desired therapeutic effect.

In specific embodiments, treating the wound with one or more ROS-generating agents comprises introducing or delivering the agent(s) to the wound via any pharmaceutically acceptable route, including but not limited to topical application, injection (such as subcutaneous, intramuscular, intraarticular, intraperitoneal, or intratumoral injection), implantation, oral administration, rectal or vaginal administration, or applied directly to target sites (such as mucosal surfaces or wound sites).

In certain embodiments, the method of the subject invention may comprise applying NIR irradiation to at least a portion of the wound for a period of time, such as about 10 minutes, to induce photothermal activity of the injectable hydrogel/hydrogel formulation, prevent microbial infections, and enhance microbial killing. In certain embodiments, the method of the subject invention may comprise repeating cycles of NIR irradiation and passive cooling, for example, for 3 to 5 cycles, to verify the reproducibility and sustained efficacy of the photothermal effect.

In certain embodiments, the method of the subject invention may comprise, in the presence of one or more ROS-generating agents and/or under NIR irradiation, administering to the wound an effective amount of the mixed-metal chalcogenide of the subject invention, the injectable hydrogel/hydrogel formulation of the subject invention or the composition of the subject invention.

In certain embodiments, the method of the subject invention may further comprise, before, after, or simultaneously with the administering step, measuring the local or systemic temperature at the site of application (e.g., a wound site) to monitor photothermal activation of the mixed-metal chalcogenide, the injectable hydrogel/hydrogel formulation, or the composition of the subject invention, and to prevent overheating of surrounding tissues.

In certain embodiments, the method of the subject invention may further comprise, before, after, or simultaneously with the administering step, monitoring the wound healing progression, including wound closure and re-epithelialization, to assess the therapeutic effect of the mixed-metal chalcogenide, the injectable hydrogel/hydrogel formulation, or the composition in treating the wound.

In certain embodiments, the subject invention provides a photothermal therapy for treating infections in a subject, wherein the photothermal therapy utilizes the hydrogel/hydrogel formulation or composition comprising the hydrogel/hydrogel formulation of the subject invention to combat infections by administering to the subject an effective amount of the hydrogel/hydrogel formulation or composition comprising the hydrogel/hydrogel formulation of the subject invention to combat infections.

In specific embodiments, the hydrogel/hydrogel formulation further comprises an additional photothermal agent (e.g., gold nanoparticles, polydopamine, or graphene oxide) that converts NIR light into localized heat, enabling controlled release of encapsulated therapeutic agents (e.g., mixed-metal chalcogenides) and thermal eradication of bacteria.

In certain embodiments, the subject invention provides a photothermal therapy for promoting wound healing and/or tissue regeneration, wherein the photothermal therapy utilizes the hydrogel/hydrogel formulation or composition comprising the hydrogel/hydrogel formulation of the subject invention to combat infections by administering to a wound an effective amount of the hydrogel/hydrogel formulation or composition comprising the hydrogel/hydrogel formulation of the subject invention to combat infections.

In certain embodiments, the wound may be an internal wound or an external wound on the skin. In a specific embodiment, the wound is a skin ulcer. The skin ulcer may be located, for example, on the foot, hand, leg, arm, face, and/or torso.

In certain embodiments, the photothermal therapy of the subject invention also allows patients and healthcare providers to continuously monitor wounds and examine severity and chronicity for formulating effective wound management strategies and assessing therapeutic efficacy.

In certain embodiments, administering to the wound an effective amount of the hydrogel/hydrogel formulation or composition comprising the hydrogel/hydrogel formulation of the subject invention may comprise applying the hydrogel/hydrogel formulation or composition comprising the hydrogel/hydrogel formulation of the subject invention onto the wound, injecting the hydrogel/hydrogel formulation or composition comprising the hydrogel/hydrogel formulation of the subject invention in the wound, or embedding a solidified hydrogel/hydrogel formulation of the subject invention in the wound.

In certain embodiments, applying the hydrogel/hydrogel formulation or composition comprising the hydrogel/hydrogel formulation of the subject invention onto the wound comprises applying the hydrogel/hydrogel formulation or composition comprising the hydrogel/hydrogel formulation of the subject invention in a liquid form on the wound, or in a solid form on the wound.

In certain embodiments, the subject invention further provides a method for delivering one or more therapeutic agents to a wound, the method comprising administering to the wound an effective amount of the hydrogel/hydrogel formulation or composition comprising the hydrogel/hydrogel formulation of the subject invention, wherein the hydrogel/hydrogel formulation comprise one or more therapeutic agents encapsulated in the polymeric matrix of the thermosresponsive polymer and the matrix polymer, and wherein the one or more therapeutic agents are mixed-metal chalcogenides and optionally an additional therapeutic agent.

In certain embodiments, the subject invention provides methods of using the non-invasive, flexible, injectable hydrogel/hydrogel formulation as a wound dressing in the presence or absence of other wound care materials such as gauze, bandages, or dressings.

Definitions

To facilitate an understanding of the subject invention, a number of terms and phrases are defined below. The terminology used herein is used only for the purpose of describing particular embodiments of the subject invention and is not intended to be limiting in any way.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, and cats; live stocks such as horses, cattle, pigs, sheep, goats, and chickens; and other animals such as mice, rats, guinea pigs, and hamsters.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, a symptom of the disease or condition, or the risk of (or susceptibility to) the disease or condition.

As used herein, the term "effective amount" or "therapeutically effective amount" refers to the amount of the mixed-metal chalcogenide, and/or the thermo-responsive polymer, and/or the matrix polymer, optionally, in combination with one or more additional therapeutic agents, described herein that is sufficient to effect its intended activity, and/or to effect treatment of the intended disease. The therapeutically effective amount may vary depending upon the intended application, the subject, and the disease being treated, e.g., the weight and age of the subject, the severity of the disease, the manner of administration and the like, which can readily be determined by one of ordinary skill in the art. The specific dose will vary depending on, for example, the particular dosing regimen to be followed, whether it is administered in combination with other compounds, timing of administration, the tissue to which it is administered, and the physical delivery system in which it is carried.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0 to 10%, 0 to 5%, or up to 1% of a given value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

Ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

The term "and/or" as used herein refers to and encompasses any and all possible combinations of one or more of the associated listed items. For example, the phrase "A, B, and/or C" includes A alone, B alone, C alone, the combination of A and B, the combination of A and C, the combination of B and C, and the combination of A, B, and C. Also, the term "or" is used in its inclusive sense (and not in its exclusive sense) so that when used, for example, to connect a list of items, the term "or" means one, some, or all of the items in the list. Conjunctive language such as the phrase "at least one of X, Y, and Z," unless specifically stated otherwise, is otherwise understood with the context as used in general to convey that an item, term, etc. may be either X, Y, or Z; X and Y; X and Z; Y and Z; or X, Y, and Z (i.e., any combination of X, Y, and Z).

As used herein, the term "peroxidase-like (POD-like) catalytic activity" or "peroxidase-like (POD-like) activity" refers to the catalytic function of a material that mimics the enzymatic activity of natural peroxidase enzymes. Specifically, such activity involves catalyzing the oxidation of a substrate in the presence of hydrogen peroxide ($H_2O_2$), typically resulting in the generation of reactive oxygen species (ROS), such as hydroxyl radicals (·OH), and the subsequent conversion of hydrogen peroxide into water ($H_2O$).

As used herein, the term "photothermal property" refers to the inherent characteristic of a material to absorb electromagnetic radiation—typically in the near-infrared (NIR) or visible light range—and convert the absorbed light energy into thermal energy (heat). This property enables the material to produce localized heating upon light irradiation, which can be harnessed for various biomedical and therapeutic applications, including antimicrobial treatment, photothermal therapy, and controlled release of therapeutic agents.

As used herein, the term "Near-Infrared (NIR) irradiation" refers to the exposure of a substance, composition, or biological sample to electromagnetic radiation within the near-infrared region of the light spectrum, typically encompassing wavelengths from approximately 700 nm to 1400 nm. In certain embodiments, NIR irradiation may be applied using lasers or LEDs at specific wavelengths (e.g., 808 nm) to induce photothermal effects or activate photosensitive compounds. NIR light possesses relatively deep tissue penetration and low phototoxicity compared to ultraviolet or visible light, making it particularly advantageous for biomedical applications such as photothermal therapy, photoactivation of therapeutic agents, or non-invasive imaging. In the context of the present disclosure, NIR irradiation may be used to activate the photothermal properties of mixed-metal chalcogenide nanozymes, leading to localized temperature elevation that contributes to the inhibition or killing of microbial pathogens.

Throughout this application, where publications are referenced, the disclosures of these publications in their entireties are hereby referred to in this application to more fully describe the state of the art to which this invention pertains.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Materials and Methods

Materials

Hydrochloric acid (HCl, 37%), ammonium perrhenate (VII) ($NH_4ReO_4$, >99%), thiourea (99%), hydroxylamine hydrochloride ($NH_2OH \cdot HCl$, >99%), sodium hydroxide (NaOH), glutaraldehyde (50%), ammonium orthomolybdate (VII) ($(NH_4)_2MoO_4$, >99%), and ethanol (200 proof, 100% by volume) were purchased from ThermoFisher Scientific (Waltham, MA). Propidium iodide (PI) was provided by Biotium (Fremont, CA). Sabouraud dextrose broth (SDB) and Sabouraud dextrose agar (SDA) were purchased from Research Products International (Mount Prospect, IL). Dulbecco's phosphate-buffered saline (PBS, pH 7.4) without magnesium and calcium was purchased from Biosynth Lonza Bioscience (Walkersville, MD). Stabilized 3,3',5,5'-tetramethylbenzidine (TMB) and $H_2O_2$ stock solutions and the IL-6 ELISA test kit were provided by R&D Systems Inc. (Minneapolis, MN). Cell Counting kit-8 (CCK-8) was purchased from GLPBIO Technology Inc. (Montclair, CA). Acridine orange (AO), and Gibco Dulbecco's Modified Eagle Medium (DMEM) were also purchased from ThermoFisher Scientific (Waltham, MA). *C. albicans* ATCC 10231 was purchased from Fisher Scientific.

PluronicF127 (PF127, 12.6 kDa molecular weight) was sourced from Sigma-Aldrich (St. Louis, MO, USA). Carboxymethyl chitosan (CMC) was obtained from Santa Cruz Biotechnology, Inc. (Santa Cruz, CA, USA). Ammonium perrhenate (VII) ($NH_4ReO_4$, >99%), thiourea (99%), hydroxylamine hydrochloride ($NH_2OH{\cdot}HCl$, >99%), ammonium orthomolybdate (VII) ($(NH_4)_2MoO_4$, >99%), acridine orange (AO), and Gibco Dulbecco's modified Eagle medium (DMEM) were procured from Thermo Fisher Scientific (Waltham, MA). Ethanol (200 proof, 100% by volume) was purchased from Decon Laboratories (King of Prussia, PA). Propidium iodide (PI) was purchased from Biotium (Fremont, CA). Dulbecco's phosphatebuffered saline (PBS, pH 7.4) without magnesium and calcium was acquired from Biosynth Lonza Bioscience (Walkersville, MD). The Cells Counting kit-8 (CCK-8) was purchased from GLPBIO Technology Inc. (Montclair, CA). LB Broth with agar (Lennox L agar) and LB Broth (Lennox L Broth) were obtained from Research Products International (Mount Prospect, IL). *S. aureus* (ATCC 29213, KWIK-STIK) and *E. coli* (ATCC3 35218, KWIK-STIK) were individually cultured and activated by inoculating the respective Kwik-Stik swab (Microbiologics, Inc.). Fetal bovine serum (FBS), penicillin-streptomycin (P/S), and non-essential amino acids (NEAA) were purchased from Thermo Fisher Scientific. Fibroblast NIH 3T3-GFP cells were purchased from MyBioSource (CAT number: MBS168783). ACS reagent-grade nanopure water was purchased from LabChem (Zelienople, PA). All chemicals, solvents, reagents, and cell culture materials were utilized as received without additional purification unless stated otherwise.

Characterization

Scanning electron microscopy (SEM) imaging of $Mo_xRe_{1-x}S_2$ NSs and the fungi under different treatments was conducted using a JEOL/JSM-F100 Schottky field emission scanning electron microscope (FE-SEM). X-ray fluorescence (XRF) measurements were carried out using a micro-XRF spectrometer (ATLAS M, IXRF Systems, Inc. Austin, Texas, USA). Ultraviolet-visible absorption spectroscopy was performed with a Thermo Scientific/BioMate 160 UV—visible spectrophotometer. Zeta potential and particle size analyses were carried out at room temperature using a Malvern/Zetasizer Nano-ZSZEN3600. X-ray diffraction (XRD) measurements were conducted using a Rigaku MiniFlex600 equipped with Cu Kα radiation (λ=1.5405 Å) operating at 40 kV and 30 mA. Raman spectroscopy was carried out using a WITec alpha300 R confocal Raman microscope equipped with a 532 nm laser. pH measurements were performed with a FE 150 pH meter. An EVOS M7000 System (Thermo Fisher) was used for confocal microscopy imaging. Thermal images were collected with a thermal imaging camera (Teledyne FLIR).

SEM imaging and elemental mapping of $Mo_{0.66}Re_{0.34}S_{1.85}$ NSs, the hydrogel, and *S. aureus* and *E. coli* after different treatments were performed with a JEOL JSM-7000 scanning electron microscope, equipped with electron-dispersive X-ray spectroscopy (EDX). Transmission electron microscopy (TEM) imaging was carried out with a JEOL JEM-2100Plus instrument. A Modulight ML6600 series laser platform equipped with an 808 nm NIR laser (ML6600-808-980-1470-0A1, Modulight Corporation, Finland) was used for photothermal treatment experiments. Hydrogel rheological properties were characterized using the MCR 72 (Modular Compact Rheometer) from Anton Paar. The thermogravimetric analysis (TGA) measurements were performed on a HITACHI simultaneous thermal analyzer (STA200, Hitachi, Japan) at a heating rate of 20° C./min from 30 to 600° C. in an $N_2$ atmosphere.

Synthesis of $Mo_xRe_{1-x}S_y$ Nanozymes

Five different compositions of the $Mo_xRe_{1-x}S_2$ materials were prepared via a hydrothermal synthesis with the following intended different compositions: $MoS_2$, $Mo_{0.25}Re_{0.75}S_2$, $Mo_{0.5}Re_{0.5}S_2$, $Mo_{0.75}Re_{0.25}S_2$, $Mo_{0.42}Re_{0.58}S_{1.94}$, $Mo_{0.66}Re_{0.34}S_{1.85}$, $Mo_{0.81}Re_{0.19}S_{1.76}$, and $ReS_2$.

In a typical experiment, predetermined amounts of ammonium orthomolybdate (VII) ($(NH_4)_2MoO_4$) and ammonium perrhenate-(VII) ($NH_4ReO_4$) were dissolved in 60 mL of deionized/nanopure water under stirring, totaling 1.2 mmol of Mo and Re metal precursors as per Table 1, at selected ratios of 0:4, 1:3, 2:2, 3:1, 4:0. Hydroxylamine hydrochloride (125.08 mg, 1.8 mmol) and thiourea (205.54 mg, 2.7 mmol) were then added to the mixture, and the mixture was stirred for 1 h. For each composition, the resulting solution was then transferred to an autoclave which was tightly sealed, introduced into a box furnace, and allowed to react for 24 h in a furnace at 230° C. After the reaction, the autoclave was cooled to room temperature, and the product was collected by centrifugation (8000 rpm for 15 min). To remove any unreacted precursors, the product was washed three times with deionized/nanopure water. The resulting $Mo_xRe_{1-x}S_y$ was collected by centrifugation and dried in a vacuum oven.

TABLE 1

Chemical Reagents for $Mo_xRe_{1-x}S_2$ Preparation.

| Intended Compositions | Actual Obtained Compositions | $Na_2MoO_4{\bullet}2H_2O$ (MW 241.96 g/mol) | $NH_4ReO_4$ (MW 268.24 g/mol) | $NH_2OH{\bullet}HCl$ (MW 69.49 g/mol) | Thiourea (MW 76.12 g/mol) | Actual mass (mg) |
|---|---|---|---|---|---|---|
| $ReS_2$ | $ReS_2$ | — | 1.2 mmol (321.89 mg) | | | 119.2 |
| $Mo_{0.25}Re_{0.75}S_2$ | $Mo_{0.42}Re_{0.58}S_{1.94}$ | 0.3 mmol (72.59 mg) | 0.9 mmol (241.42 mg) | | | 126.4 |
| $Mo_{0.5}Re_{0.5}S_2$ | $Mo_{0.66}Re_{0.34}S_{1.85}$ | 0.6 mmol (145.18 mg) | 0.6 mmol (160.94 mg) | 1.8 mmol (125.08 mg) | 2.7 mmol (205.54 mg) | 120.8 |
| $Mo_{0.75}Re_{0.25}S_2$ | $Mo_{0.81}Re_{0.19}S_{1.76}$ | 0.9 mmol (217.77 mg) | 0.3 mmol (80.47 mg) | | | 110.5 |
| $MoS_2$ | $MoS_2$ | 1.2 mmol (290.36 mg) | — | | | 120.0 |

All the synthesized $Mo_xRe_{1-x}S_y$ materials were to be tested in hydrogel preparation. As a representative example, upon synthesis, stock suspensions of $Mo_{0.66}Re_{0.34}S_{1.85}$ were prepared at a concentration of 1 mg/mL in nanopure water, followed by ultrasonication for 30 min to achieve a homogeneous dispersion solution, rendering the suspension suitable for subsequent preparation of the photothermal hydrogel.

Photothermal Properties of $Mo_xRe_{1-x}S_2$ Nanozymes

The suspensions of $Mo_xRe_{1-x}S_2$ at a 200 μg/mL concentration were prepared by sonication in nanopure water. The experiments were performed in 96 well plates; 200 μL of solution was added to each well. Each sample (well) was irradiated for 10 min with an 808 nm near-infrared laser (Roithner Lasertechnik GmbH/RLDH808-1200-5) at a power density of 1 W/cm$^2$. The temperature of the solution was recorded at 10 s intervals using a digital thermometer (Physitemp/TH-5) connected to a microprobe thermocouple. After 10 min of irradiation, the laser was turned off, and the temperature drop was measured in the same manner. The process was repeated for five cycles of heating and cooling to test the photothermal stability. Additionally, $Mo_xRe_{1-x}S_2$ suspensions at different concentrations (0, 50, 100, 200 μg/mL) were prepared in 200 μL volume in nanopure water, placed in 1.5 mL Eppendorf tubes (EP tubes), and treated in the same manner. Thermal images were captured at an interval of 2 min with a thermal camera. The photothermal conversion efficiency (η) was calculated based on previously reported methods.

Cell Viability Assay for Biocompatibility Testing

The HeLa cell line was purchased from Antibody Research Corporation (Saint Charles, MO, USA). The cells were cultured in DMEM, supplemented with 10% heat-inactivated fetal bovine serum, 0.1 g/L streptomycin sulfate, and 0.1 g/L penicillin G. They were incubated at 37° C. in a humidified atmosphere of 5% $CO_2$. The cell viability assay was performed using a Cell Counting Kit-8 (CCK-8 kit). CCK-8 utilizes a tetrazolium salt, WST-8, which is converted to the water-soluble WST-8 formazan. The amount of formazan produced is proportional to the number of viable cells and can be quantified by measuring the absorbance at 450 nm. Initially, HeLa cells were seeded into 96-well plates (Corning Costar, Corning, NY) at a density of $1.0\times10^3$ cells per well in 100 μL of medium to evaluate the biocompatibility of $Mo_xRe_{1-x}S_2$. After incubation for 24 h, cell viability was assessed using a CCK-8 assay with various concentrations of $Mo_xRe_{1-x}S_2$ (0-200 μg/mL). Subsequently, 10 μL of CCK-8 solution was added to each well, and the plates were incubated for an additional 2 h before absorbance measurement.

Culture and Preparation of *C. albicans*

In the subject invention, all of the tests of antifungal activity were evaluated against *C. albicans*. Both Sabouraud dextrose broth (SDB) and Sabouraud dextrose agar (SDA) media used in the subject invention were sterilized in an autoclave at 121° C. for 25 min. The strain of *C. albicans* was stored in SDB supplemented with 20% glycerol at −80° C. The glycerol stock containing the strain was thawed and revived on an SDA plate at 37° C. for 24 h. Next, a single colony was transferred using a sterile inoculation loop into a 15 mL sterile polypropylene round-bottom culture tube containing 5 mL of SDB and incubated in a shaking incubator at 37° C. and 180 rpm. After 12 h of incubation, the strains were centrifuged at 1000 rpm for 5 min and washed once with PBS, and the fungi were ready for immediate use.

POD-Like Activity of the Nanozymes

To quantify the catalytic efficiency and specificity of $Mo_xRe_{1-x}S_2$ toward the POD substrate, Michaelis-Menten kinetics of the catalytic process were further investigated. In the subject invention, the POD-like activity of the nanozymes was studied by varying the concentration of TMB or $H_2O_2$ while keeping the other conditions constant. Stock solutions of TMB and $H_2O_2$ were prepared at 1.66 M (0.4 g/L) and 0.2 M, respectively. As illustrated in Scheme 1, oxidation of TMB by a model peroxidase, horse radish peroxidase (HRP), in the presence of $H_2O_2$ leads first to the blue-colored TMB radical cation, followed by its further oxidation to the yellow-colored diimine. Lineweaver-Burk plots were generated to determine the Michaelis-Menten constant ($K_m$) for TMB and $H_2O_2$, respectively. A lower $K_m$ value indicates a higher affinity between the enzyme and the substrate.

Scheme 1. Oxidation of TMB Using $H_2O_2$

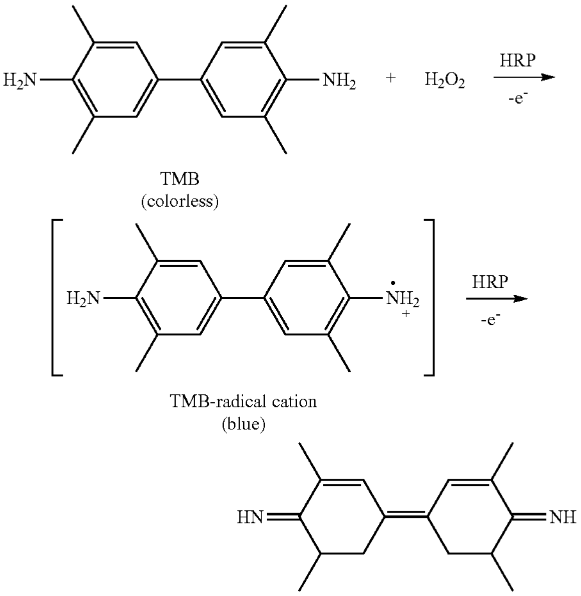

TMB (colorless)

TMB-radical cation (blue)

Diimine (yellow)

Antifungal Activity

The antifungal activity testing was conducted in 96-well plates as described above. An amount of 50 μL of fungal suspension ($1\times10^8$ colony-forming units (CFU) per mL) was added to each well, followed by the addition of 50 μL of $H_2O_2$ solution (3 mM). A stock solution of nanozyme was prepared at 1 mg/mL, and different amounts of $Mo_xRe_{1-x}S_2$ were dispensed into each well to reach the desired concentrations (7.5 μL for 0.025 mg/mL; 15 μL for 0.05 mg/mL, and 30 μL for 0.1 mg/mL), using PBS to adjust the final total volume to 300 μL. The antifungal activity was evaluated under the treatment of the nanozyme both alone and combined with laser irradiation at 808 nm. After the nanozyme exposure, the antifungal effect of $Mo_xRe_{1-x}S_2$ was evaluated using the spread plate method. An amount of 10 μL of fungal suspension from each 96-well plate was evenly spread on the surface of agar plates, and after that, the plates were placed in the 37° C. incubator for 24 h. The number of fungal colony-forming units was counted and compared to the control group. The experiments were conducted in a biosafety cabinet and repeated thrice. The fungi survival rate was calculated using Eq. 1.

$$\text{Viability } (\%) = \frac{\#\text{ of colonies formed in the ep group}}{\#\text{ of colonies formed in the control group}} \times 100 \quad \text{(Eq. 1)}$$

*C. albicans* Staining Test

Acridine orange (AO)/propidium iodide (PI) staining was used for the live and dead *C. albicans* staining. The protocol of the live/dead bacteria staining test with the AO/PI staining solution is described as follows. The concentration of the fungal stock suspension in the staining test was $1.0 \times 10^8$ $CFU \cdot mL^{-1}$. After treatment, 100 μL of a *C. albicans* suspension was centrifuged and resuspended in 0.85% NaCl. Then, the samples were stained with the prepared AO/PI solution at 37° C. in the dark for 1 h. Next, 5 μL of the stained mixture was placed onto a microscope cover glass (18 mm×18 mm), and then placed upside down on a microscope slide and sealed on all sides. A confocal fluorescence microscope was employed to capture images, with the green fluorescence signal at 488 nm indicating live cells and the red fluorescence signal at 561 nm indicating dead cells.

The Protocol of Live/Dead Bacteria Staining Test (AO/PI)

1. Dye stock solution:
   - a) 4 mM Acridine Orange (AO) (438.1 g/mol): 1.7524 mg+1 mL DMSO.
   - b) 16 mM Propidium Iodide (PI) (668.4 g/mol): 1.06944 mg+100 μL DMSO.
2. Dissolve completely, and store at 4° C.
3. Preparation of dye mixture:
   - 1) Warm the dye stock solution to room temperature and vortex to mix.
   - 2) Prepare 11 μL of 100× staining solution by combining 1 μL AO, 2 μL PI, and 8 μL 0.85% NaCl.
4. Take 100 μL fungal suspension into a new 96-well plate.
5. Add 1 μL of the dye mixture to 100 μL of fungal suspension.
6. Mix gently and incubate at 37° C. in the dark for 1 hour.
7. Transfer 5 μL of the sample to a slide, apply an 18×18 mm (thickness 0.13-0.17 mm) cover glass, and was sealed with nail polish.
8. Image the labeled samples by confocal fluorescence microscopy.

Imaging of *C. albicans* Morphology

For SEM imaging, each *C. albicans* specimen was prepared by the following method. The experiment was conducted in a 96-well plate. A fungal stock suspension was prepared at $1.0 \times 10^8$ $CFU \cdot mL^{-1}$. An amount of 100 μL of fungal suspension was added to each well, followed by the addition of 50 μL of $H_2O_2$ solution (3 mM), 30 μL of $Mo_xRe_{1-x}S_2$ solution (1 mg/mL), and 120 μL of PBS to adjust the final total volume to 300 μL. Next, the samples were subjected to irradiation at 808 nm. The group without $Mo_xRe_{1-x}S_2$ was a control to observe the morphology of the fungi. After treatment, the 96-well plate was placed in an incubator for 1 h. Next, the solutions from each well were transferred to 1.5 mL microcentrifuge tubes and centrifuged once (4000 rpm, 3 min) to remove the supernatant and redispersed into 200 μL of glutaraldehyde (2.5% in PBS) for fixation. After fixation for 24 h, the samples were dehydrated through an ethanol series, by submerging in 500 μL of ethanol solutions of progressively increasing concentrations (10, 30, 50, 70, 90, and 100%), with each step lasting 10 min. Subsequently, each fungal suspension was mixed with 15 μL of ethanol, and a 5 μL drop of this mixture was placed onto a 9 mm circular cover glass. These cover glasses were then dried overnight in an oven. The dried circular cover glass samples were affixed to the sample holder using tape and sputter-coated with gold (Au) to achieve a coating approximately 5 nm thick. Each sample was imaged by SEM at 10.0 kV and SEM EDX at 3 kV.

Optimal Ratio of PF127 and CMC in PF127/CMC/$Mo_xRe_{1-x}S_y$

A series of solutions was prepared using varying amounts of CMC and PF127 to a final volume of 8 mL in nanopure water, as shown in Table 2.

TABLE 2

CMC and PF127 Content in Hydrogel Composition

| ID | CMC (g) | PF127 (g) | total polymer solution volume (mL) | volume (mL) of nanoparticles suspension (1 mg/mL) |
|---|---|---|---|---|
| a | 0.1 | 1.9 | 8 | 2 |
| b | 0.2 | 1.8 | | |
| c | 0.3 | 1.7 | | |
| d | 0.4 | 1.6 | | |
| e | 0.5 | 1.5 | | |

Upon mixing, an amount of 2 mL of the selected $Mo_xRe_{1-x}$ $S_y$ nanosheets (1 mg/mL) was incorporated into the mixture at room temperature to form the photothermal hydrogel. Next, the coefficient was measured to identify the optimal ratio that facilitates gelation, as follows. Each hydrogel composition (10 mL each) was added to a glass vial, which was capped and stirred continuously in a water bath at 30° C. The gelation time was recorded as the time when the stir bar came to a stop.

Example of PF127/CMC/$Mo_xRe_{1-x}S_y$ Photothermal Hydrogel Preparation

Based on the optimal ratio of PF127 and CMC as identified using gelation time, photothermal hydrogels composed of PF127/CMC/$Mo_xRe_{1-x}S_y$ were formulated using the following procedure: 1.7 g of PF127 and 0.3 g of CMC (Table 2, entry (c)) were dissolved in water with thorough mixing, to reach a total of volume of 8 mL solution. Subsequently, an amount of 2 mL of $Mo_xRe_{1-x}S_y$ suspension (from a 1.0 mg/mL stock solution) was added, and the mixture was further stirred to ensure homogeneity. The total volume for each vial was 10 mL, resulting in a final nanomaterial concentration of 0.02% by weight and a final polymer concentration of 20% by weight. For comparison, PF127/CMC hydrogels were prepared at the same composition without incorporating the $Mo_xRe_{1-x}S_y$ suspension.

Example of PF127/CMC/$Mo_xRe_{1-x}S_y$ Photothermal Hydrogel Preparation in Cell Culture Media To conduct cell migration experiments in cell culture, the hydrogels were prepared following the same procedure as previously described, using cell culture medium instead of nanopure water as solvent. The cell culture medium is complete DMEM prepared using Gibco Dulbecco's modified Eagle medium (DMEM) supplemented with 10% FBS, 5% P/S, and 5% NEAA.

Rheology Evaluation

Hydrogels were introduced between two parallel plates with a 0.5 mm gap. Temperature sweep tests were conducted at a fixed angular frequency of 1.0 rad/s and a deformation amplitude of 1.0%. The tests covered a temperature range from 20 to 35° C., at a 1° C. per minute heating rate. The variation in storage modulus (G') and loss modulus (G") was analyzed to determine the sol-gel transition temperature of the composite hydrogel (identified as the temperature at which the G' and G" curves intersect).

Contact Angle Measurements

The hydrophilicity of the PF127/CMC and PF127/CMC/$Mo_{0.66}Re_{0.34}S_{1.85}$ hydrogels was evaluated through contact angle measurements performed using an Ossila Contact Angle Goniometer equipped with contact angle software. A 10 μL water droplet was gently placed onto the surface of the hydrogel (200 μL), and the contact angles were measured at two distinct temperatures (25 and 30° C.).

Shore Hardness Test

Materials' hardness values were measured using a Digital Shore OO Durometer (HFBTE, USA), with results reported in Shore OO units ranging from 0 to 100. Lower Shore OO values correspond to softer materials.

Photothermal Performance $Mo_xRe_{1-x}S_y$ nanosheets were reported to display high photothermal efficiency in water at various pH values. The photothermal performance of PF127/CMC/$Mo_xRe_{1-x}S_y$ hydrogels was assessed as follows. 200 μL of hydrogel samples were put into wells in 96-well plates separately and irradiated with an 808 nm NIR laser (Modulight ML6600) at a power intensity of 0.6 W/cm$^2$. During a 10 min irradiation period, the sample temperature was recorded every 10 s using an infrared FLIR thermal camera. In addition, thermal imaging of the same amount of hydrogel using 1.5 mL Eppendorf tubes (EP tubes) instead of the well plate was performed using the same camera every 2 min. Nanopure water, as well as PF127/CMC hydrogel without nanosheets, were evaluated as control groups. Furthermore, to assess the photothermal stability of the hydrogel, a total of five on-off laser cycles were conducted. Each cycle comprised 10 min of laser irradiation, followed by monitoring the cooling duration until the hydrogel returned to its initial temperature. Temperature measurements were recorded at 10 s intervals throughout the five cycles. The photothermal conversion efficiency (η) of PF127/CMC/$Mo_xRe_{1-x}S_y$ was then evaluated and calculated using Eq. 2. Subsequently, the hydrogel exhibiting the highest temperature was selected for further studies.

$$\eta = \frac{hA(\Delta T_{max,mix} - \Delta T_{max,H_2O})}{I(1 - 10^{-A_{808}})} \quad \text{(Eq. 2)}$$

where A is the surface area of the container, h is the heat transfer coefficient, $\Delta T_{max,mix}$ and $\Delta T_{max,H_2O}$ are the temperature changes of the PF127/CMC/$Mo_xRe_{1-x}S_y$ hydrogel and solvent (nanopure water), respectively, at the maximum steady-state temperature, I is the laser power, and $A_\lambda$ is the absorbance of PF127/CMC/$Mo_xRe_{1-x}S_y$ hydrogel at 808 nm. More details of the calculations of the photothermal conversion efficiency (η) of the PF127/CMC/$Mo_{0.66}Re_{0.34}S_{1.85}$ hydrogel are shown as follows.

Calculation of the Photothermal Conversion Efficiency (η) for the PF127/CMC/$Mo_{0.66}Re_{0.34}S_{1.85}$ Hydrogel The equation below (Eq. 2) represents the calculation for the photothermal efficiency, where hA can be determined from equation (Eq. 3):

$$\tau_s = \frac{\sum_i m_i C_{p,i}}{hA} \quad \text{(Eq. 3)}$$

where is the $m_i$ mass of the solution containing the photoactive material, which is $2\times10^{-4}$ kg, and $C_{p,i}$ is the specific heat capacity of the solution, which equals $4.2\times10^3$ J·(kg·° C.)$^{-1}$. $\tau_s$ is the linear fitted slope of time versus −ln(θ) from equation (Eq. 4):

$$t = -\tau_s \ln(\theta) \quad \text{(Eq. 4)}$$

where t is the time and θ is a dimensionless parameter, which is defined as the ratio of ΔT and $\Delta T_{max}$:

$$\theta = \frac{\Delta T}{\Delta T_{max}} \quad \text{(Eq. 5)}$$

$$\Delta T = T\_T_{Surr} \quad \text{(Eq. 6)}$$

$$\Delta T_{max} = T_{max} - T_{Surr} \quad \text{(Eq. 7)}$$

The $A_\lambda$ was obtained by averaging triplicate measurements.

Substituting $m_i=2\times10^{-4}$ kg, $C_{p,i}=4.2\times10^3$ J/kg·° C., I=0.6 W, $\Delta T_{max,H_2O}$=4.1° C., $\Delta T_{max}$, PF127/CMC/$Mo_{0.66}Re_{0.34}S_{1.85}$ hydrogel=31.4° C., $\tau_s$=240.21, the calculated photothermal conversion efficiency (η) of the PF127/CMC/$Mo_{0.66}Re_{0.34}S_{1.85}$ hydrogel was 23.4% (FIG. 1).

In Vitro Biocompatibility Assay

Mouse embryonic fibroblast cells, NIH 3T3-GFP cells, were used to evaluate the biocompatibility of hydrogels. Extract dilution methods were used to perform in vitro biocompatibility tests of the hydrogels. To prepare the hydrogel extracts, 1 g of UV-sterilized hydrogel was added to 40 mL of complete DMEM medium (supplemented with 10% FBS, 5% P/S, and 5% NEAA) and incubated for 48 h. After incubation, the hydrogel extracts were obtained at different concentrations of 0%, 25%, 50%, 75%, and 100% by diluting with the complete DMEM medium. NIH 3T3-GFP cells were seeded at a density of $8\times10^3$ cells per well in 96-well plates and incubated for 24 h to allow them to attach. The culture medium was then replaced with the prepared hydrogel extracts corresponding to different concentrations followed by incubation for an additional 24 h. Then the extracts were removed, and the cells were rinsed with PBS. Subsequently, 100 μL of a mixture of fresh complete medium and CCK-8 assay kit (10%, v/v) was added to each well. Following 2 h incubation, optical density was measured at 450 nm using a Synergy H1 Hybrid Reader (BioTek). The experimental group consisted of cells cultured with hydrogels, while the control group included cells cultured without hydrogels. The blank control was represented by the medium alone, supplemented with CCK-8. Each treatment was performed in triplicate. Cell viability (%) was assessed using the following Eq. 8:

$$\text{cell viability (\%)} = \frac{OD_{test} - OD_{blank}}{OD_{control} - OD_{blank}} \times 100\% \quad \text{(Eq. 8)}$$

In Vitro Wound Scratch Assay

This assay represents a wound model. NIH 3T3-GFP cells were seeded into a 24-well plate at a density of 50,000 cells per well in the full DMEM. After overnight incubation to ensure cell adhesion, the cells reached approximately 90% confluency. A scratch was created in the cell monolayer using a 100 μL pipet tip, followed by washing with PBS to remove detached and dead cells. To evaluate the ability of the hydrogel formulations to promote cell migration as an indicator of wound healing, 1 mL of hydrogel prepared in DMEM medium was added to each well and the cell migration to the wound was observed under an optical microscope. The cells' migration was monitored by photographing at time 0 (immediately after the scratch), and 24, 48, 72, and 96 h after treatment. Wound contraction was quantified by measuring the distance between the wound boundaries at each time point using ImageJ software. The percentage of wound closure was calculated using the formula (Eq. 9):

$$\text{wound closure (\%)} = \frac{W_{d0} - W_{dt}}{W_{d0}} \times 100\% \qquad \text{(Eq. 9)}$$

$W_{d0}$ represents the initial wound distance, and $W_{dt}$ is the wound distance at time t. Each treatment condition was performed in triplicate to ensure reproducibility and reliability of the results.

In Vitro Bacterial-Killing Effect

The antibacterial effect of nanoparticles on *S. aureus* and *E. coli* was evaluated using the spread plate method. Both *S. aureus* and *E. coli* were cultured in liquid LB media and incubated at 37° C. with shaking at 150 rpm for 12 h. Following incubation, the bacterial cultures were centrifuged at 4000 rpm for 5 min. The resulting bacterial pellets were washed with PBS to remove the culture medium, centrifuged again, and resuspended in PBS (pH 7.4). Next, the PBS bacterial resuspension (*S. aureus* and *E. coli*) was added into 1.5 mL Eppendorf (EP) tubes in the following 12 groups: (1) control: *S. aureus*+PBS; (2) *S. aureus*+PF127/CMC hydrogel; (3) *S. aureus*+PF127/CMC/$Mo_{0.66}Re_{0.34}S_{1.85}$ hydrogel; (4) control: *S. aureus*+PBS+NIR 808 nm; (5) *S. aureus*+PF127/CMC hydrogel+NIR 808 nm; (6) *S. aureus*+PF127/CMC/$Mo_{0.66}Re_{0.34}S_{1.85}$ hydrogel+NIR 808 nm; (7) control: *E. coli*+PBS; (8) *E. coli*+PF127/CMC hydrogel; (9) *E. coli*+PF127/CMC/$Mo_{0.66}Re_{0.34}S_{1.85}$ hydrogel; (10) control: *E. coli*+PBS+NIR 808 nm; (11) *E. coli*+PF127/CMC hydrogel+NIR 808 nm; (12) *E. coli*+PF127/CMC/$Mo_{0.66}Re_{0.34}S_{1.85}$ hydrogel+NIR 808 nm. The groups of (4-6) and (10-12) were further exposed to a NIR laser (808 nm, 0.6 W/cm$^2$) for 10 min. Ten µL of bacteria suspension ($10^8$ cfu mL$^{-1}$) and the total volume of solution in each well was 200 µL. After incubation for 4 h, 100 µL of the bacterial suspension of groups (1-12) were diluted with PBS 1000-fold, spread on an agar culture plate, and incubated at 37° C. for 17 h to allow surviving bacteria to grow. The colony-forming units (cfu) were then determined, and each experiment was performed in triplicate. The bacterial survival rate was calculated using Eq. 10:

$$\text{viability (\%)} = \frac{\text{\# of colonies formed in the experimental group}}{\text{\# of colonies formed in the control group}} \times 100 \qquad \text{(Eq. 10)}$$

Bacterial Live/Dead Staining Assay

For the live/dead staining experiment, 20 µL of bacterial suspension (*S. aureus* and *E. coli*) at a concentration of 109 cfu·mL$^{-1}$ was added to each well of a 96-well plate, followed by the addition of 200 µL hydrogel. After 10 min of irradiation with an 808 nm near-infrared laser, the samples were allowed to cool to room temperature, transitioning from the gel phase to the solution phase. The samples were transferred to new sterilized EP tubes separately, followed by the addition of 1 mL of PBS in each tube. The mixture was thoroughly mixed and centrifuged at 4000 rpm for 5 min. The resulting bacterial pellets were first washed with 0.85% NaCl solution and then dispersed in 20 µL of the same solution, mixing in 1 µL of staining solution containing 4.0 µM acridine orange (AO) and 8.0 µM propidium iodide (PI). The mixture was incubated at 37° C. in a dark environment for 1 h. Following staining, 5 µL of the prepared sample was placed onto an 18×18 mm cover glass. Fluorescence images were obtained using a confocal fluorescence microscope, with live bacteria (green fluorescence) and dead bacteria (red fluorescence) detected at excitation wavelengths of 488 and 561 nm, respectively.

Imaging of Bacterial Morphology

The nontreated bacterial morphology was observed using a control group that received no treatment, in the absence of both irradiation and hydrogel treatment. Each bacterial specimen was prepared for SEM imaging using a published procedure. 100 µL bacteria suspensions of *S. aureus* and *E. coli* ($10^8$ cfu·mL$^{-1}$) were washed with 900 µL of PBS and centrifuged at 4000 rpm for 3 min in individual EP tubes. For experimental groups, 200 µL PF127/CMC/$Mo_{0.66}Re_{0.34}S_{1.85}$ hydrogel was added to the well in a 96-well plate and irradiated with an 808 nm for 10 min. Following treatment, the 96-well plate was incubated at 37° C. for 4 h. After incubation, the solutions from each well were transferred to 1.5 mL EP tubes respectively, centrifuged at 4000 rpm for 3 min to remove the supernatant, and resuspended in 200 µL of 2.5% glutaraldehyde in PBS for fixation. The samples were fixed for 24 h, then sequentially dehydrated using 500 µL of ethanol solutions with increasing concentrations (10%, 30%, 50%, 70%, 90%, and 100%) for 10 min each. Next, 15 µL of each dehydrated bacterial suspension was resuspended in ethanol, deposited onto 9 mm circular cover glasses, and air-dried. The cover glasses were then affixed onto SEM holders with conductive adhesive tape and sputter-coated with gold to achieve a ~5 nm thick coating. Finally, the prepared samples were imaged using an SEM at an accelerating voltage of 15.0 kV.

Statistical Analysis

All data were organized into tables as mean±standard deviation (SD). Comparisons among the experimental groups were performed using Student's multiple t test, with $p<0.05$ (*), $p<0.01$ (), and $p<0.001$ (*) considered statistically significant.

Example 1—Nanomaterial Characterization

Nanoparticle Morphology

Figure 2A:
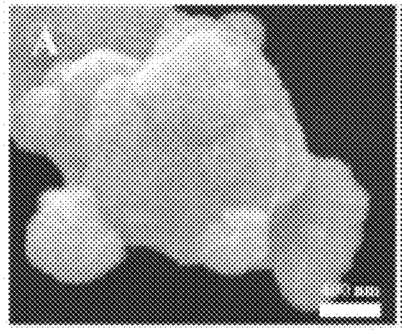
FIGS. 2A-2G show SEM images of $Mo_xRe_{1-x}S_2$ nanosheets (NSs) (A: $ReS_2$, and B: $Mo_{0.42}Re_{0.58}S_{1.94}$, C: $Mo_{0.66}Re_{0.34}S_{1.85}$, D: $Mo_{0.81}Re_{0.19}S_{1.76}$, and E: $MoS_2$) and elemental mapping analysis (F: $Mo_{0.66}Re_{0.34}S_{1.85}$, and G: $Mo_{0.81}Re_{0.19}S_{1.76}$).
Figure 2B:
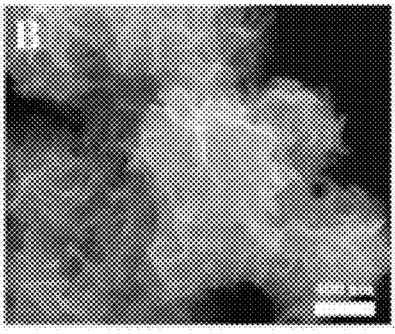
Figure 2C:
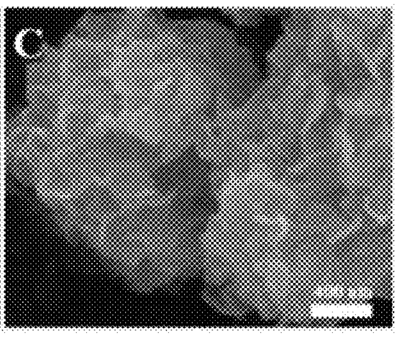
Figure 2D:
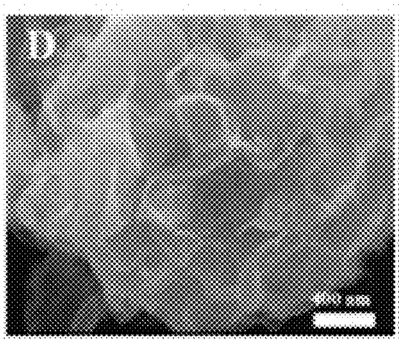
Figure 2E:
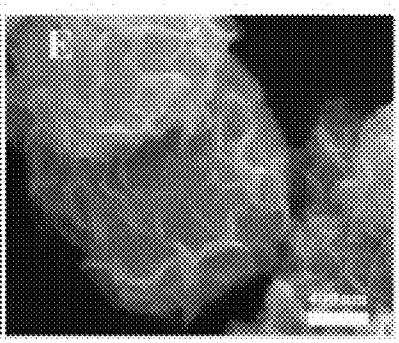
Figure 2F:
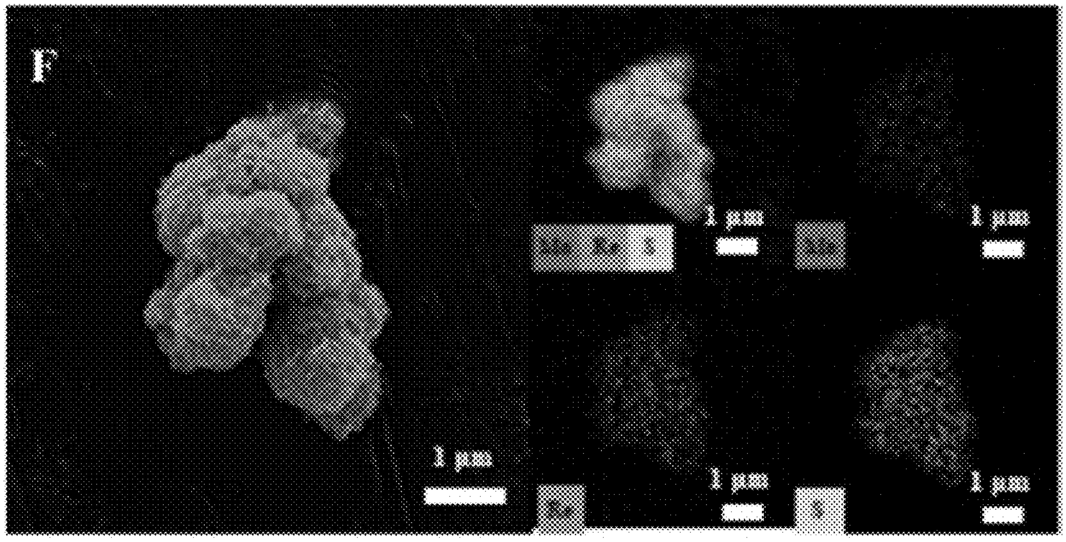
Figure 2G:
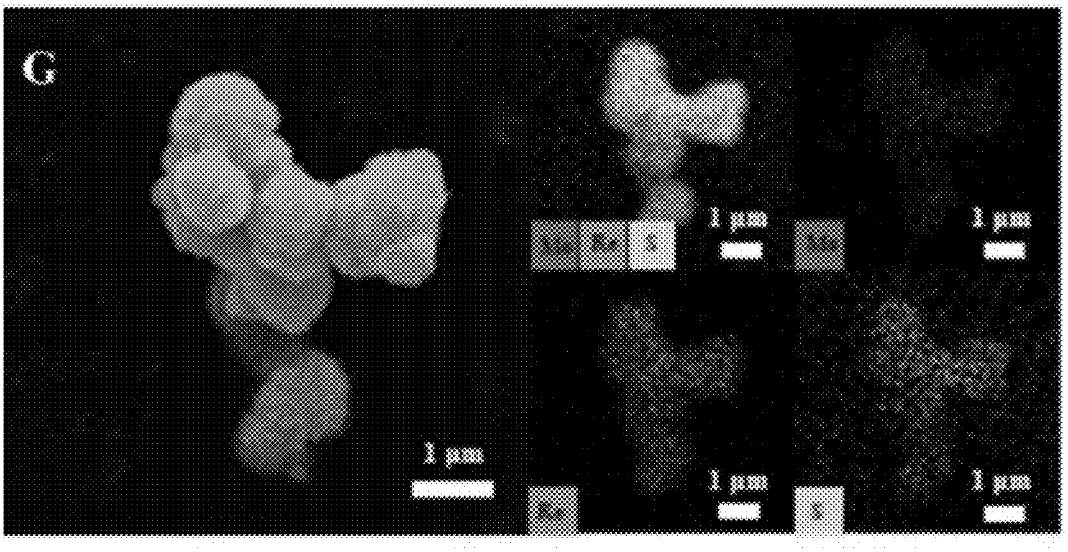
Figure 3A:
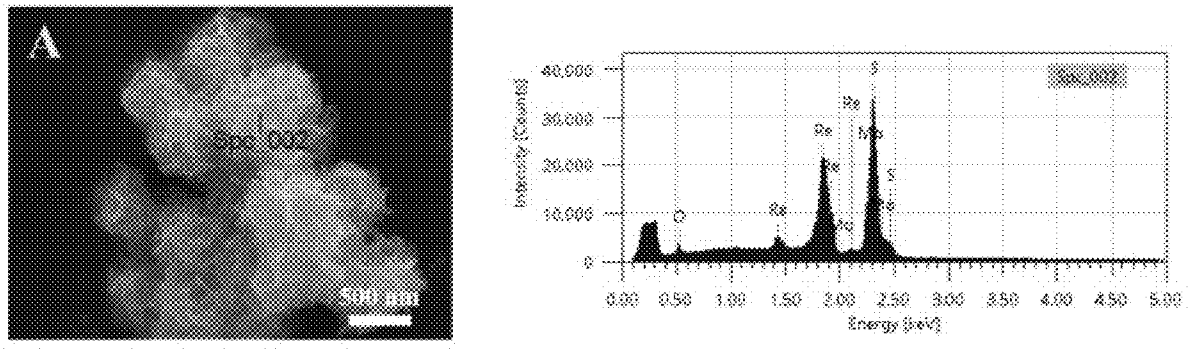
FIGS. 3A-3C show SEM EDX images of $Mo_xRe_{1-x}S_2$, A: $Mo_{0.42}Re_{0.58}S_{1.94}$, B: $Mo_{0.66}Re_{0.34}S_{1.85}$, and C: $Mo_{0.81}Re_{0.19}S_{1.76}$.
Figure 3B:
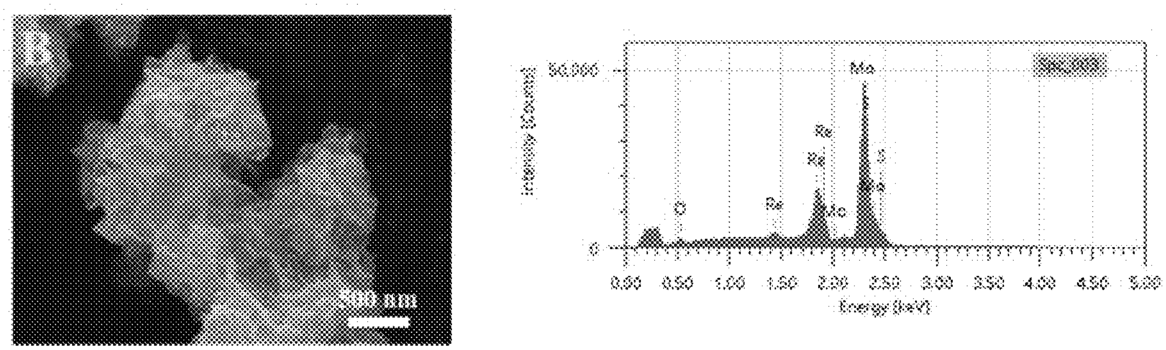
Figure 3C:
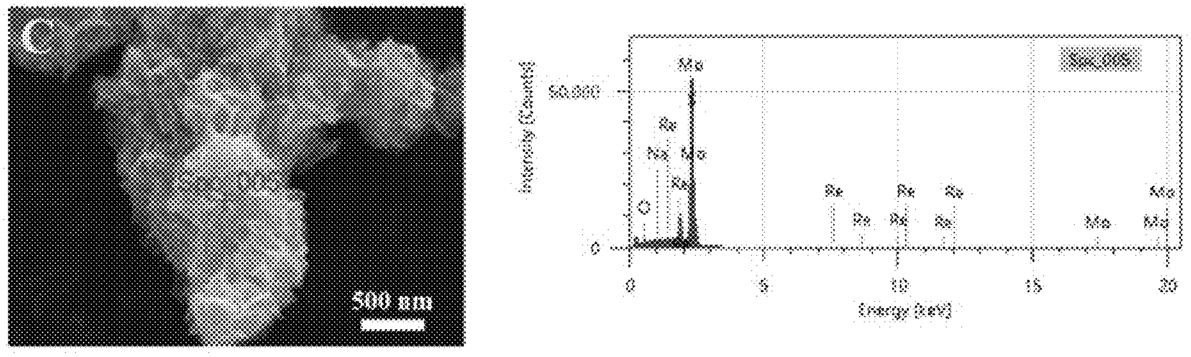

The surface morphology of the $Mo_xRe_{1-x}S_2$ NSs was observed by SEM (FIGS. 2A-E). The morphology of $Mo_xRe_{1-x}S_2$ is flower-like and consists of nanosheets self-assembled layer by layer. The SEM EDX analysis in FIG. 3 revealed that the intended compositions $Mo_{0.25}Re_{0.75}S_2$, $Mo_{0.5}Re_{0.5}S_2$, and $Mo_{0.75}Re_{0.25}S_2$ resulted in products with elemental compositions of $Mo_{0.42}Re_{0.58}S_{1.94}$, $Mo_{0.66}Re_{0.34}S_{1.85}$, and $Mo_{0.81}Re_{0.19}S_{1.76}$, respectively. The SEM elemental mapping results also revealed that the molybdenum (Mo), rhenium (Re), and sulfur(S) elements were uniformly distributed in two of the compositions, $Mo_{0.66}Re_{0.34}S_{1.85}$ and $Mo_{0.81}Re_{0.19}S_{1.76}$, as shown in FIGS. 2F and 2G, respectively.

Figure 4A:
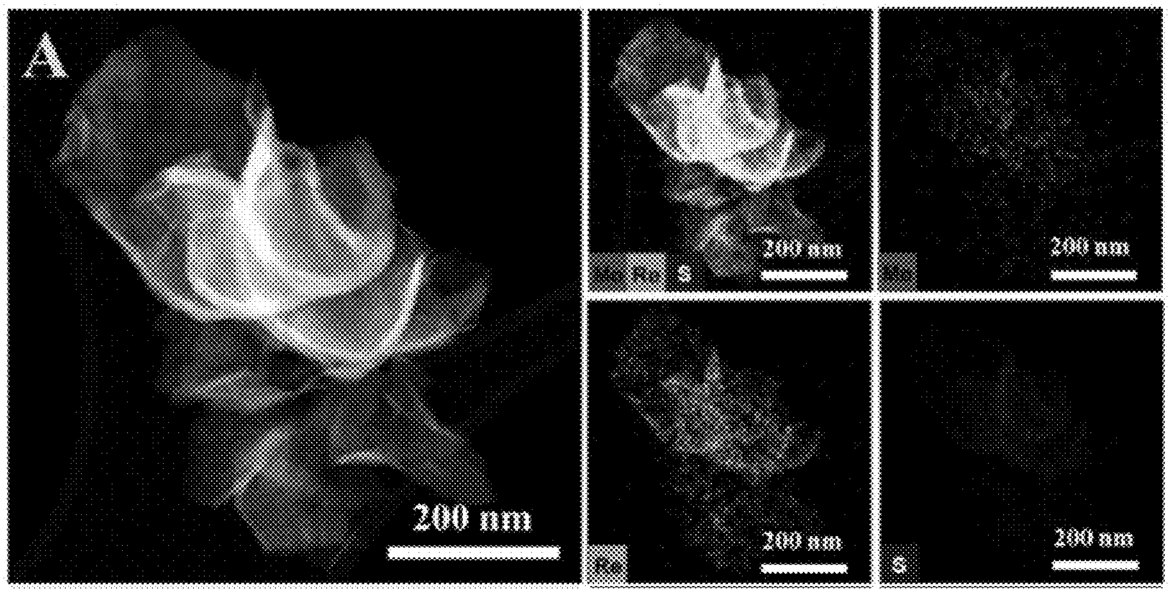
FIGS. 4A-4B show TEM and elemental mapping analysis of $Mo_{0.66}Re_{0.34}S_{1.85}$ (A) and $Mo_{0.81}Re_{0.19}S_{1.76}$ (B).
Figure 4B:
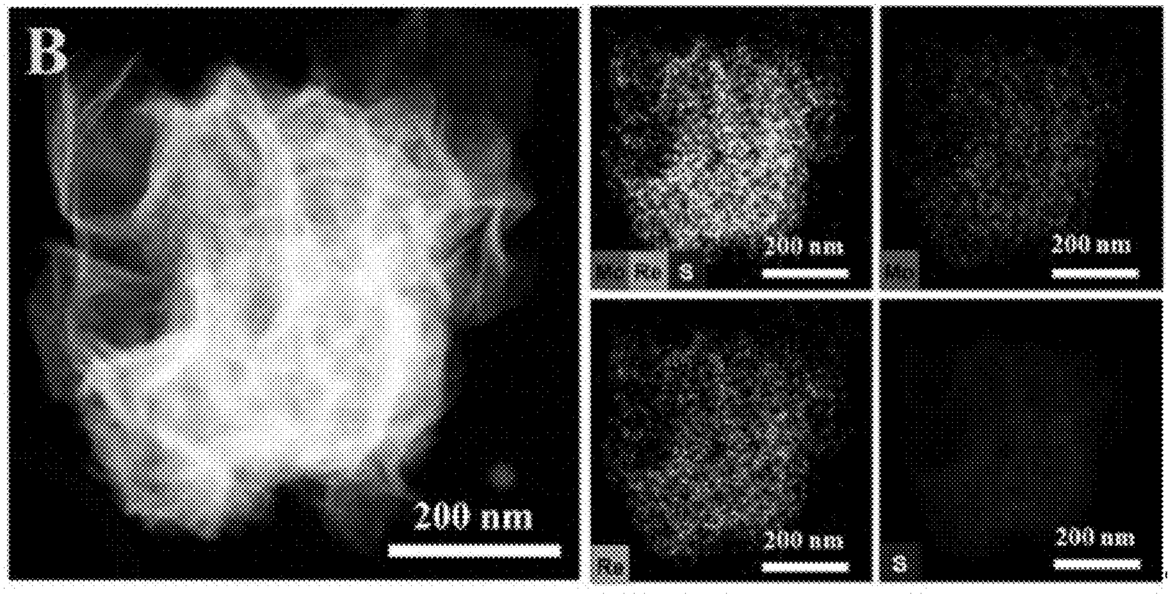

To further elucidate the morphologies and compositions of the $Mo_xRe_{1-x}S_2$ NSs, high magnification TEM imaging and TEM/EDS elemental mapping of $Mo_{0.66}Re_{0.34}S_{1.85}$ and $Mo_{0.81}Re_{0.19}S_{1.76}$ were conducted (FIGS. 4A and B, respectively). The TEM imaging confirmed that $Mo_{0.66}Re_{0.34}S_{1.85}$ and $Mo_{0.81}Re_{0.19}S_{1.76}$ exhibit a flower-like morphology formed of self-assembled nanosheets. High-resolution elemental mapping of $Mo_{0.66}Re_{0.34}S_{1.85}$ and $Mo_{0.81}Re_{0.19}S_{1.76}$ further validated the uniform distribution of Mo, Re, and S elements.

X-Ray Fluorescence (XRF)

Figure 5A:
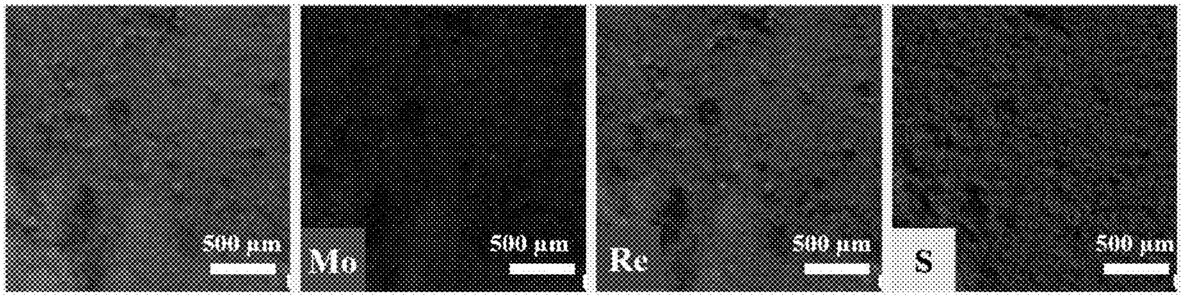
FIGS. 5A-5B show (A, B) X-ray fluorescence (XRF) elemental mapping of $Mo_{0.66}Re_{0.34}S_{1.85}$ and $Mo_{0.81}Re_{0.19}S_{1.76}$.
Figure 5B:
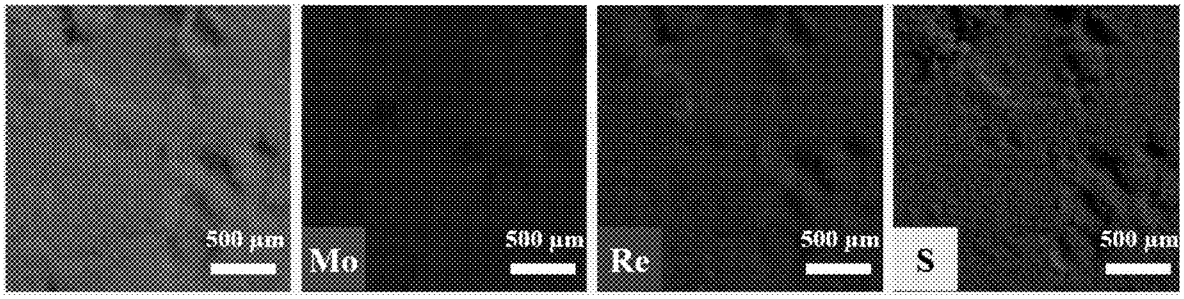

XRF was employed to further confirm the homogeneity of elemental composition of $Mo_{0.66}Re_{0.34}S_{1.85}$ and $Mo_{0.81}Re_{0.19}S_{1.76}$. As shown in FIG. 5, compared with the XRF spectrum of $Mo_{0.66}Re_{0.34}S_{1.85}$ and $Mo_{0.81}Re_{0.19}S_{1.76}$, the result reveals that the Mo content in $Mo_{0.66}Re_{0.34}S_{1.85}$ (34% in mass) is lower than that in $Mo_{0.81}Re_{0.19}S_{1.76}$ (45% in mass), further demonstrating that the elemental ratio of the final product varies with the different precursor contents during the reaction synthesis process. The elemental mapping analysis confirmed the different percentages of the alloyed metal sulfides. Different elemental ratios of the final product have been confirmed by scanning electron microscopy elemental analysis, transmission electron microscopy elemental analysis, and X-ray fluorescence.

X-Ray Powder Diffraction

Figure 6A:
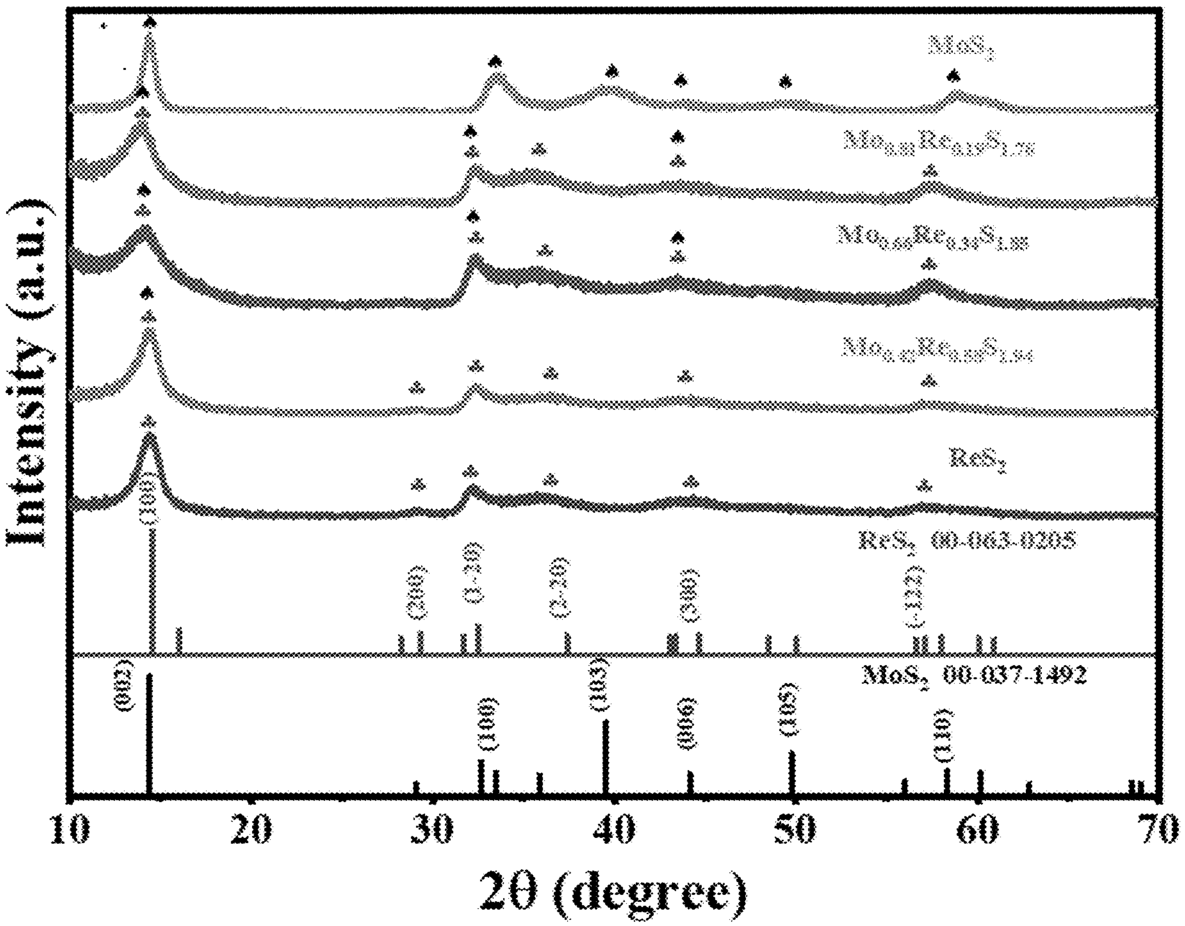
FIGS. 6A-6C show XRD pattern (A), Raman spectra (B), and absorption spectrum (C) of prepared $Mo_xRe_{1-x}S_2$ NSs.

The as-synthesized nanopowders of $Mo_xRe_{1-x}S_2$ were characterized by XRD to analyze the crystallographic changes with increasing the Mo content, as presented in FIG. 6A. The standard patterns of the pure $ReS_2$ (JCPDS No. 00-063-0205) and $MoS_2$ (JCPDS No. 00-037-1492) are also displayed in FIG. 6A.

Pure $MoS_2$ and $ReS_2$ display X-ray diffraction patterns that are quite similar due to their very similar crystal structure. As a result, the mixed-metal chalcogenides $Mo_xRe_{1-x}S_2$ (with $0<x<1$) show high similarity to the pure ones. Slight peak shifts could be attributed to the unit cell parameters expanding and the interplanar spacing increasing with increased Mo content.

Figure 7:
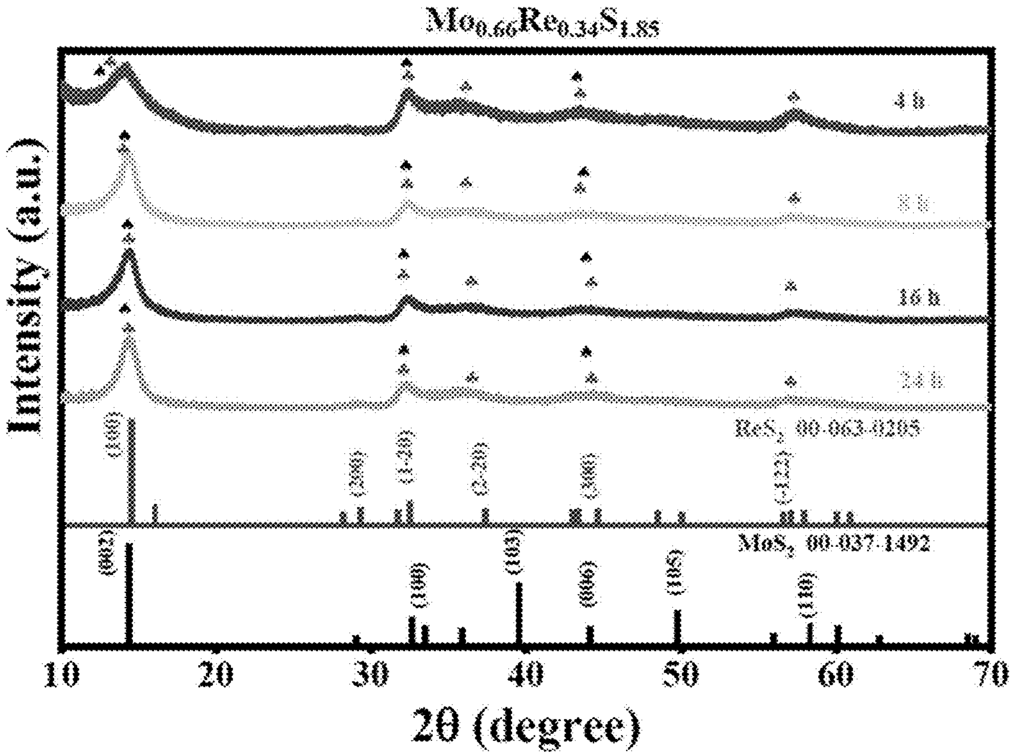
FIG. 7 shows XRD patterns of the synthesized $Mo_{0.66}Re_{0.34}S_{1.85}$ nanoenzyme with different reaction times (4~24 h) at 230° C. (red trefle symbols indicate $ReS_2$ and black spade symbols indicate $MoS_2$).
Figure 8A:
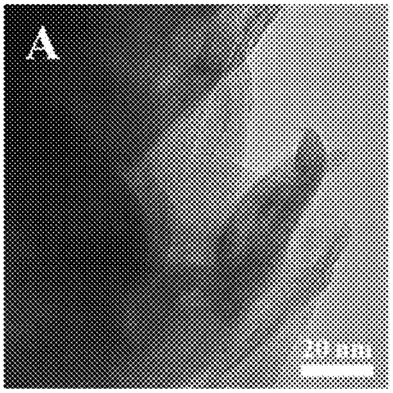
FIGS. 8A-8C show TEM images of the $Mo_{0.66}Re_{0.34}S_{1.85}$ nanoenzyme synthesized with different reaction times (A: 4 h; B: 8 h; C: 16 h) at 230° C.
Figure 8B:
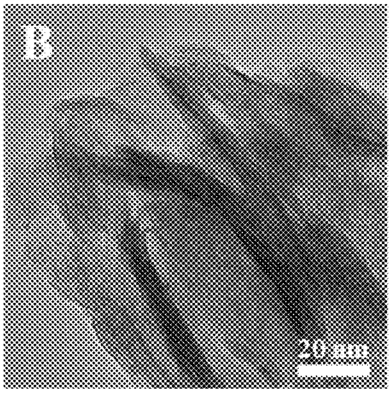
Figure 8C:
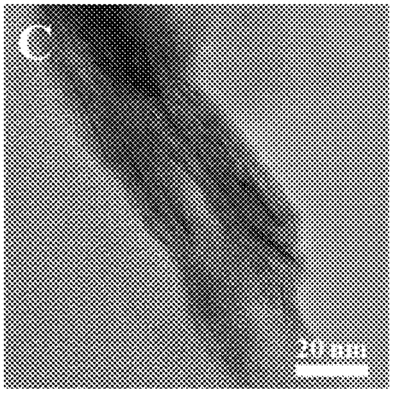
Figure 9A:
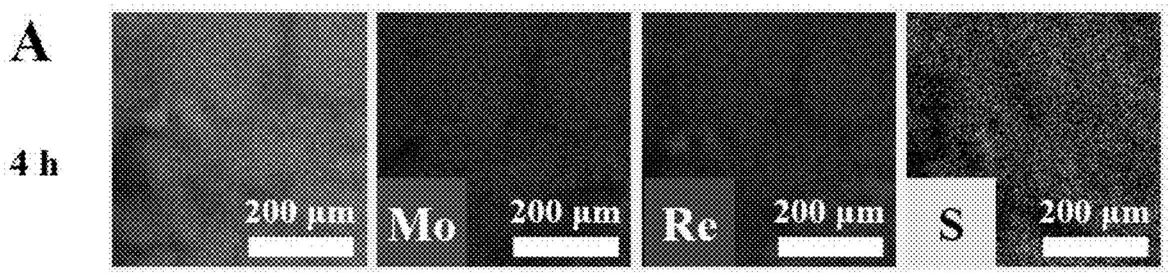
FIGS. 9A-9C show element mapping of X-ray fluorescence spectroscopy (XRF) (A, B and C) of different reaction times (4 h, 8 h, and 16 h).
Figure 9B:
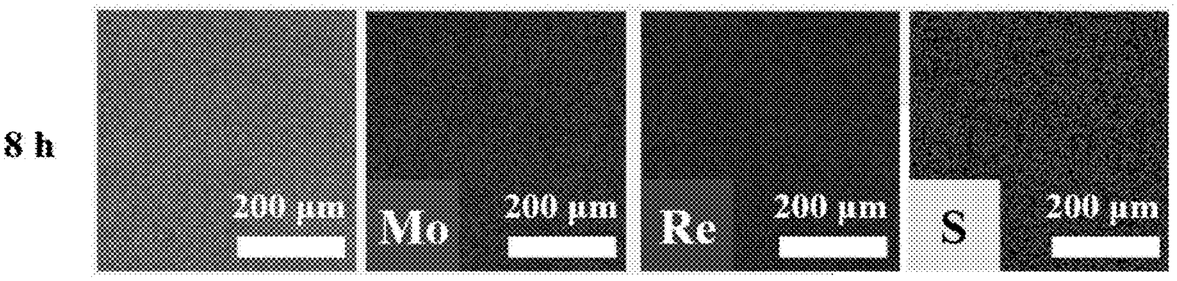
Figure 9C:
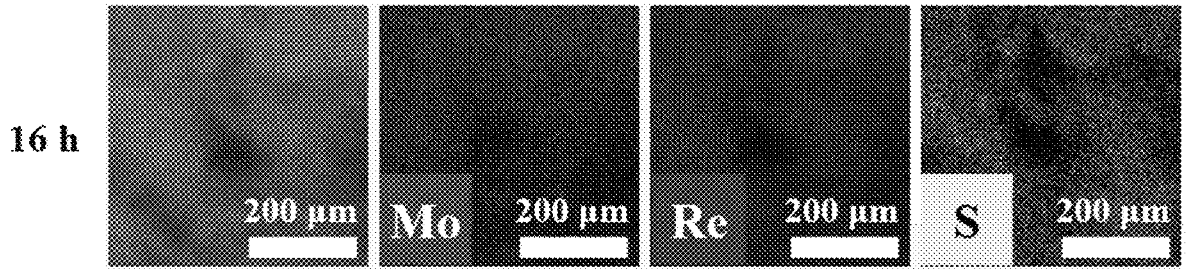

To explore the reaction mechanism underlying the formation of $Mo_xRe_{1-x}S_2$ and understand the correlation between final product composition and reaction time, different reaction times were explored for synthesizing $Mo_{0.66}Re_{0.34}S_{1.85}$. The products were analyzed by XRD (FIG. 7), TEM (FIG. 8), and XRF (FIG. 9). The stability of the synthesized $Mo_xRe_{1-x}S_2$ nanoenzyme in acidic conditions, in the pH range of 2.2-5 was evaluated by exposing $Mo_{0.66}Re_{0.34}S_{1.85}$ and $Mo_{0.81}Re_{0.19}S_{1.76}$ to solutions with different pH (2.2-5.0) for 16 h; the solution preparation is shown in Table 3.

TABLE 3

Preparation of solution with various pH

| pH value | $Na_2HPO_4$ (0.02M) | Citric acid (0.01M) | Total volume (mL) |
|---|---|---|---|
| 2.2 | 0.40 | 10.6 | 11 |
| 3.0 | 2.055 | 7.945 | 10 |
| 4.0 | 3.855 | 6.145 | 10 |
| 5.0 | 5.15 | 4.85 | 10 |
| 6.0 | 6.315 | 3.685 | 10 |
| **pH value** | **$Na_2HPO_4$ (0.2M)** | **$Na_2HPO_4$ (0.2M)** | **Total volume (mL)** |
| 7.0 | 3.8 | 6.2 | 10 |
| 8.0 | 0.53 | 9.47 | 10 |

Figure 10A:
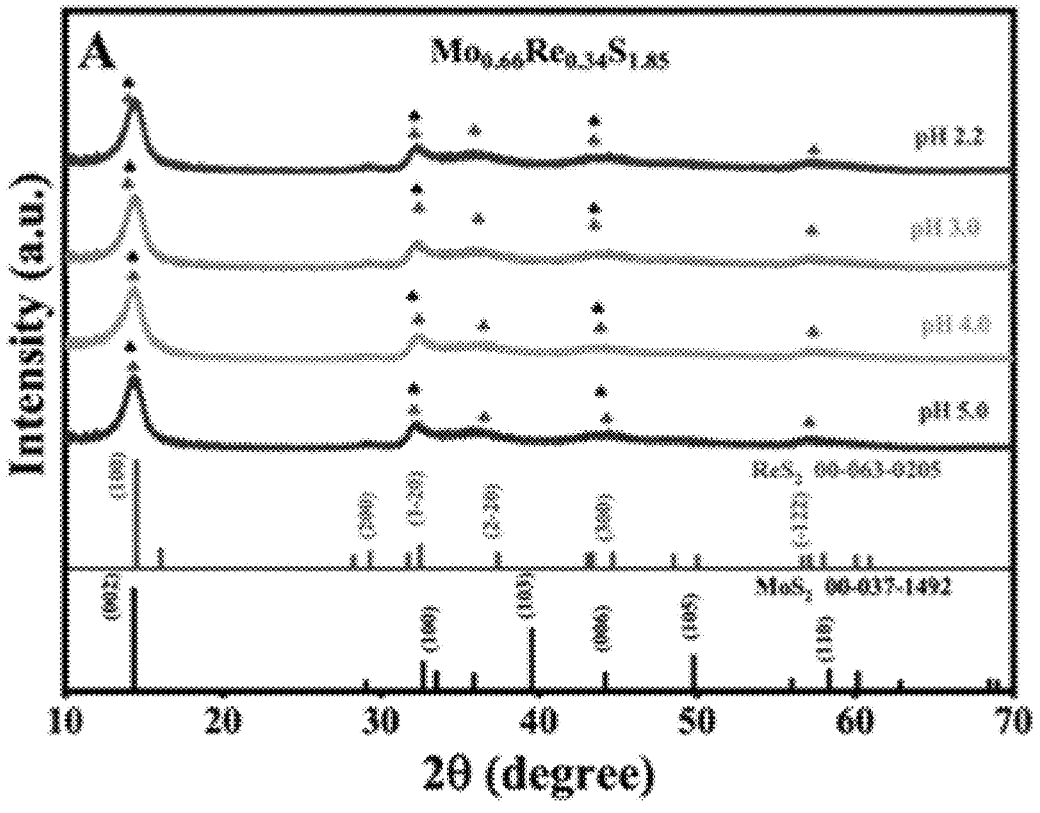
FIGS. 10A-10B show XRD patterns of $Mo_{0.66}Re_{0.34}S_{1.85}$ (A) and $Mo_{0.81}Re_{0.19}S_{1.76}$ (B) under different pH solutions (2.2-5) for 16 h.
Figure 10B:
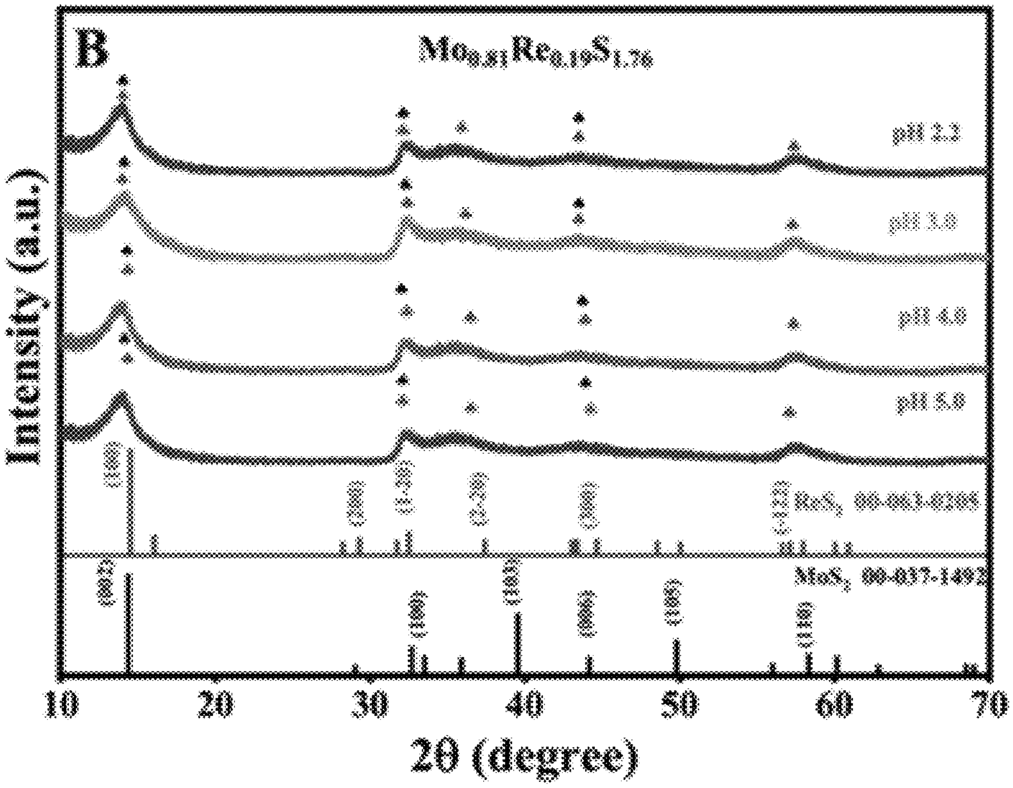

XRD patterns of $Mo_{0.66}Re_{0.34}S_{1.85}$ and $Mo_{0.81}Re_{0.19}S_{1.76}$ after exposure to solutions with different pH (2.2~5.0) for 16 h were recorded and are presented in FIG. 10. Notably, no discernible changes were observed in the XRD spectrum across the different pH conditions, indicating that the crystalline structures of both samples were unaffected by the acidic treatment, indicative of crystal lattice stability under the mildly acidic environment.

Raman Spectroscopy

Figure 6B:
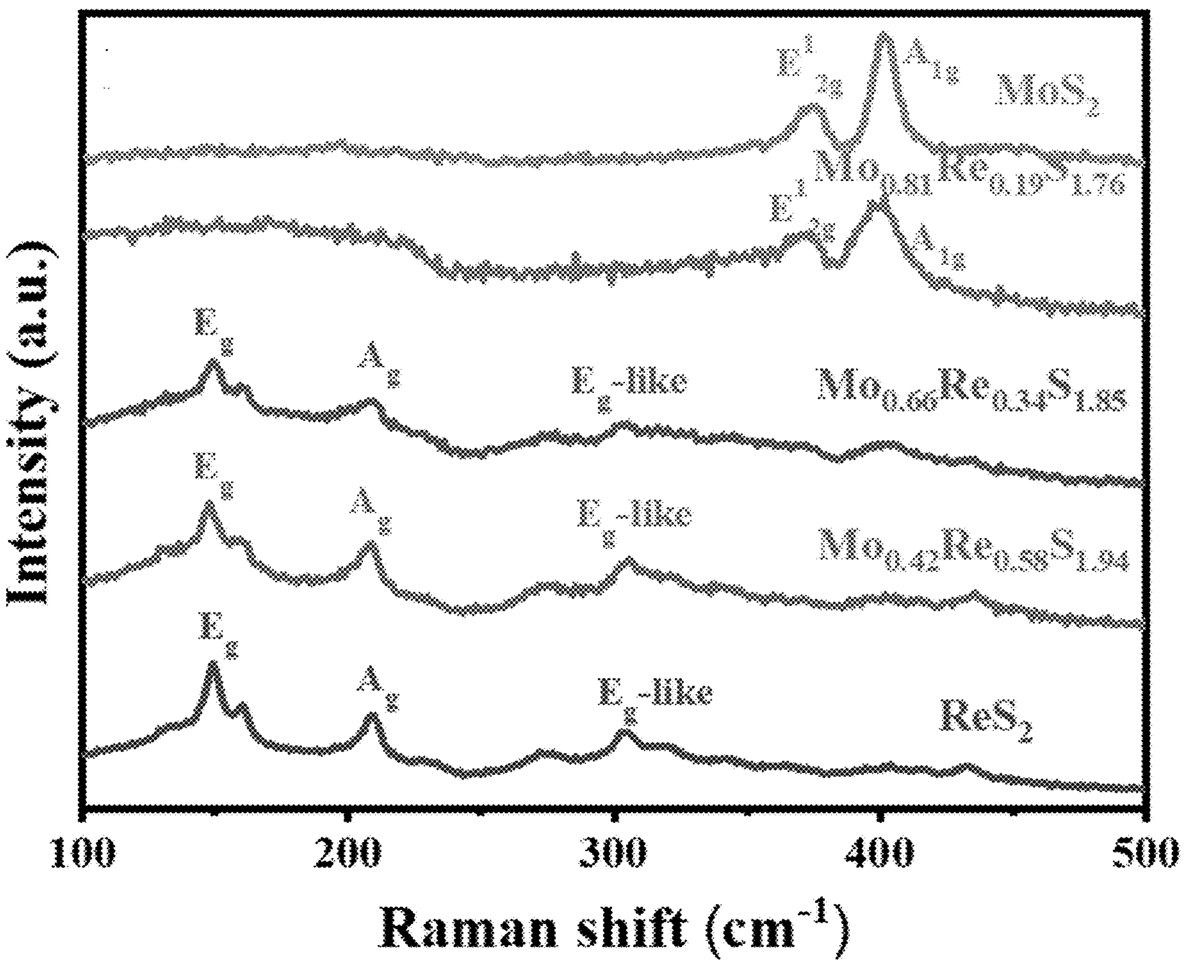

Raman spectra were collected to confirm the phase structure of the nanozymes. FIG. 6B presents the Raman spectra of $Mo_xRe_{1-x}S_2$ with increasing Mo content. $Mo_xRe_{1-x}S_2$ nanostructures exhibit main vibration modes in the range of 100-500 cm-1 corresponding to the $E_g$-like, $A_g$-like modes of $ReS_2$. Specifically, vibrational modes centered at 150.4 and 208.3 cm-1 correspond to the in-plane ($E_g$) and primarily out-of-plane ($A_g$-like) modes of $ReS_2$. As Mo content increased (x>0.65) two characteristic bands located at 374.4 and 402.2 $cm^{-1}$, which are attributed to the $E_{2g}$ and $A_{1g}$ modes of $MoS_2$, appeared. The $E_{2g}$ band is due to in-plane vibrations, and the $A_{1g}$ band is due to out-of-plane vibrations. Additionally, $E_g$ and second-order vibrational modes appear due to the low crystal symmetry. The differences in the magnitude of the shifts observed for both bands provide insight into the doping mechanism. Compared to the Raman spectrum of $MoS_2$, the $A_{1g}$ mode, which involved only the vibrational displacement of sulfur atoms, showed a slight shift from ca. 402.2 cm 1 to ca. 397.8 $cm^{-1}$ in $Mo_{0.81}Re_{0.19}S_{1.76}$. In contrast, the $E^1{}_{2g}$ mode, which involves the vibration of both metal and sulfur atoms within a layer, exhibits a significant shift from ca. 374.4 cm 1 to 369.9 $cm^{-1}$. This could be ascribed to the substitutional doping of the heavier Re atoms into the Mo layer. As the Re ratio increases in $Mo_xRe_{1-x}S_2$, the peaks of $E_g$, $A_g$, and $E_g$-like become sharper and more defined, like those of $ReS_2$.

Figure 6C:
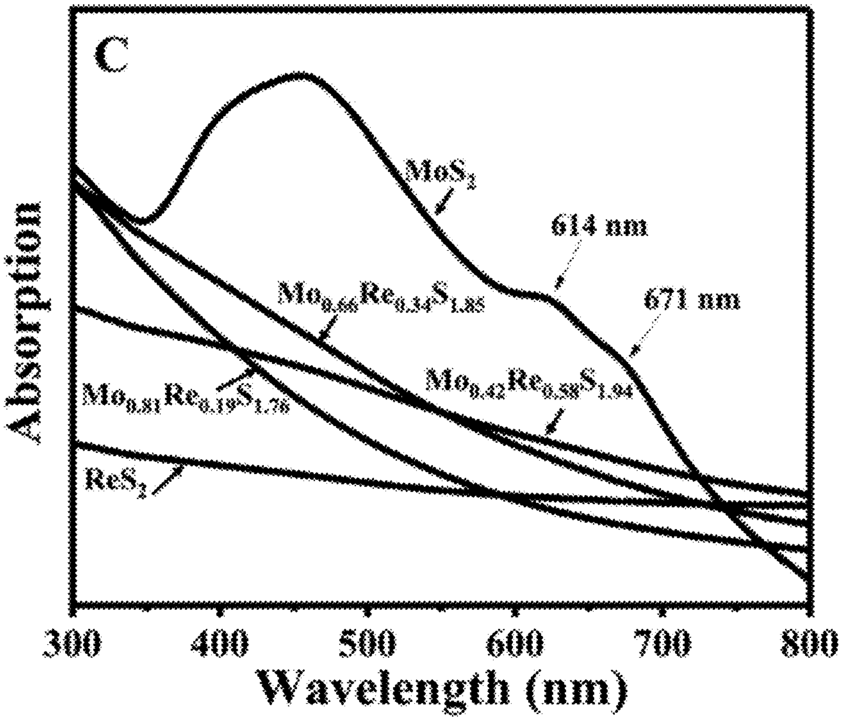

The absorption spectrum in FIG. 6C shows the variation in absorbance with increasing Mo content in $Mo_xRe_{1-x}S_2$. As shown in FIG. 6C, only $MoS_2$ exhibited an absorption peak at 671 nm corresponding to the direct band gap of 1.85 eV. The absorption intensity sharply decreased compared to that of $MoS_2$ as the Re-doping concentration increased. This is due to the new gap states with Re doping, also causing band gap narrowing. The band gap narrowing causes a shift in absorption in the NIR region, and therefore, it could impact photothermal performance. To confirm this hypothesis, different compositions of $Mo_xRe_{1-x}S_2$ were subjected to photothermal experiments.

Particle Size and Charge

Figure 11A:
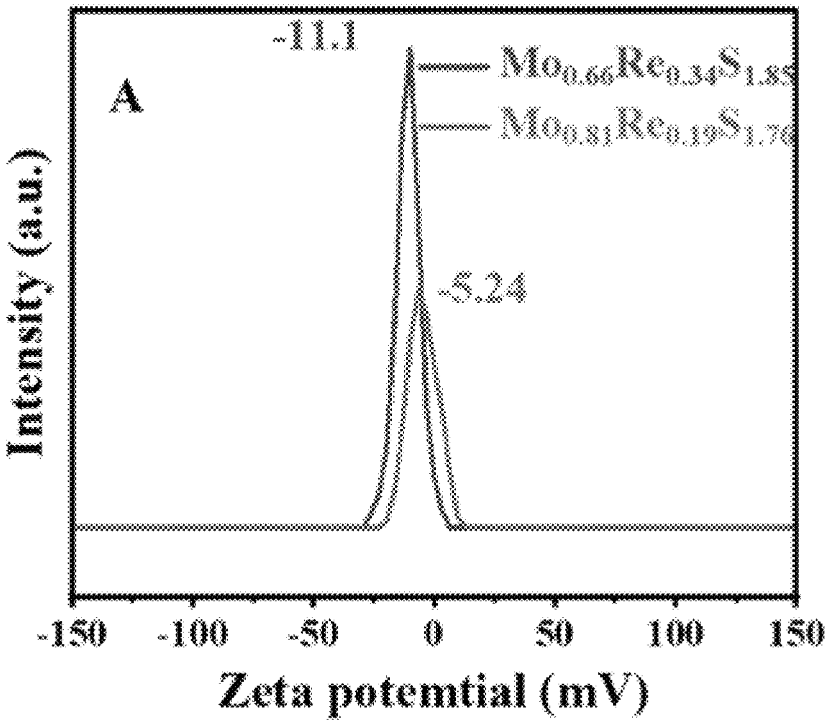
FIGS. 11A-11B show Zeta potential of $Mo_{0.66}Re_{0.34}S_{1.85}$ and $Mo_{0.81}Re_{0.19}S_{1.76}$ (A) and particle size distribution of $Mo_{0.66}Re_{0.34}S_{1.85}$ and $Mo_{0.81}Re_{0.19}S_{1.76}$ (B). The mean of the zeta potential of $Mo_{0.66}Re_{0.34}S_{1.85}$ and $Mo_{0.81}Re_{0.19}S_{1.76}$ is −11.1, and −5.24 mV, respectively. The mean of the particle size of $Mo_{0.66}Re_{0.34}S_{1.85}$ and $Mo_{0.81}Re_{0.19}S_{1.76}$ is around 161.6 nm, and 119.4 nm, respectively.
Figure 11B:
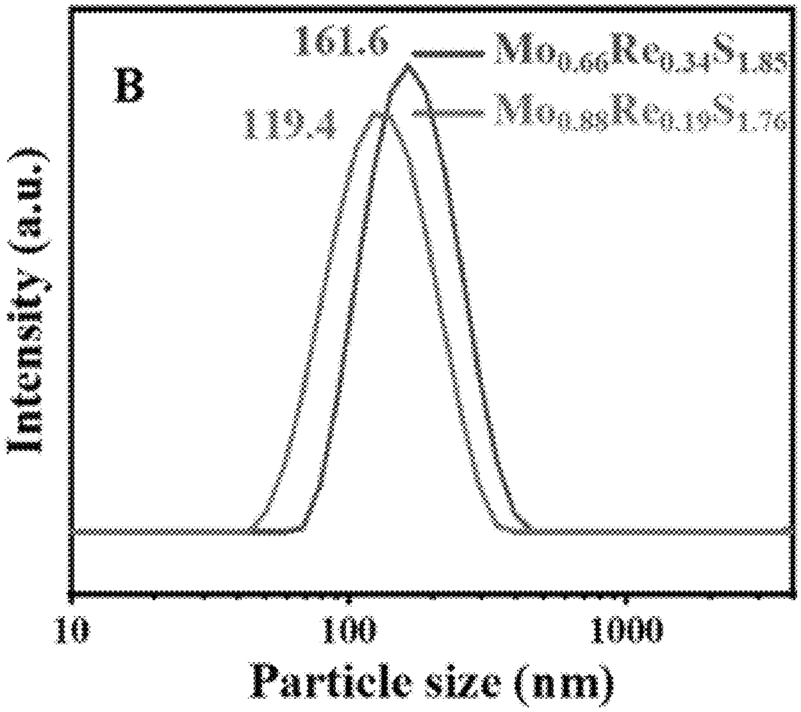

The particle size distribution and zeta potential were determined by using dynamic light scattering (DLS). As shown in FIG. 11, the particle size of $Mo_{0.66}Re_{0.34}S_{1.85}$ and $Mo_{0.81}Re_{0.19}S_{1.76}$ is in the range of 80-300 nm with average particle size of about 162 and 119 nm, respectively. As reported, cationic nanoparticles penetrate cellular membranes, destabilizing the entire membrane structure enough to destroy the cell at higher concentrations. Given the negative charge of $Mo_{0.66}Re_{0.34}S_{1.85}$ and $Mo_{0.81}Re_{0.19}S_{1.76}$, they would not interfere with healthy human cells and disrupt their membranes in practical antifungal applications, exploiting only the catalytic pathway to effectively kill fungi.

Example 2—Photothermal Performance of $Mo_xRe_{1-x}S_2$

Figure 12A:
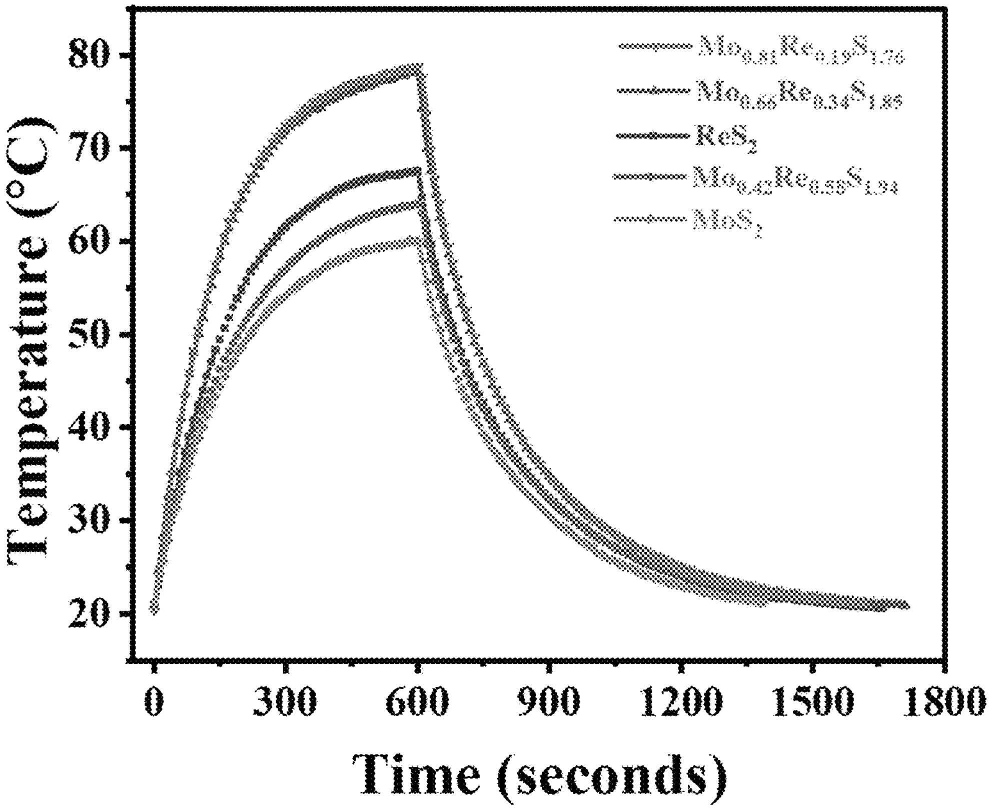
FIGS. 12A-12D show (A) Temperature profile of $Mo_xRe_{1-x}S_2$ nanozyme suspension (200 μg/mL) as a function of time, when irradiated with IR light waves (808 nm, 1 W/$cm^2$) followed by natural cooling without irradiation. (B) Temperature profiles (heating only) of $Mo_{0.66}Re_{0.34}S_{1.85}$ and $Mo_{0.81}Re_{0.19}S_{1.76}$ nanozymes at different concentrations (0-200 μg/mL) and (C) corresponding thermal images captured of different periods 0-10 min. (D) Photothermal stability of $Mo_{0.66}Re_{0.34}S_{1.85}$ and $Mo_{0.81}Re_{0.19}S_{1.76}$ nanozyme suspension (100 μg/mL) for successive 5 cycles of irradiation.

Samples of each nanozyme (200 μg/mL dispersed in $H_2O$) were exposed to near-infrared laser light (808 nm) of intensity 1 $W/cm^2$ for 10 min, and the temperature variation was measured at intervals of 10 s. After 10 min, the laser was turned off, and the temperature was measured continuously until it reached room temperature. FIG. 12A shows the temperature profiles of all $Mo_xRe_{1-x}S_2$ nanozyme samples as a function of time. The samples with compositions $Mo_{0.66}Re_{0.34}S_{1.85}$ and $Mo_{0.81}Re_{0.19}S_{1.76}$ achieved the highest temperature of 80° C. (after 600 s) compared to the other samples. The photothermal conversion efficiency (η) of $Mo_xRe_{1-x}S_2$ was calculated using Eq. 2.

$$\eta = \frac{hA(\Delta T_{max,mix} - \Delta T_{max,H_2O})}{I(1 - 10^{-A_{808}})} \quad \text{(Eq. 2)}$$

where A is the surface area of the container, h is the heat transfer coefficient, $\Delta T_{max,mix}$ and $\Delta T_{max,H_2O}$ are the temperature changes of the $Mo_xRe_{1-x}S_2$ and solvent (water), respectively, at the maximum steady-state temperature, I represents the laser power, and $A_\lambda$ is the absorbance of $Mo_xRe_{1-x}S_2$ NSs at 808 nm.

The calculated values of η for $Mo_xRe_{1-x}S_2$ nanozymes are presented in Table 4. The nanozymes with a composition of $Mo_{0.66}Re_{0.34}S_{1.85}$ and $Mo_{0.81}Re_{0.19}S_{1.76}$ exhibit η=21.6% and 21.8%, respectively, which were higher compared to that of $ReS_2$ (17.2%), $Mo_{0.42}Re_{0.58}S_{1.94}$ (16.4%), and $MoS_2$ (16.1%).

TABLE 4

The summary of photothermal conversion efficiency (η) of $Mo_xRe_{1-x}S_2$ NSs.

| Samples | $\Delta T_{max,mix}$ (° C.) | $A_\lambda$ (808 nm) | η |
|---|---|---|---|
| $ReS_2$ | 67.5 | 0.848 | 17.2 |
| $Mo_{0.42}Re_{0.58}S_{1.94}$ | 64 | 0.907 | 16.4 |
| $Mo_{0.66}Re_{0.34}S_{1.85}$ | 78.3 | 0.883 | 21.6 |
| $Mo_{0.81}Re_{0.19}S_{1.76}$ | 78.8 | 0.841 | 21.8 |
| $MoS_2$ | 60.1 | 0.904 | 16.1 |

Figure 12B:
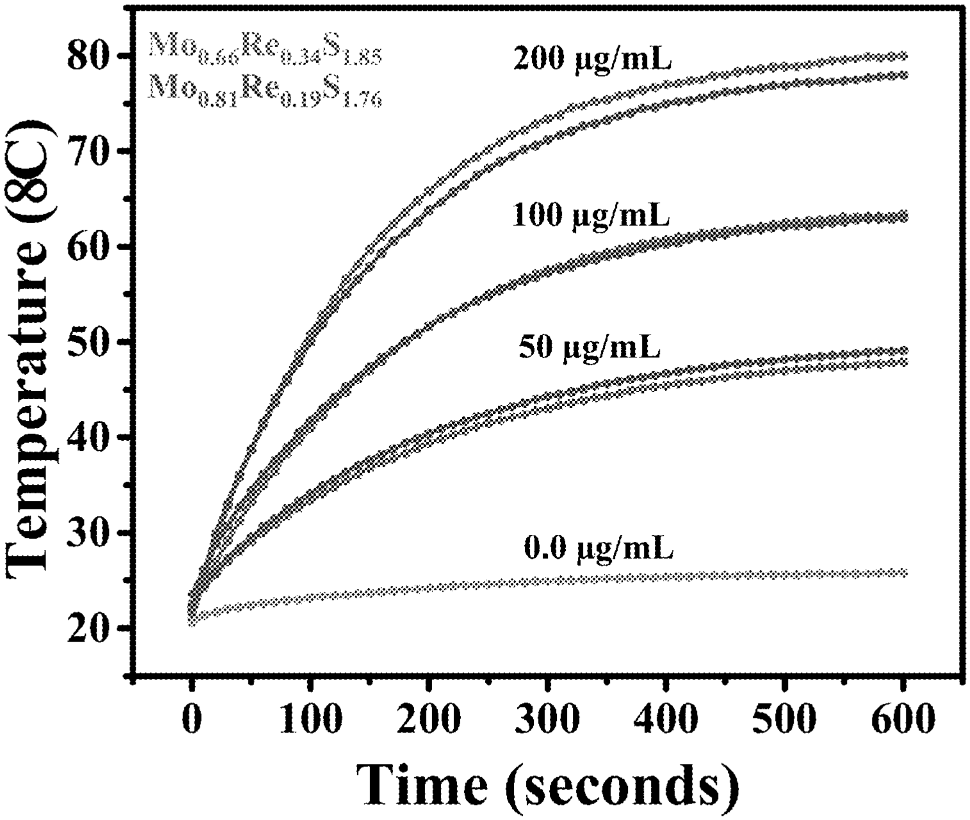
Figure 12C:
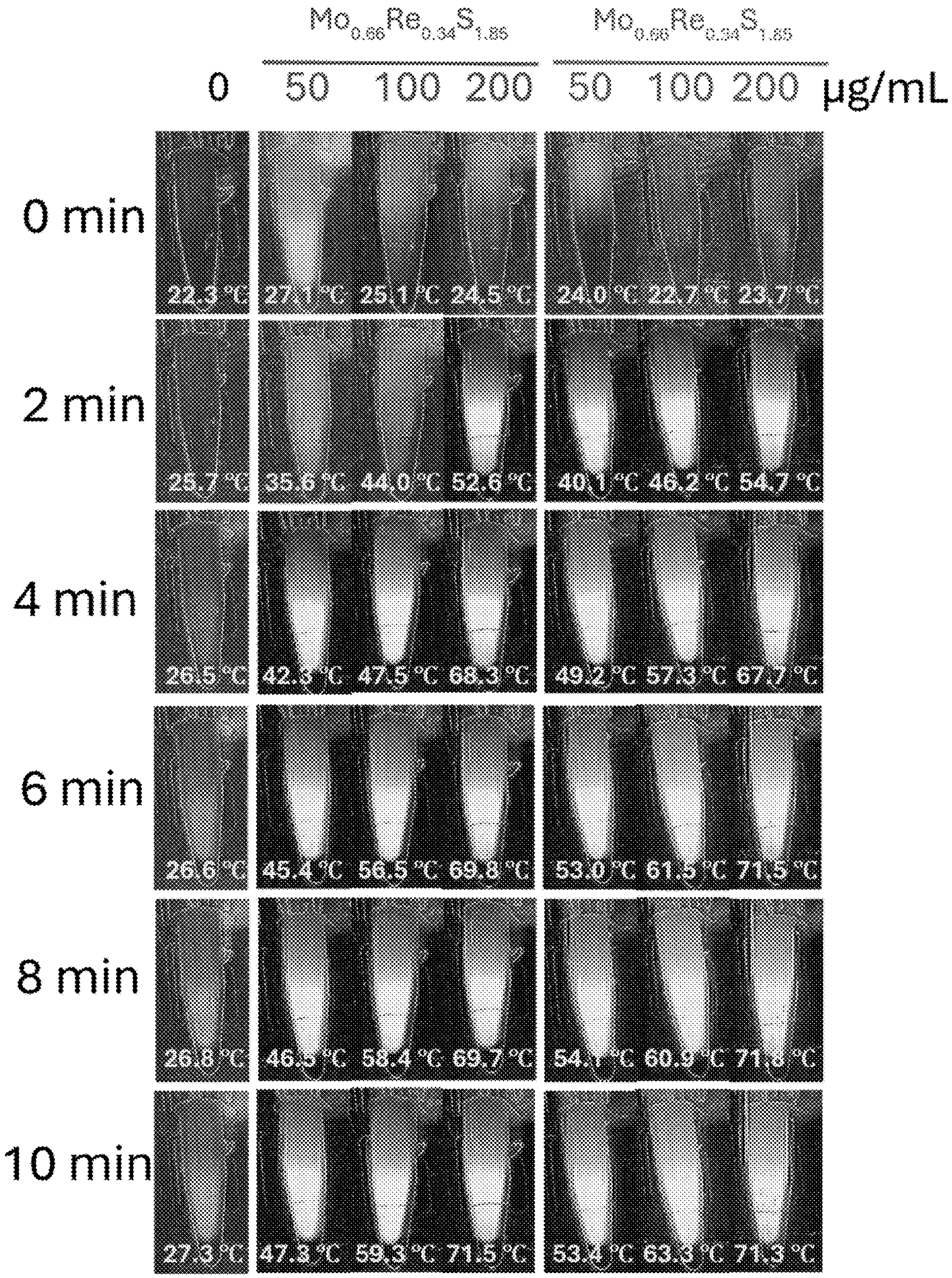
Figure 12D:
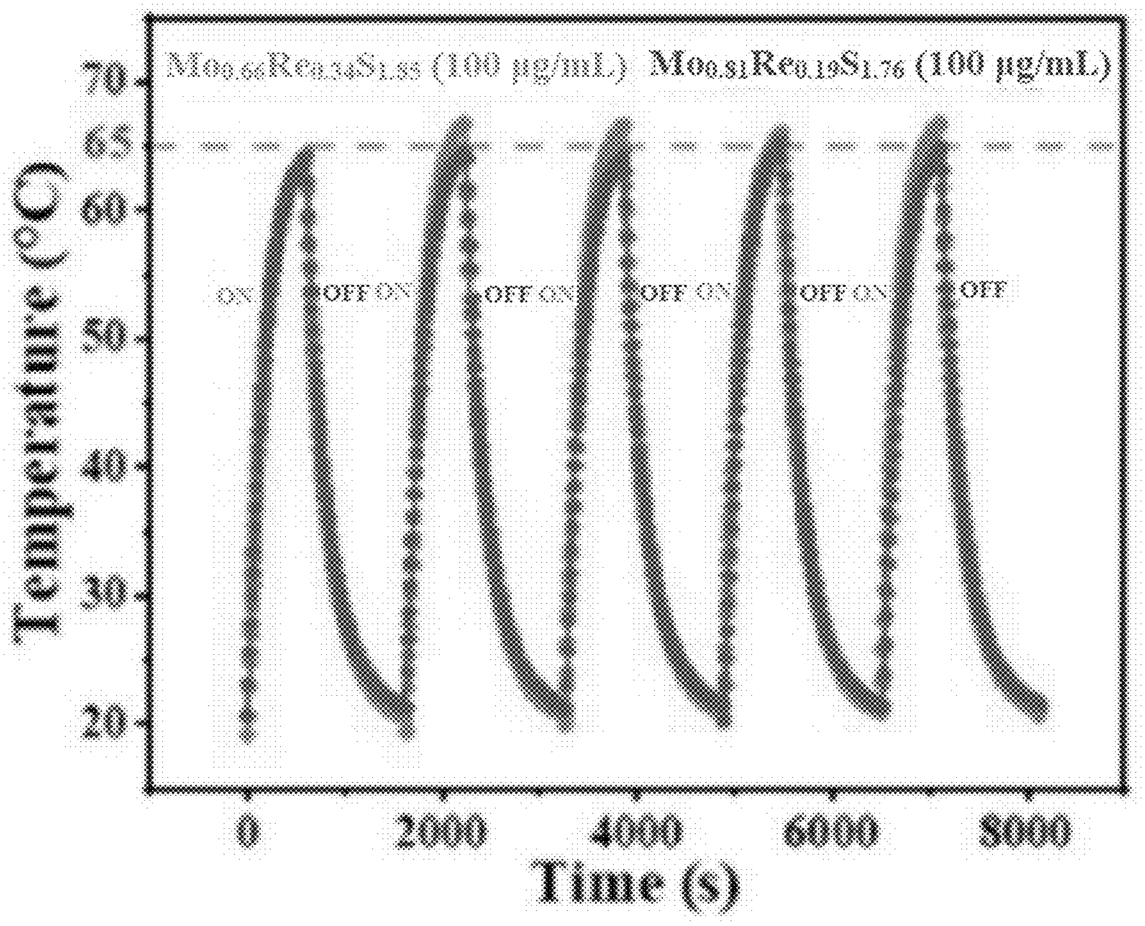

The $Mo_{0.66}Re_{0.34}S_{1.85}$ and $Mo_{0.81}Re_{0.19}S_{1.76}$ nanozymes were further explored for photothermal studies. To identify the appropriate temperature for the in vitro assay, different concentrations (0-200 μg/mL) of the $Mo_{0.66}Re_{0.34}S_{1.85}$ and $Mo_{0.81}Re_{0.19}S_{1.76}$ nanozymes were tested (FIG. 12B). Thermal images were collected, and the temperature change could be observed vividly in FIG. 12C. $H_2O$ served as the negative control and exhibited no significant temperature changes over 10 min (from 22.3 to 27.3° C.). However, with increasing concentration, the temperature gradually increased for 10 min. The materials showed high photothermal stability featured during five heating/cooling cycles under the same treatment, which provided consistent performance and potential for antifungal activity (FIG. 12D).

Example 3—POD-Like Activity and Kinetic Study of $Mo_xRe_{1-x}S_2$

Figure 13A:
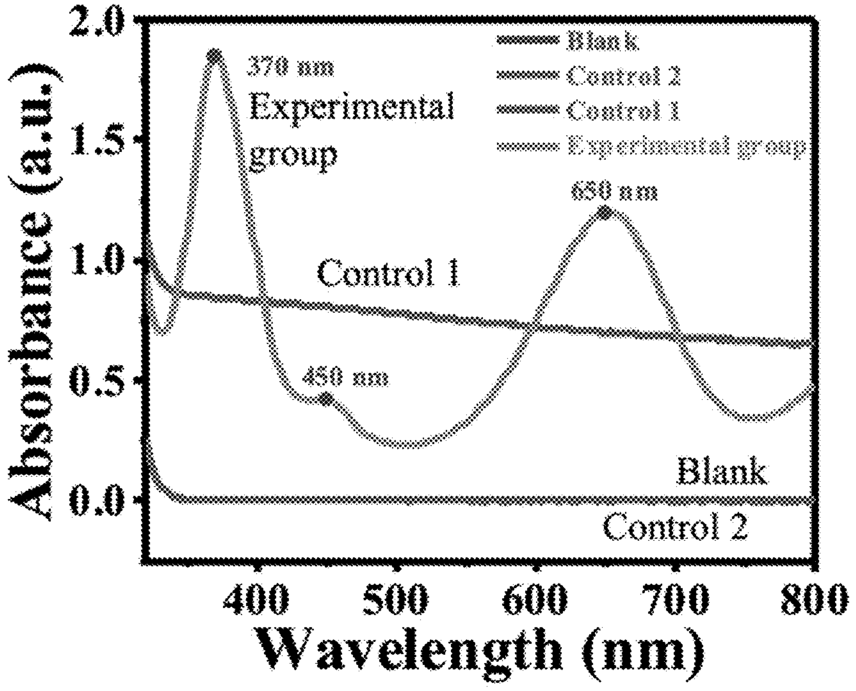
FIGS. 13A-13B show (A) Absorption spectra of different systems. Blank: TMB and $H_2O_2$ were mixed without a catalyst; control 1: TMB and catalyst were mixed without $H_2O_2$; control 2: $H_2O_2$ and catalyst were mixed without TMB; experimental group: TMB and $H_2O_2$ were mixed with a catalyst. (B) Effects of different pH values (2.2-8) on relative POD activity for $Mo_{0.66}Re_{0.34}S_{1.85}$ and $Mo_{0.81}Re_{0.19}S_{1.76}$ nanozymes.
Figure 13B:
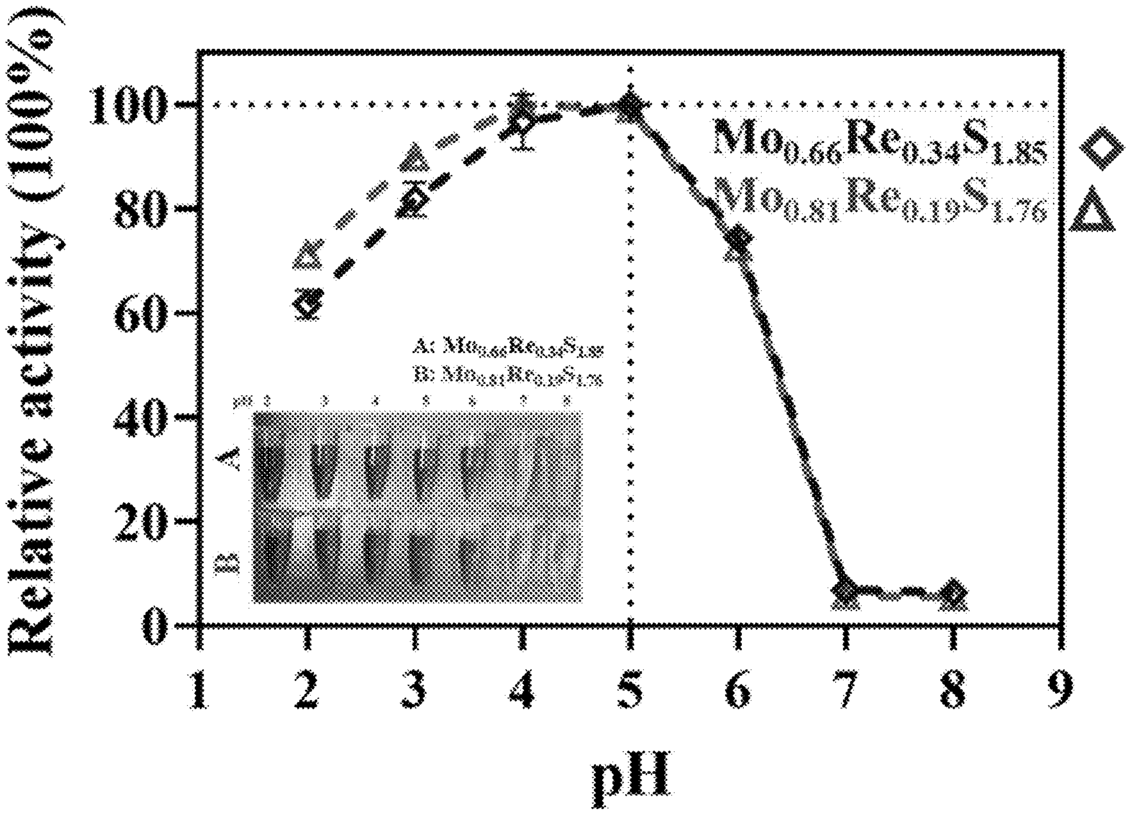
Figure 14A:
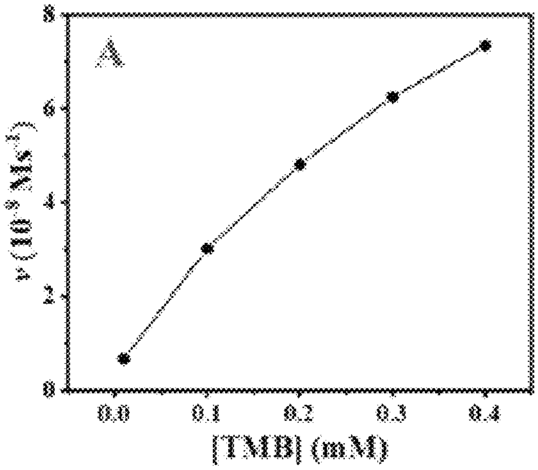
FIGS. 14A-14H show a steady-state kinetic assay of peroxidase-like activity of $Mo_{0.66}Re_{0.34}S_{1.85}$ and $Mo_{0.81}Re_{0.19}S_{1.76}$ (pH 5) at room temperature as a function of [TMB] in panels (A) and (E) and $H_2O_2$, in panels (B) and (F), and corresponding double-reciprocal plots (C) corresponding to (A); (G) to (E), (D) to (B), and (H) to (F). (A) The concentration of $H_2O_2$ was 2 mM and TMB was varied (0.01-0.4 mM). (B) TMB concentration was fixed at 1.66 mM and $H_2O_2$ was varied (0.1-4 mM). (E) The concentration of $H_2O_2$ was 2 mM and TMB was varied (0.01-0.4 mM). (F) TMB concentration was fixed at 1.66 mM and $H_2O_2$ was varied (0.1-1.0 mM).
Figure 14B:
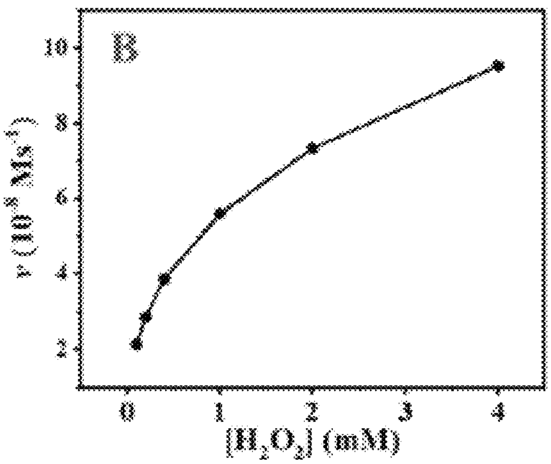
Figure 14C:
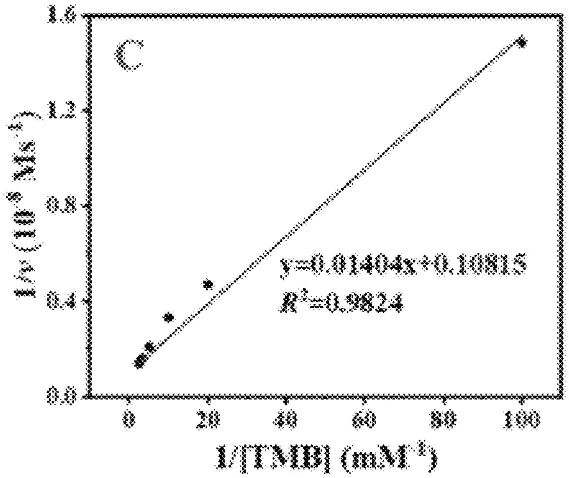
Figure 14D:
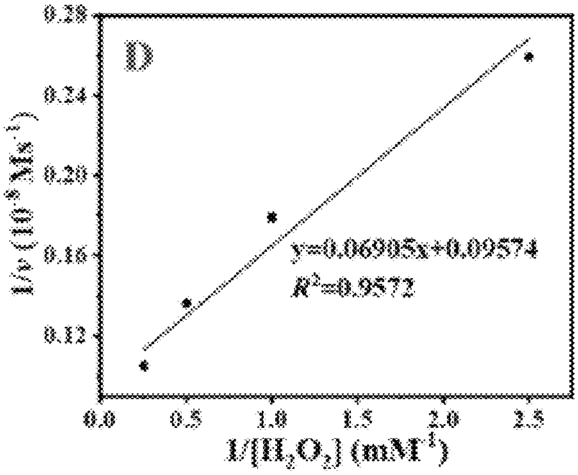
Figure 14E:
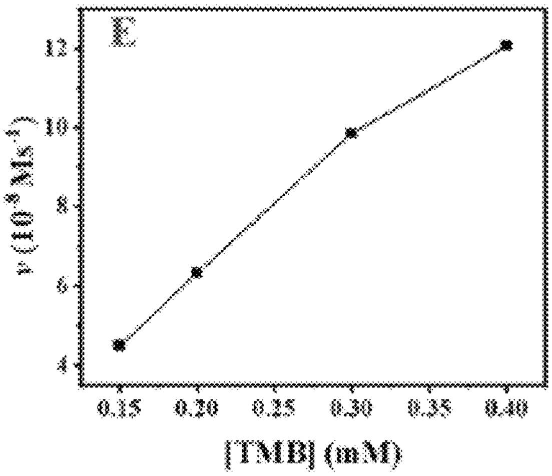
Figure 14F:
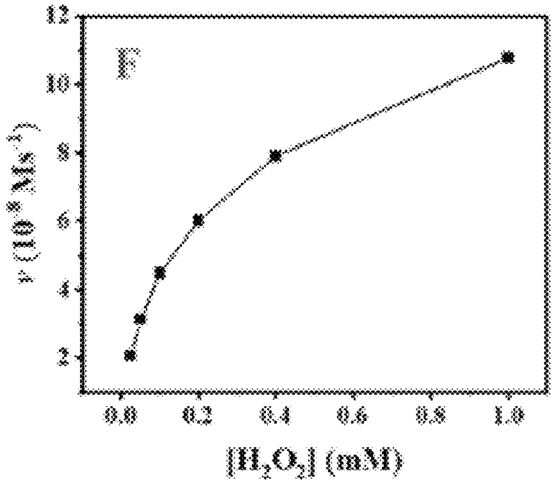
Figure 14G:
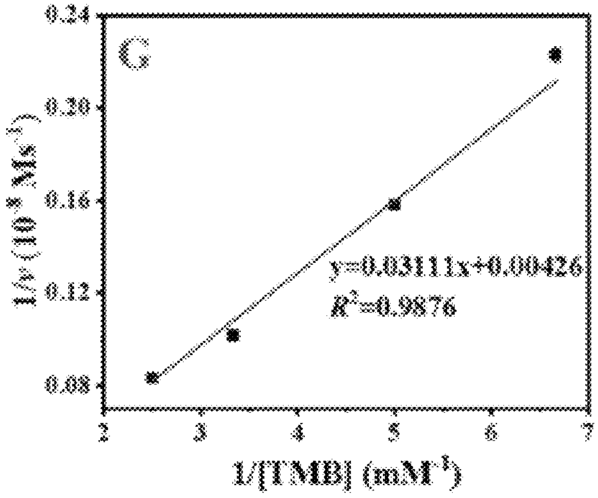
Figure 14H:
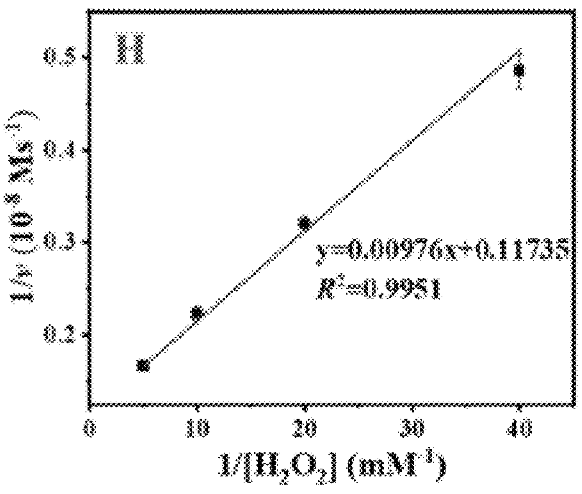

The POD-like activity of $Mo_{0.66}Re_{0.34}S_{1.85}$ and $Mo_{0.81}Re_{0.19}S_{1.76}$ nanozymes was evaluated by using a typical POD catalytic system with TMB and $H_2O_2$ as the substrates. Absorption spectra were recorded under the different experimental conditions. No characteristic peaks were observed when using TMB alone (control 1) or $H_2O_2$ alone (control 2) or when TMB and $H_2O_2$ were mixed without a catalyst (blank). FIG. 13A indicates that TMB cannot be oxidized by $H_2O_2$ without a catalyst. However, with the addition of $Mo_xRe_{1-x}S_2$ nanozymes, strong absorption peaks appeared at 370 and 650 nm (experimental group), demonstrating the formation of oxidized TMB (oxTMB). In addition, the effect of pH on the catalytic activity was tested (FIG. 13B), showing that from pH 2.2 to 5, relative POD activity exhibited a gradual increase, beginning at 60% and reaching its maximum activity at pH 5 (100%). However, as the pH increased from 5 to 6, the activity gradually decreased. The most significant decline in activity occurred between pH 6 and pH 7, where it dropped abruptly to nearly zero. Beyond pH 7, specifically at pH 8, no further change in activity was observed, indicating a complete loss of functional activity.

To quantify the catalytic efficiency and specificity of $Mo_xRe_{1-x}S_2$ toward the POD substrate, the Michaelis-Menten kinetics were further investigated. Experiments were conducted by varying the concentration of TMB or $H_2O_2$ while keeping the other conditions constant. Lineweaver-Burk plots were generated to determine the Michaelis-Menten constant ($K_m$) for TMB and $H_2O_2$ (FIG. 14). A lower $K_m$ value indicates a higher affinity between the enzyme and the substrate. Table 5 summarizes the linear fit data, and Table 6 provides the corresponding kinetic parameters. The $K_m$ value for the $Mo_{0.81}$ $Re_{0.19}S_{1.76}$ nanozyme with TMB as the substrate was 56 times higher than that of $Mo_{0.66}Re_{0.34}S_{1.85}$, whereas the Vmax value of the $Mo_{0.81}Re_{0.19}S_{1.76}$ nanozyme was 25 times higher than that of $Mo_{0.66}Re_{0.34}S_{1.85}$. Conversely, the $K_m$ value for the $Mo_{0.81}Re_{0.19}S_{1.76}$ nanozyme with $H_2O_2$ as the substrate was 9 times lower than that of $Mo_{0.66}Re_{0.34}S_{1.85}$, and its Vmax value was 1.2 times lower. These results indicate that $Mo_{0.66}$ $Re_{0.34}S_{1.85}$ has a higher affinity for TMB, while $Mo_{0.81}Re_{0.19}S_{1.76}$ has a higher affinity for $H_2O_2$, implying that the $Mo_{0.81}Re_{0.19}S_{1.76}$ nanozyme has a greater peroxidase-like activity.

TABLE 5

Summary of plots of the steady-state kinetic assay of $Mo_{0.66}Re_{0.34}S_{1.85}$ and $Mo_{0.81}Re_{0.19}S_{1.76}$.

| Samples | $H_2O_2$ | $R^2$ | TMB | $R^2$ |
|---|---|---|---|---|
| $Mo_{0.66}Re_{0.34}S_{1.85}$ | y = 0.06905x + 0.09574 | 0.9574 | y = 0.01404x + 0.10815 | 0.9824 |
| $Mo_{0.81}Re_{0.19}S_{1.76}$ | y = 0.00976x + 0.11735 | 0.9951 | y = 0.03111x + 0.00426 | 0.9876 |

TABLE 6

Kinetic parameters of the steady-state kinetic assay of $Mo_{0.66}Re_{0.34}S_{1.85}$ and $Mo_{0.81}Re_{0.19}S_{1.76}$.

| | $V_{max}$ ($10^{-8}$ M*$s^{-1}$) | | $K_m$ (mM) | |
|---|---|---|---|---|
| Samples | $H_2O_2$ | TMB | $H_2O_2$ | TMB |
| $Mo_{0.66}Re_{0.34}S_{1.85}$ | 10.445 | 9.246 | 0.7212 | 0.1298 |
| $Mo_{0.81}Re_{0.19}S_{1.76}$ | 8.522 | 234.742 | 0.0789 | 7.3028 |

Example 4—Cell Viability Assay

Figure 15:
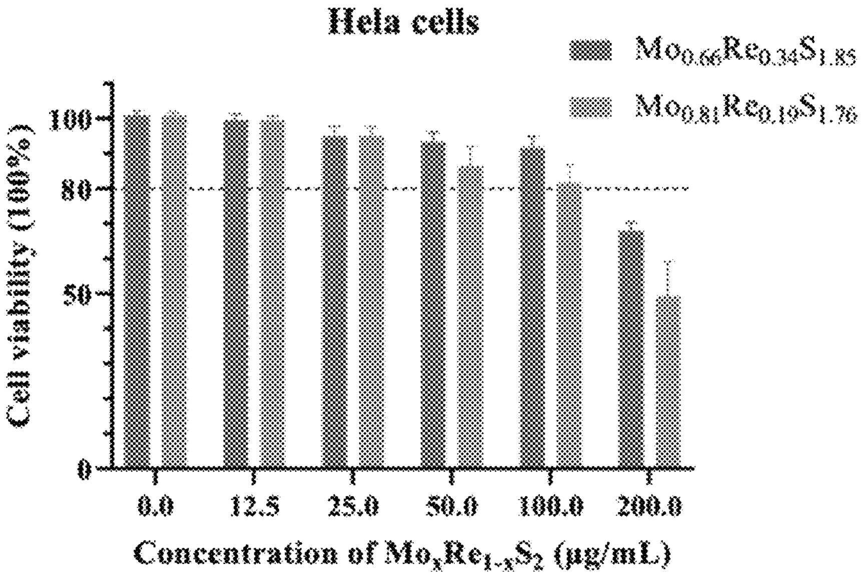
FIG. 15 shows cell viability experiments in the HeLa cell line after treatment with $Mo_{0.66}Re_{0.34}S_{1.85}$ and $Mo_{0.81}Re_{0.19}S_{1.76}$ nanoparticles at different concentrations (12.5, 25, 50, 100, and 200 mg/mL) for 24 h. HeLa cells treated with PBS were used as a control.

To understand the antifungal potential of nanozymes in biomedical applications, it is critical to assess the biocompatibility of $Mo_xRe_{1-x}S_2$ before conducting further in vivo studies. The biocompatibility assay was performed using HeLa cells, incubated with $Mo_xRe_{1-x}S_2$ at various concentrations for 24 h; the cytotoxicity was evaluated using a CCK-8 assay. The results showed that low concentrations of $Mo_{0.66}Re_{0.34}S_{1.85}$ and $Mo_{0.81}Re_{0.19}S_{1.76}$ did not impact HeLa cell survival rates. However, at 100 μg/mL, the cell viability decreased to 90% and 80%, respectively (FIG. 15).

At concentrations of up to 200 μg/mL, $Mo_{0.66}Re_{0.34}S_{1.85}$ and $Mo_{0.81}Re_{0.19}S_{1.76}$ nanozymes exhibited toxicity in vitro. These results suggest that $Mo_xRe_{1-x}S_2$ has good biocompatibility at concentrations of up to 100 μg/mL.

Example 5—Antifungal Activity and *C. albicans* Staining Test

Figure 16A:
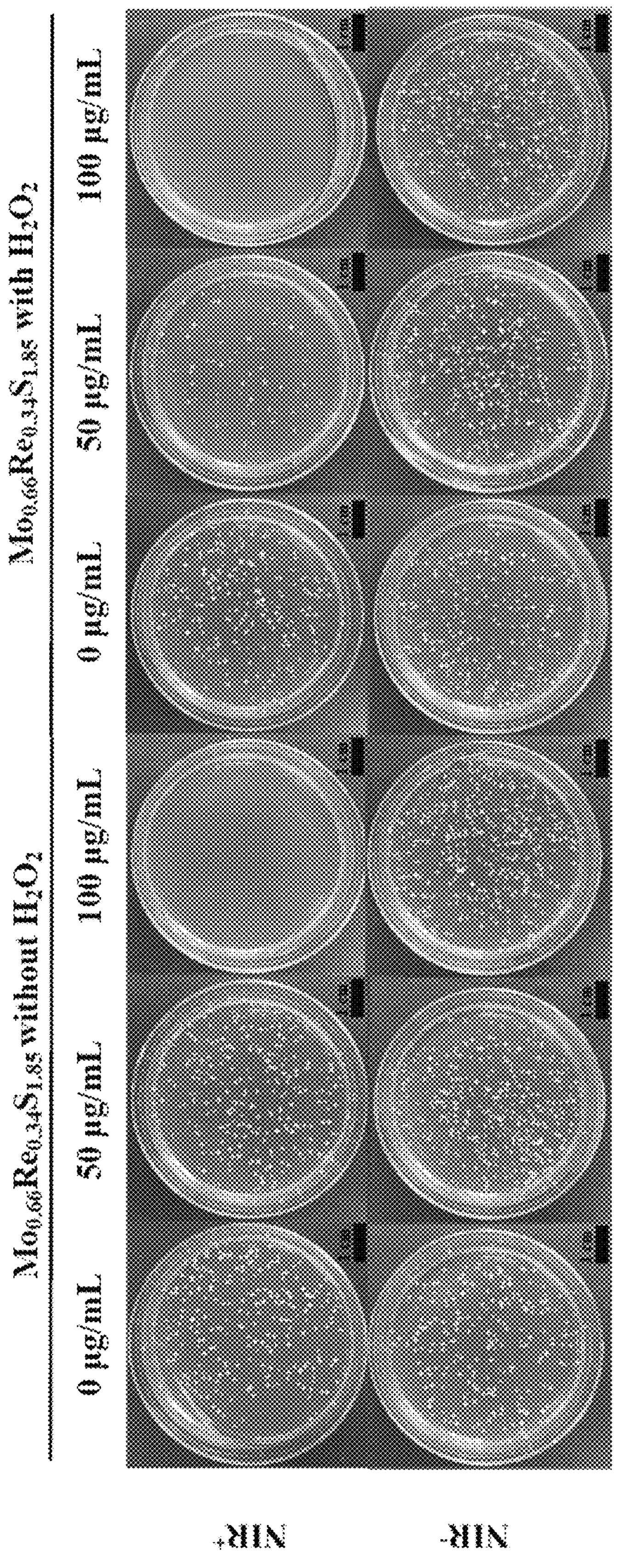
FIGS. 16A-16F show (A, C) Photographs of the SDA agar plates with *C. albicans* following different treatments with varying concentrations of $Mo_{0.66}Re_{0.34}S_{1.85}$ and $Mo_{0.81}Re_{0.19}S_{1.76}$ and (B, D) corresponding fluorescence staining confocal images of *C. albicans* using AO/PI taken after 1 h of different treatments. (E, F) Relative viability of *C. albicans* after various treatments were applied to the agar plates.
Figure 16B:
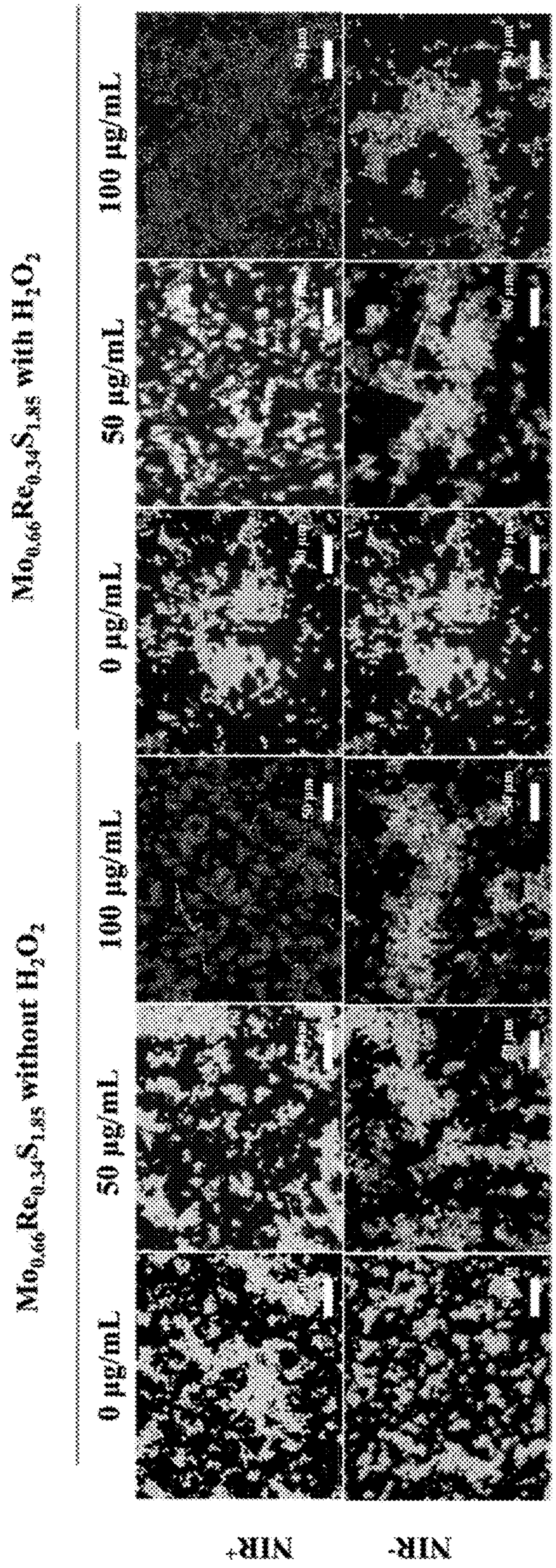
Figure 16C:
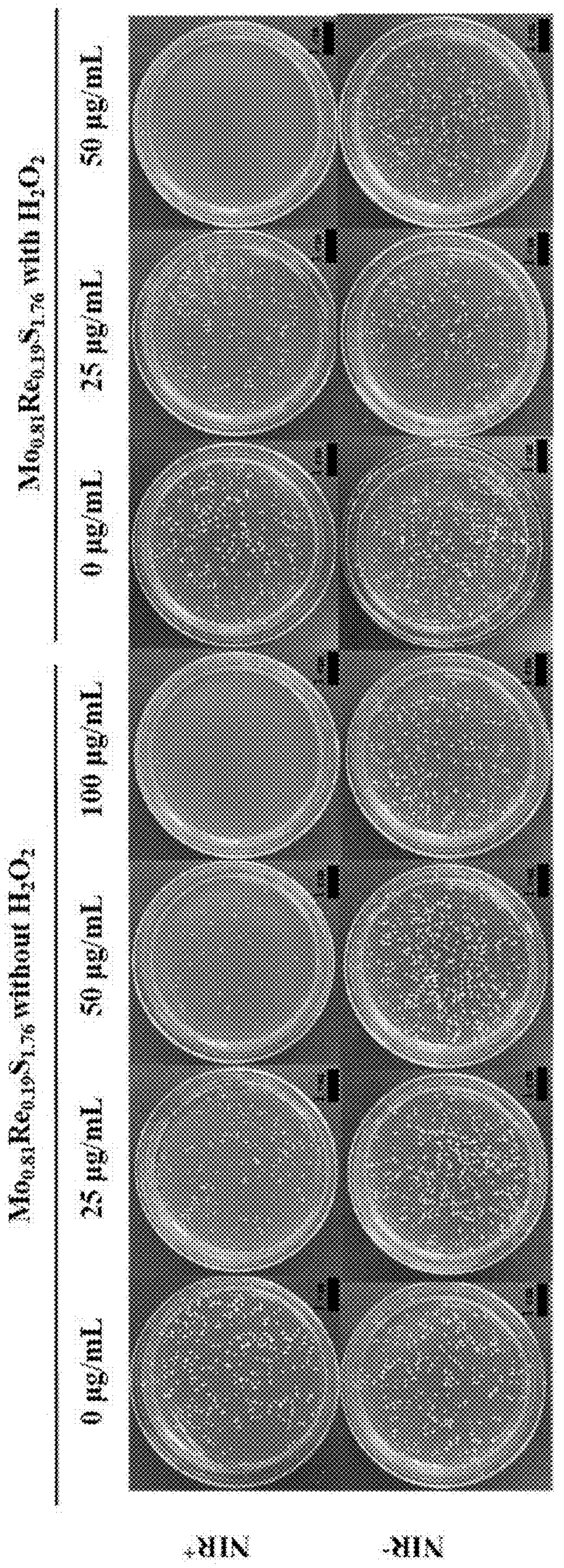
Figure 16D:
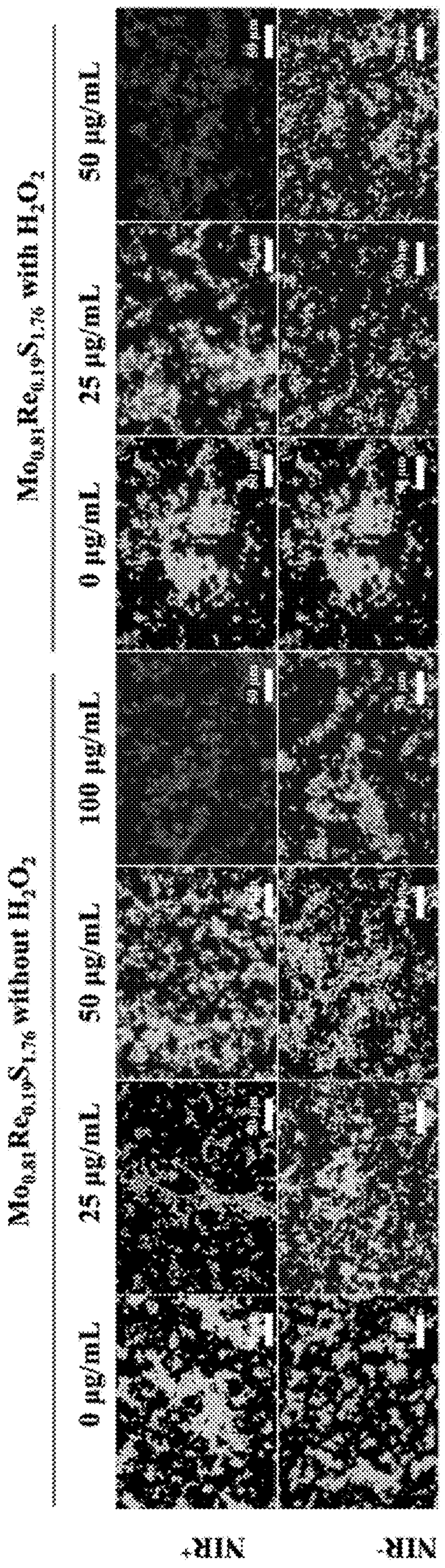
Figure 16E:
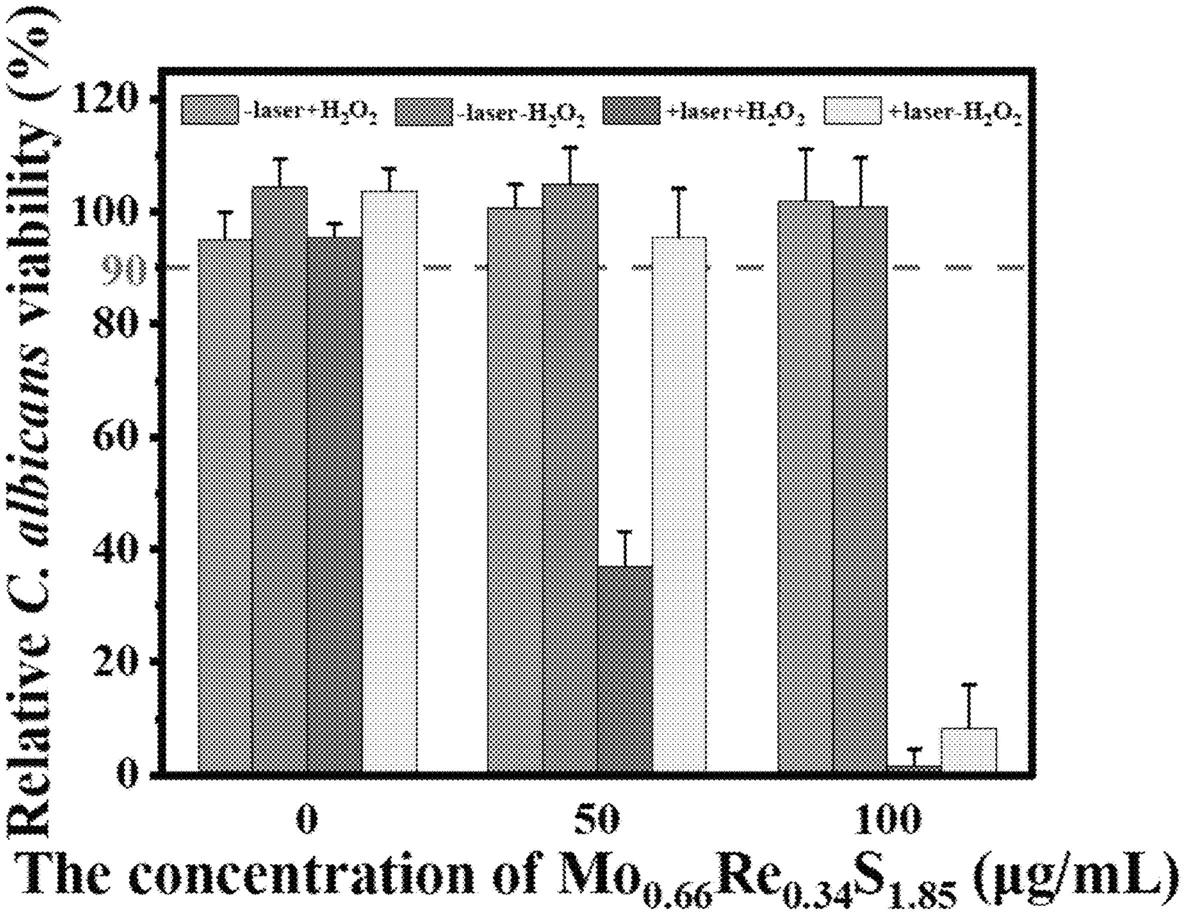
Figure 16F:
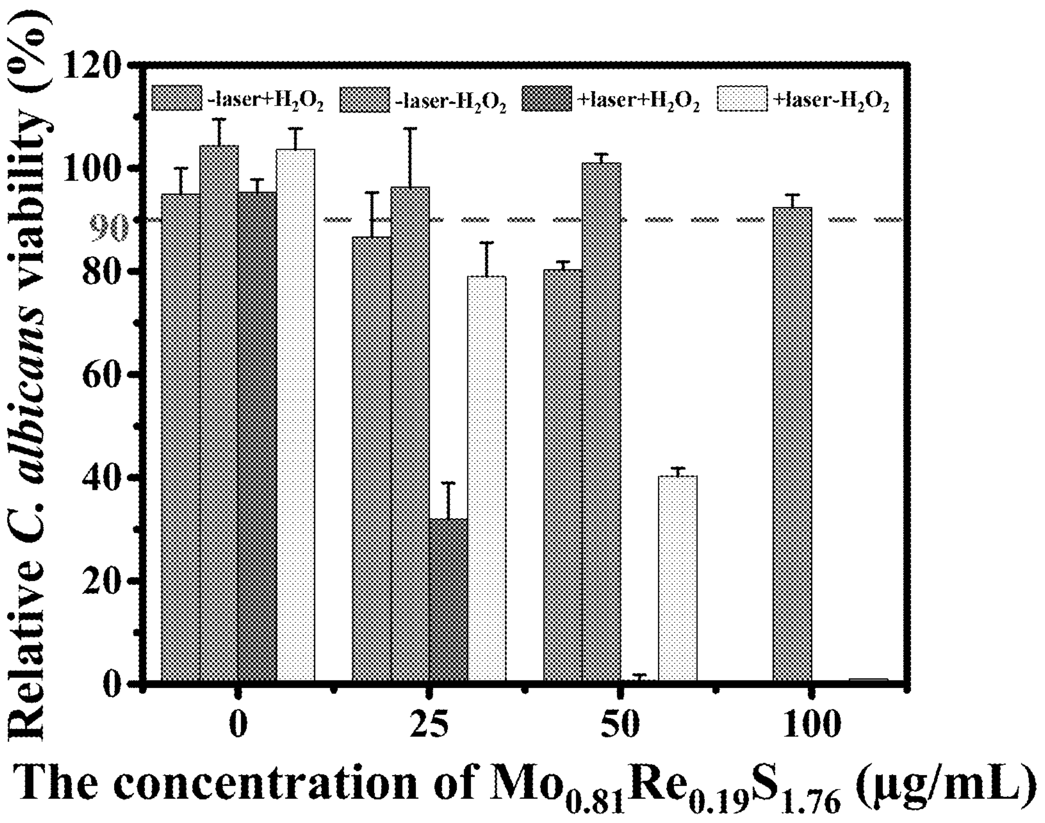

Samples were examined for their antifungal activity against *C. albicans* by plating. Initially, *C. albicans* was treated with the same amount of $H_2O_2$ but different concentrations of $Mo_xRe_{1-x}S_2$ nanozymes at 808 nm laser for 10 min. As shown in FIG. 16A, the $H_2O_2$ control showed no killing compared with the PBS control, which means that the $H_2O_2$ itself is not toxic enough to kill the fungi in the test. With a concentration of 50 μg/mL $Mo_{0.66}Re_{0.34}S_{1.85}$, its POD-like activity showed noticeable fungi-killing, and 100 μg/mL $Mo_{0.66}Re_{0.34}S_{1.85}$ without $H_2O_2$ killed the fungi during the photothermal exposure. The $Mo_{0.81}Re_{0.19}S_{1.76}$ sample (FIG. 14B) showed better peroxidase-like activity and antifungal effect in the presence of $H_2O_2$ than that of $Mo_{0.66}Re_{0.34}S_{1.85}$, using a lower concentration of nanozyme. The experiment was conducted in triplicate. Additionally, the antifungal effect of $Mo_{0.66}Re_{0.34}S_{1.85}$ and $Mo_{0.81}Re_{0.19}S_{1.76}$ nanozymes was directly observed through live/dead staining (AO and PI) of *C. albicans* after various treatments, aligning with the spread plate data. FIG. 16B shows strong green fluorescence in three $NIR^+$ groups, including 0 μg/mL $Mo_{0.66}Re_{0.34}S_{1.85}$ with no $H_2O_2$ (group 1), 50 μg/mL $Mo_{0.66}$ $Re_{0.34}S_{1.85}$ with no $H_2O_2$ (group 2), 0 μg/mL $Mo_{0.66}Re_{0.34}S_{1.85}$ with $H_2O_2$ (group 3) and all the $NIR^-$ groups indicated that living colonies that could only take up AO. Conversely, strong red fluorescence was observed (FIG. 16B) in the 100 μg/mL $Mo_{0.66}Re_{0.34}S_{1.85}$ and 100 μg/mL $Mo_{0.66}$ $Re_{0.34}S_{1.85}$ with $H_2O_2$ $NIR^+$ groups represent dead *C. albicans* colonies capable of uploading PI. The yellow areas in the confocal images, a combination of the green and red fluorescence, suggest that some fungal membranes may have thinned or been damaged, allowing the PI dye to penetrate and bind to the DNA, staining the nucleus red. FIG. 16C presents photographs of the SDA agar plates with *C. albicans* following different treatments of $Mo_{0.81}Re_{0.19}S_{1.76}$. Fluorescence confocal images in FIG. 16D show yellow areas from the 25 μg/mL $Mo_{0.81}Re_{0.19}S_{1.76}+H_2O_2$ $NIR^+$ group, while the 50 μg/mL $Mo_{0.81}Re_{0.19}S_{1.76}+H_2O_2$ $NIR^+$ group exhibited only strong red fluorescence. These findings suggest a positive correlation between the peroxidase-like activity and the photothermal effect of $Mo_{0.66}Re_{0.34}S_{1.85}$ and $Mo_{0.81}$ $Re_{0.19}S_{1.76}$ nanozymes and their antifungal activities.

Figure 17A:
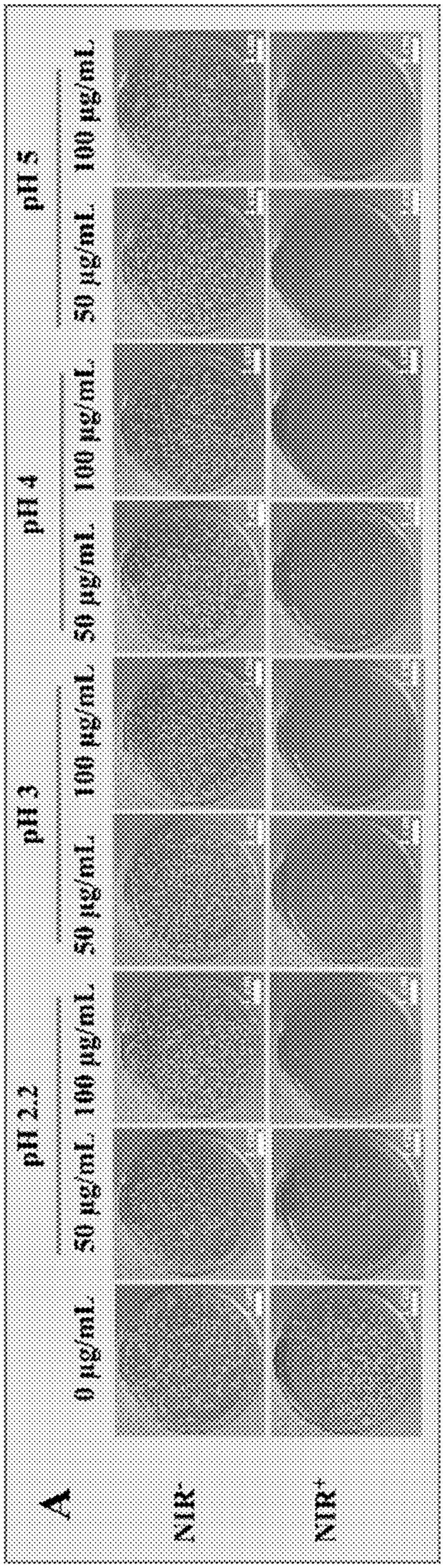
FIGS. 17A-17B show photographs of the SDA agar plates with *C. albicans* following different treatments with varying concentrations of $Mo_{0.66}Re_{0.34}S_{1.85}$ (A) and $Mo_{0.81}Re_{0.19}S_{1.76}$ (B) under different pH solutions for 16 h.
Figure 17B:
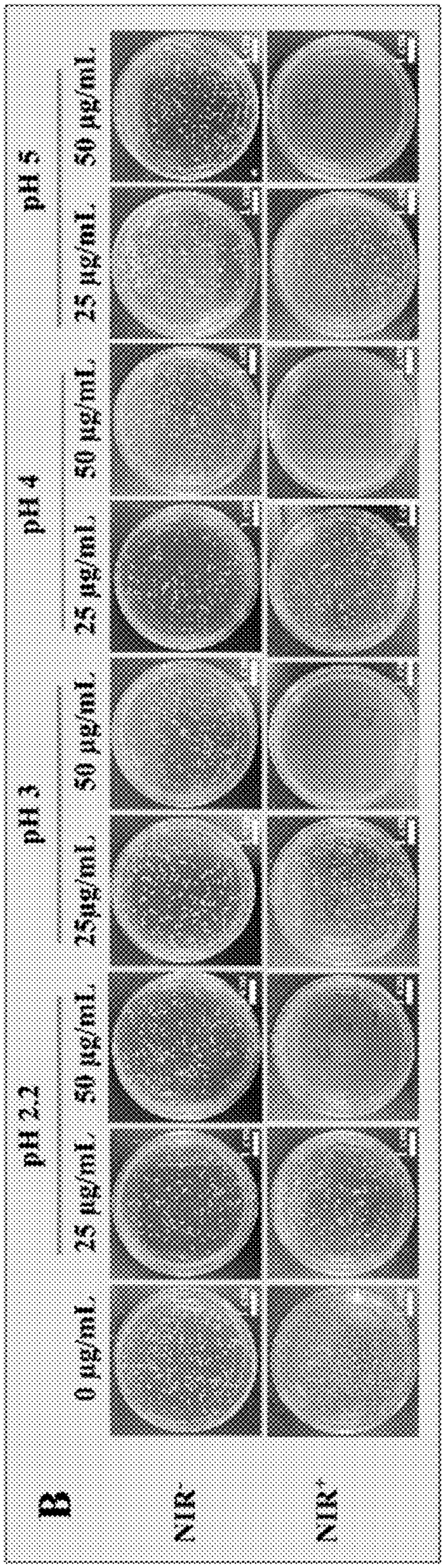
Figure 18A:
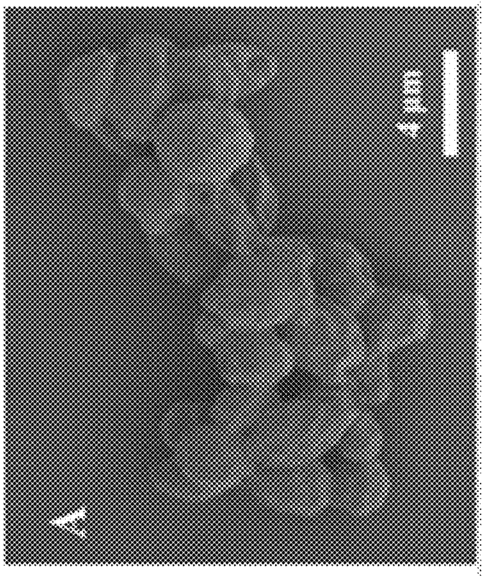
FIGS. 18A-18E show SEM images of fungi under different treatments (A: blank control, B: treated with $Mo_{0.66}Re_{0.34}S_{1.85}$, C: treated with $Mo_{0.81}Re_{0.19}S_{1.76}$). SEM elemental mapping analysis of the fungi under different treatments (D: treated with $Mo_{0.66}Re_{0.34}S_{1.85}$, E: treated with $Mo_{0.81}Re_{0.19}S_{1.76}$).
Figure 18B:
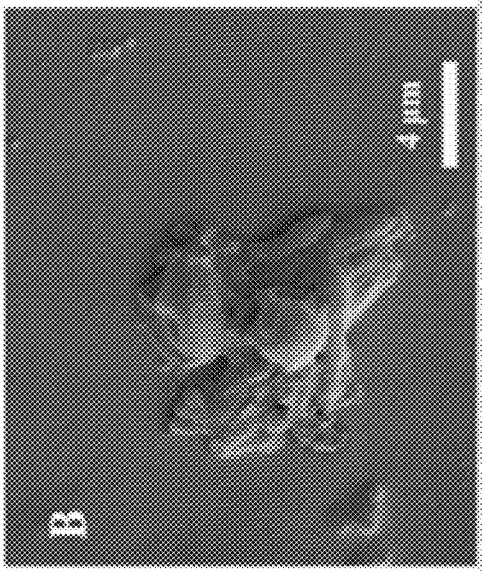
Figure 18C:
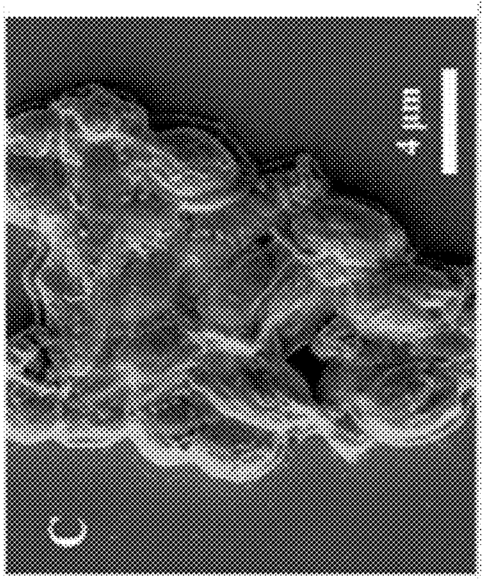
Figure 18D:
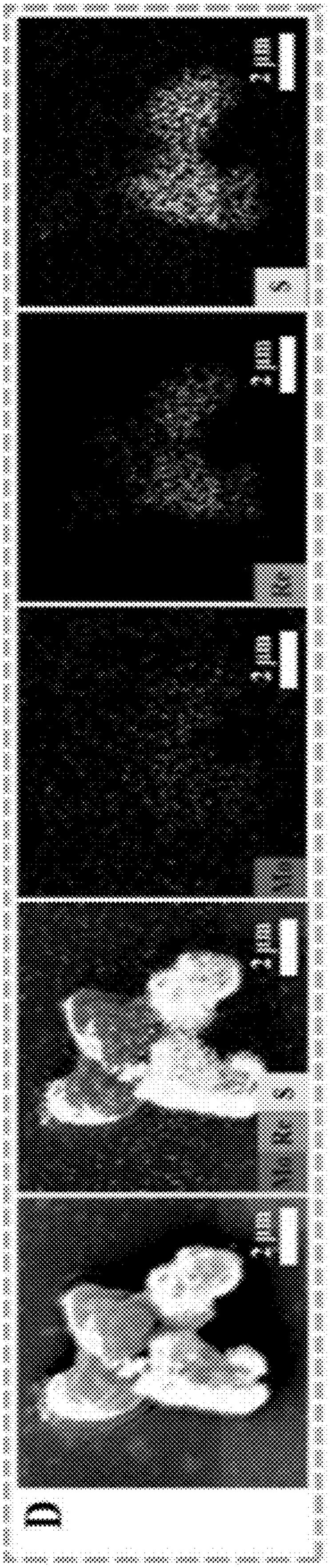
Figure 18E:
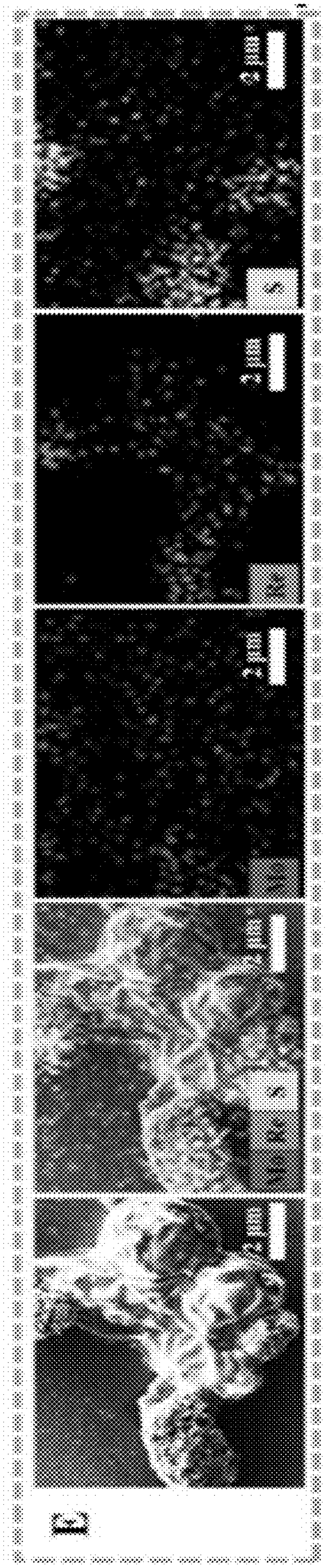

The antifungal activities of $Mo_{0.66}Re_{0.34}S_{1.85}$ and $Mo_{0.81}Re_{0.19}S_{1.76}$ were also evaluated for the acidic pH treated samples (FIG. 17). The results suggest that the material activity is not impacted by an acidic environment and longer exposure does not diminish antifungal activity. Both the structural stability and functional antifungal efficacy of $Mo_{0.66}Re_{0.34}S_{1.85}$ and $Mo_{0.81}$ $Re_{0.19}S_{1.76}$ are preserved across the tested pH ranges, highlighting their resilience and use for applications under acidic environments

Example 6—Imaging of *C. albicans* Morphology

To uncover the effects of interaction between $Mo_xRe_{1-x}S_2$ NSs and *C. albicans*, the morphological changes in *C. albicans* were examined by using SEM and SEM EDX. FIG. 18 illustrates that the antifungal effects observed in the $Mo_{0.66}Re_{0.34}S_{1.85}$ and $Mo_{0.81}Re_{0.19}S_{1.76}$ groups were due to the surface collapse of *C. albicans*. The fungal skeletal structure was either significantly deformed or completely collapsed after the treatment. These findings confirmed that the photothermal effect and POD-like activity of $Mo_xRe_{1-x}$ $S_2$ NSs play decisive roles in the fungicide process, suggesting their potential as a novel treatment method for fungal infection.

Example 7—Characterizations of $Mo_{0.66}Re_{0.34}S_{1.85}$

Among PF127/CMC/$Mo_xRe_{1-x}S_2$ samples evaluated for photothermal properties, PF127/CMC/$Mo_{0.66}Re_{0.34}S_{1.85}$ demonstrated the best performance, reaching a maximum temperature of 56.6° C. after 10 min under laser irradiation. Additionally, cytotoxicity assays from the aforementioned studies highlighted the superior biocompatibility of $Mo_{0.66}Re_{0.34}S_{1.85}$ nanosheets, which demonstrated significantly higher cell viability (68%) compared to $Mo_{0.81}$ $Re_{0.19}S_{1.76}$ nanosheets (50%) at a concentration of 200 μg/mL. These results underscored the potential of PF127/CMC/$Mo_{0.66}Re_{0.34}S_{1.85}$ as a promising candidate for biomedical applications. Therefore, the PF127/CMC/$Mo_{0.66}Re_{0.34}S_{1.85}$ hydrogel was selected for further evaluation and study, and the $Mo_{0.66}Re_{0.34}S_{1.85}$ nanomaterial was fully characterized.

Figure 19A:
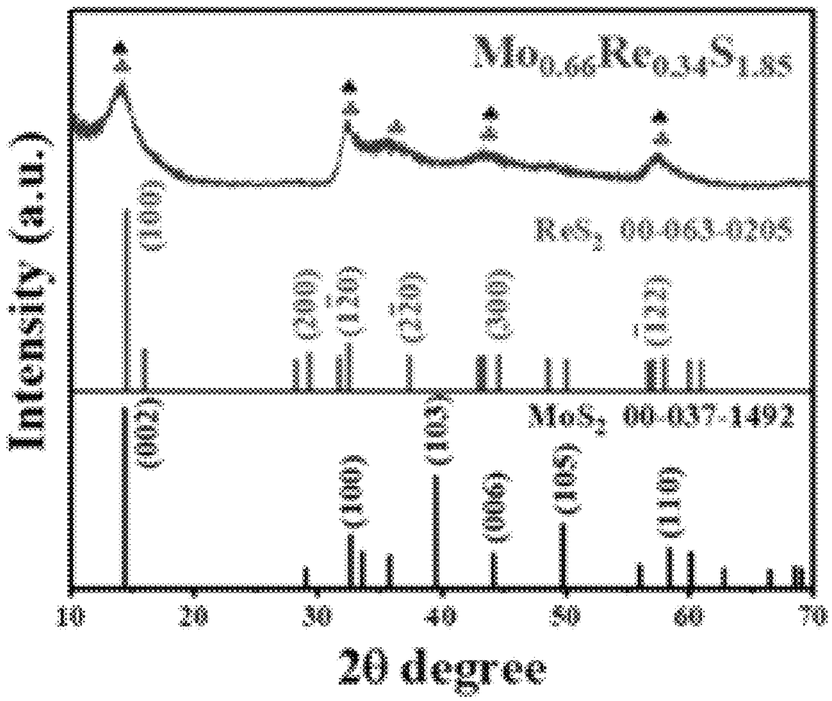
FIGS. 19A-19C show (A) XRD pattern, (B) Raman spectra, (C) zeta potential, particle size distribution of $Mo_{0.66}Re_{0.34}S_{1.85}$.
Figure 19B:
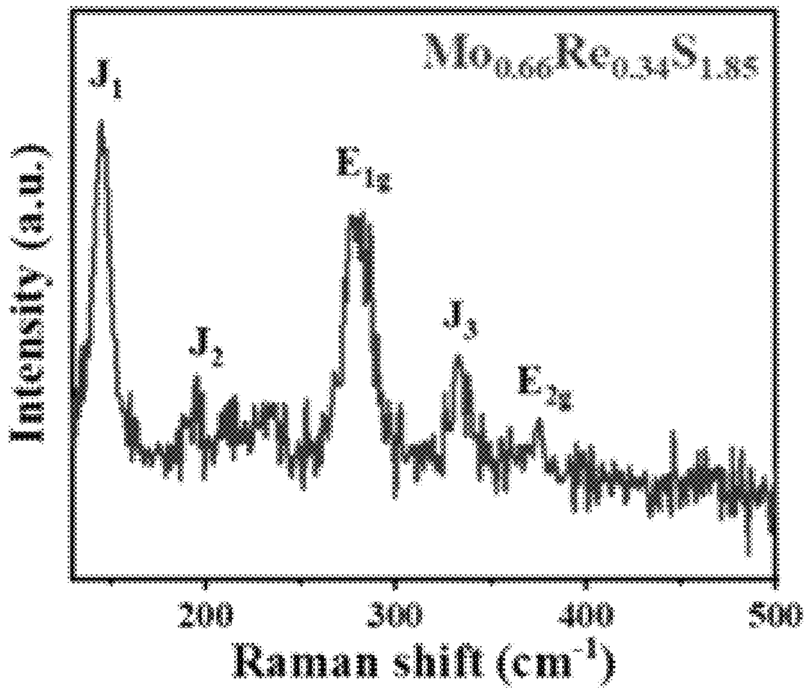
Figure 19C:
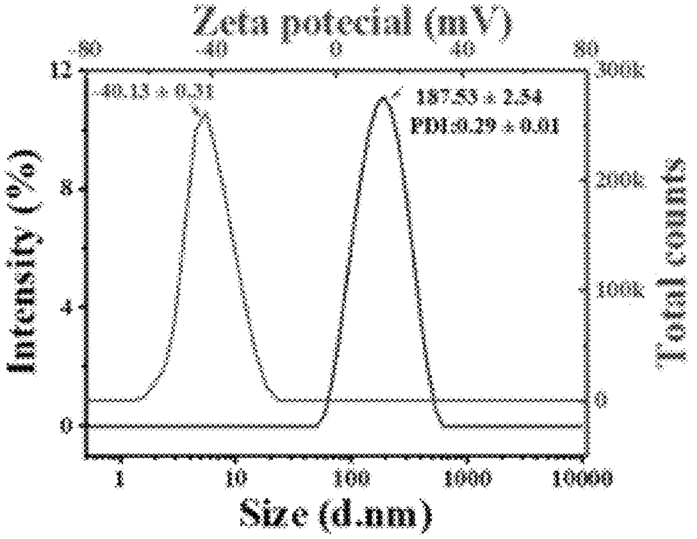

The nanomaterial was evaluated by X-ray diffraction (XRD), Raman spectroscopy, and dynamic light scattering (DLS), providing comprehensive structural and analytical details. XRD analysis (FIG. 19A) revealed that the XRD pattern of $Mo_{0.66}Re_{0.34}S_{1.85}$ closely resembles the standard patterns of pure $ReS_2$ (JCPDS no. 00-063-0205) and $MoS_2$ (JCPDS no. 00-037-1492), confirming its crystallographic structure. The Raman spectrum of $Mo_{0.66}Re_{0.34}S_{1.85}$ (FIG. 19B) displays characteristic longitudinal vibration modes of the 1T-phase $MoS_2$ at 130 $cm^{-1}$ ($J_1$), 195 $cm^{-1}$ ($J_2$), and 336 $cm^{-1}$ ($J_3$). Additionally, the Raman peak observed at 380 $cm^{-1}$ ($E_{2g}$) corresponds to the in-plane vibrational modes of S—Mo—S. Dynamic light scattering (DLS) measurements indicate a particle size distribution of 187.53±2.54 nm, and zeta potential of −40.13±0.31 mV, consistent with previously reported values for $Mo_{0.66}Re_{0.34}S_{1.85}$.

Example 8—Gelation Time of Hydrogels with Varying PF127 to CMC Ratios

Figure 20A:
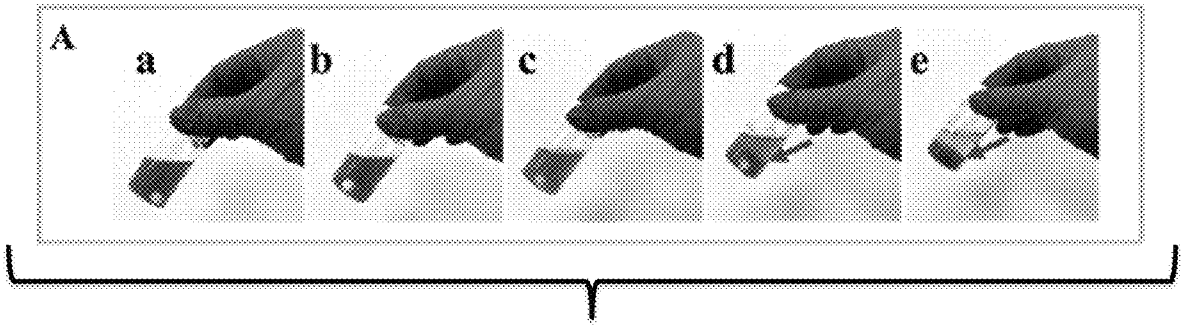
FIGS. 20A-20E show (A) Visual appearance of CMC/PF127/$Mo_{0.66}Re_{0.34}S_{1.85}$ hydrogels formed with different CMC/PF127 content per Table 2. (B) Gelation time of hydrogels formed with different CMC/PF127 content (see Table 2) containing 0.2 mg/mL $Mo_{0.66}Re_{0.34}S_{1.85}$. (C) Plot of the apparent viscosity as a function of the shear rate for PF127/CMC hydrogel, and PF127/CMC/$Mo_{0.66}Re_{0.34}S_{1.85}$ hydrogel. (D) Viscosity plot. (E) Oscillatory temperature sweep showed storage (G') and loss modulus (G") of PF127/CMC hydrogel, and PF127/CMC/$Mo_{0.66}Re_{0.34}S_{1.85}$ hydrogel between 2° and 35° C.
Figure 20B:
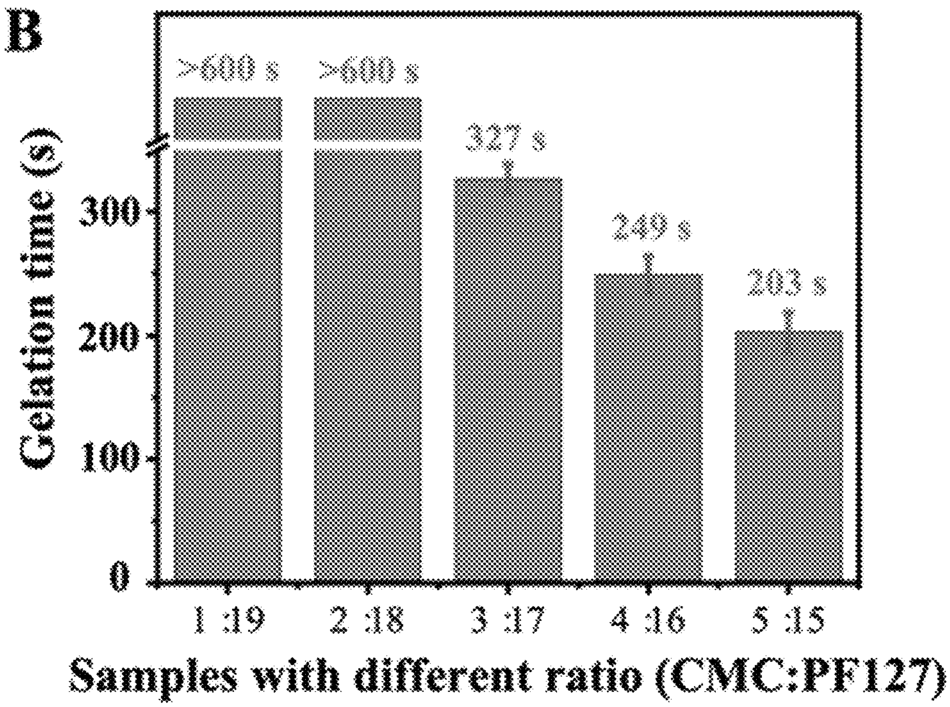

The critical gelling temperature corresponds to the transitions of a thermoresponsive hydrogel from the liquid phase to a cloudy gel state, and gelation time refers to the duration needed for this transformation at a specific temperature. For thermoresponsive hydrogels, slow gelation may lead to hydrogel delocalization, whereas rapid gelation below 30° C. could cause syringe needle blockages. FIGS. 20A and B illustrate the visual appearance and gelation time of hydrogels prepared with varying CMC/PF127 content (per Table 2), and containing 0.2 mg/mL $Mo_{0.66}Re_{0.34}S_{1.85}$, at a gelation temperature of 30° C. In FIG. 20A, hydrogels (d) and (e) exhibited nonuniform appearances, with a noticeable accumulation of $Mo_{0.66}Re_{0.34}S_{1.85}$ nanomaterials settling at the bottom of the glass vial. Furthermore, FIG. 20B demonstrates the gelation time exceeded 10 min (>600 s) for the ratios (a) and (b). Based on its appropriate gelation time and homogeneity, the PF127/CMC/$Mo_{0.66}Re_{0.34}S_{1.85}$ hydrogel (c) was selected for further studies. This composition is hereafter referred to as the PF127/CMC/$Mo_{0.66}Re_{0.34}S_{1.85}$ hydrogel, while the hydrogel prepared without $Mo_{0.66}Re_{0.34}S_{1.85}$ is designated as the PF127/CMC hydrogel and used as the control.

Example 9—Rheological Properties

Figure 20C:
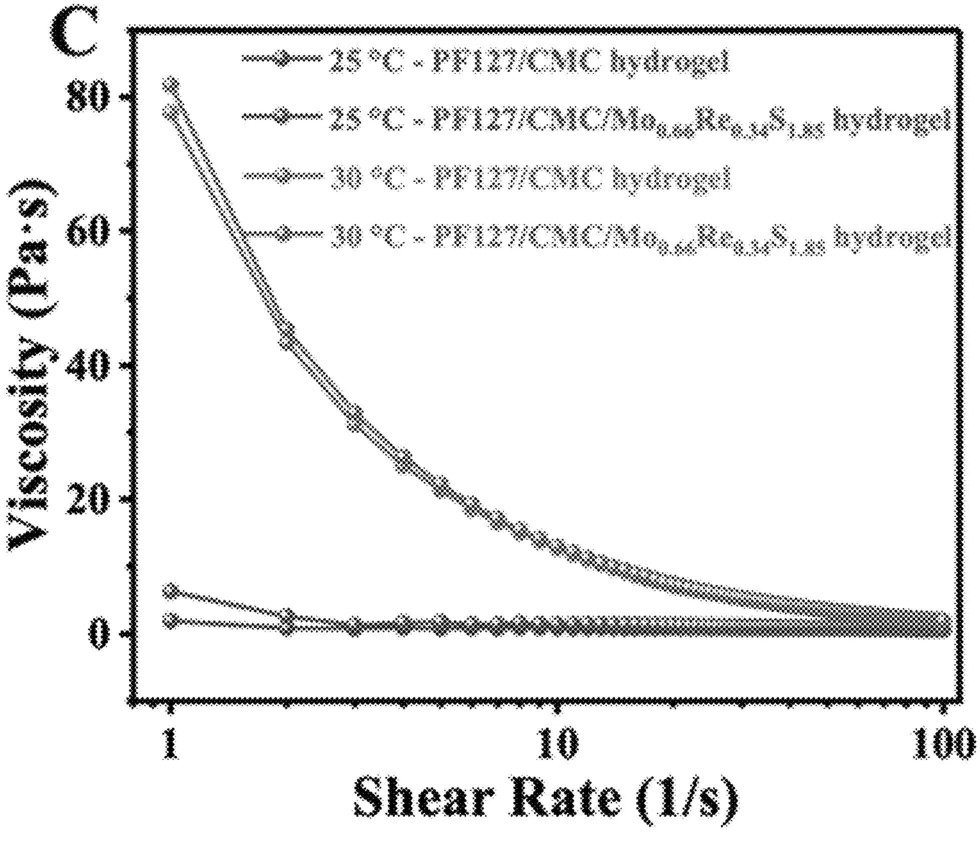
Figure 20D:
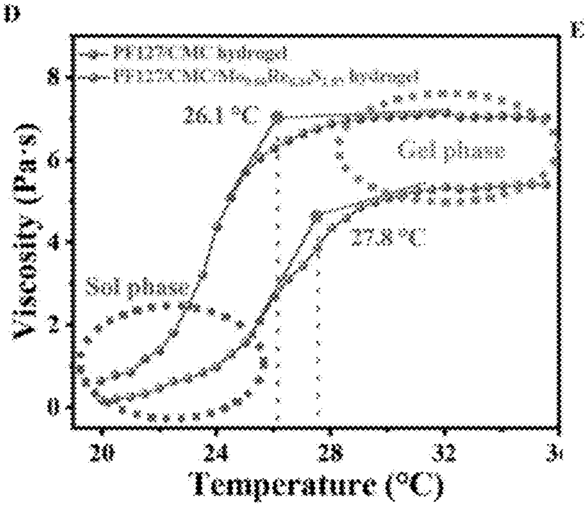

Rheological evaluation is essential in characterizing hydrogels as it provides insights into their mechanical and flow properties. Hydrogels generally exhibit non-Newtonian fluid behavior, wherein their viscosity varies with the applied shear rate. As illustrated in FIG. 20C, the viscosity of both PF127/CMC hydrogel and PF127/CMC/$Mo_{0.66}Re_{0.34}S_{1.85}$ hydrogel decreases progressively with increasing shear rate. Furthermore, this effect is less pronounced at 25° C. compared to 30° C., which can be attributed to the initial state of the hydrogel. At 25° C., the hydrogel exhibits greater fluidity and behaves more like a liquid. In contrast, at 30° C., the hydrogel transitions into a gel state, resulting in significantly different initial fluidity characteristics. This property renders the hydrogels highly suitable for applications such as injectable systems, where continuous flow through a needle is required. As illustrated in FIG. 20D, the viscosity of the PF127/CMC hydrogel is slightly higher than that of PF127/CMC/$Mo_{0.66}Re_{0.34}S_{1.85}$ hydrogel. At 20° C., the viscosity of the PF127/CMC hydrogel is 0.6 Pa s, whereas the viscosity of the PF127/CMC/$Mo_{0.66}Re_{0.34}S_{1.85}$ hydrogel is approximately 0.1 Pa s. As the temperature increases, both hydrogels undergo a transition from a liquid phase to a gel phase, resulting in a significant increase in viscosity. At 35° C., the viscosities of PF127/CMC hydrogel and PF127/CMC/$Mo_{0.66}Re_{0.34}S_{1.85}$ hydrogel reach approximately 7 and 5.8 Pa s, respectively. This slight reduction in viscosity for the PF127/CMC/$Mo_{0.66}Re_{0.34}S_{1.85}$ hydrogel may be attributed to the incorporation of $Mo_{0.66}Re_{0.34}S_{1.85}$. In addition, the sol-gel transition points of PF127/CMC hydrogel and PF127/CMC/$Mo_{0.66}Re_{0.34}S_{1.85}$ hydrogel are 26.1 and 27.8° C., respectively.

Figure 20E:
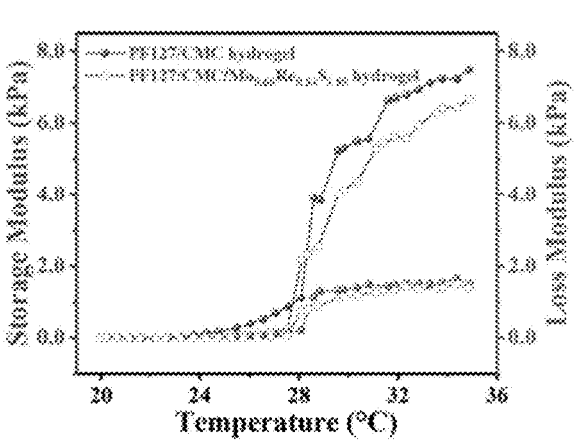

The temperature sweep is a rheological characterization technique employed to assess the structural properties and thermal behavior within a defined temperature range. This approach involves measuring the temperature-dependent variations in the storage modulus (G') and loss modulus (G"), thereby offering valuable insights into the viscoelastic characteristics of the material for different applications. When the hydrogel precursor solution exhibits the behavior characteristic of a solution, G" remains relatively low. However, upon the onset of gelation, there is a marked increase in G', signifying the transition to a gel-like state. FIG. 20E illustrates that both the G' and G" of the hydrogels increase with temperature. As the temperature increases from 20 to 35° C., the storage modulus (G') of the PF127/CMC/$Mo_{0.66}Re_{0.34}S_{1.85}$ hydrogel increased rapidly from 0 to 6.7 kPa, while the loss modulus (G") increased from 0 to 1.4 kPa. Similarly, for the PF127/CMC hydrogel, G' increases sharply from 0 to 7.5 kPa, and G" increases from 0 to 1.4 kPa. These results indicate the formation of a stable gel network with temperature elevation in both hydrogel systems. In addition, a marked increase in G' of both hydrogels is observed at 28° C., indicating a gradual transition from a liquid to a gel state at this temperature. As the temperature rises to 35° C., G' of both hydrogels further increases, suggesting that the viscosity of the hydrogel enhances with temperature. Importantly, no significant differences are observed between the PF127/CMC hydrogel and PF127/CMC/$Mo_{0.66}Re_{0.34}S_{1.85}$ hydrogel, indicating that the incorporation of $Mo_xRe_{1-x}S_2$ nanoparticles does not notably alter the rheological properties of the hydrogel.

Example 10—Hardness Performance of Hydrogels

Figure 21:
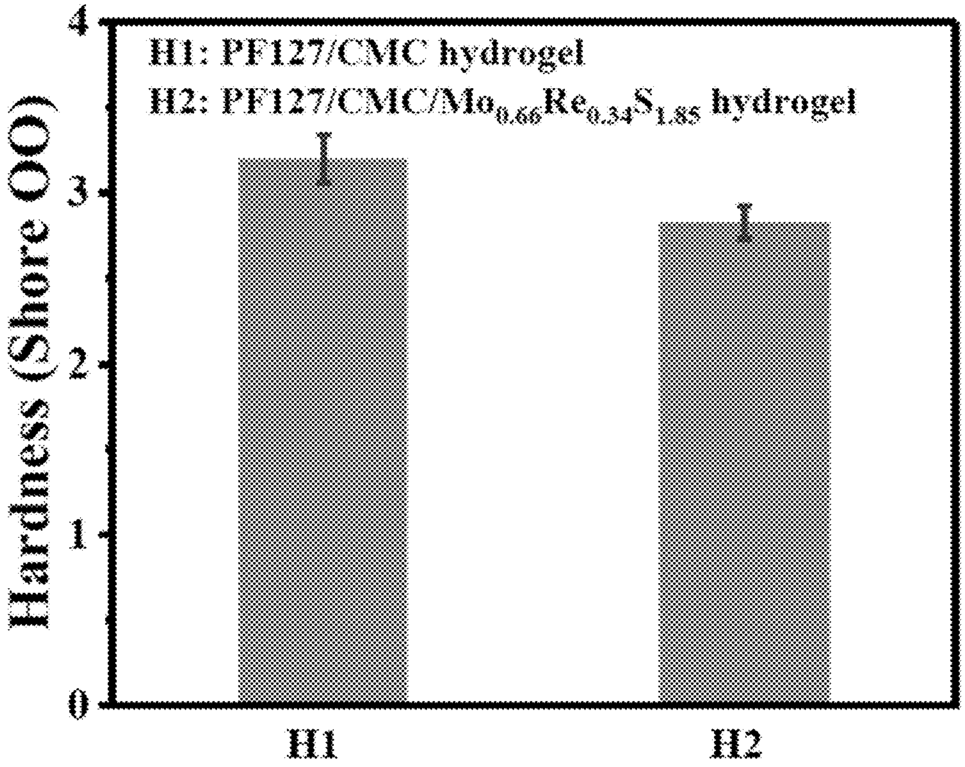
FIG. 21 shows Hardness test results of PF127/CMC and PF127/CMC/$Mo_{0.66}Re_{0.34}S_{1.85}$ hydrogels.

Another key parameter for characterizing the stiffness of a gel network is hardness. This is the force necessary to indent the gel to a given depth, and it is determined by producing an indentation with a probe into the gel at a specified velocity and measuring the force required for indentation. While the gel's modulus strongly influences the measured hardness, it also depends on several other factors, including the sample size and shape, probe dimensions, indentation speed, and depth. In this study, hydrogel samples were fabricated using a B3300 Nano3DPrint printer, operating on a panel maintained at 30° C., to produce cylindrical pillars with 0.5 cm in diameter and 0.5 cm in height. The hardness of the hydrogels was measured using a Digital Shore OO Durometer (HFBTE, USA) mounted on a liftable iron frame, following the ASTM D2240 standard. Shore hardness is one of the most employed methods for characterizing the mechanical properties of soft tissues, including biological materials and hydrogels. As shown in FIG. 21, the Shore OO hardness of both PF127/CMC and PF127/CMC/$Mo_{0.66}Re_{0.34}S_{1.85}$ was approximately 3 Shore OO, with no significant differences observed between the two compositions. These findings indicate that the hydrogels possess an ultrasoft consistency at 30° C., underscoring their potential as promising candidates for wound-healing dressings, according to the literature.

Example 11—Thermogravimetric Analysis (TGA) and DTG Curves

Figure 22:
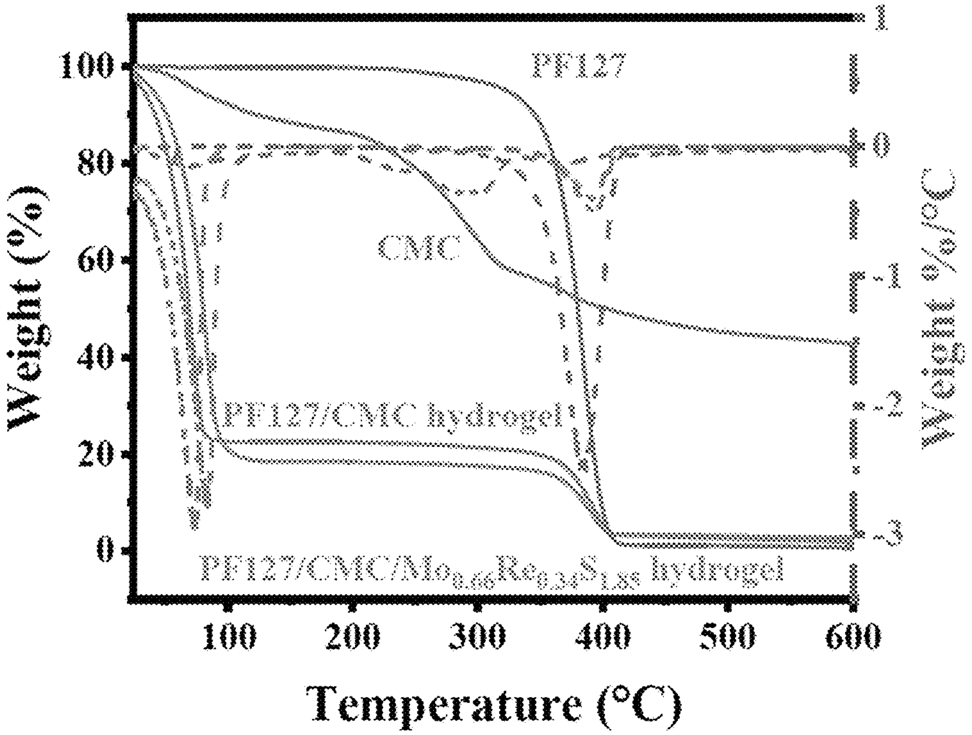
FIG. 22 shows thermogravimetric analysis (TGA), and DTG curves (overlapped) of CMC, PF127, PF127/CMC hydrogel, and PF127/CMC/$Mo_{0.66}Re_{0.34}S_{1.85}$ hydrogel.

The thermal degradation behavior of the PF127, CMC, PF127/CMC hydrogel, and PF127/CMC/$Mo_{0.66}Re_{0.34}S_{1.85}$ hydrogel was analyzed using thermogravimetric analysis (TGA) as shown in FIG. 22. The TGA results indicated that PF127 remained stable below 378° C., beyond which thermal decomposition initiates. A major weight loss occurs around 380° C., reaching approximately 95% by 423° C., with complete degradation at higher temperatures. The TGA curve of CMC, also shown in FIG. 22, reveals two distinct decomposition stages. The initial stage occurs below 150° C. and is attributed primarily to the loss of adsorbed water, while the second decomposition stage begins at 200° C. and continues up to 600° C., predominantly corresponding to the degradation of polysaccharides. The TGA profiles of the PF127/CMC hydrogel and PF127/CMC/$Mo_{0.66}Re_{0.34}S_{1.85}$ hydrogel exhibited an initial weight loss at temperatures below 100° C., primarily attributed to the water removal. The weight percentage decreased to approximately 20%, consistent with the composition of the hydrogels, comprising 17% PF127 and 3% CMC. Furthermore, a significant weight loss was observed around 380° C., corresponding to the thermal degradation of PF127. Given the relatively lower proportion of CMC in the hydrogel formulation, its contribution to the overall weight loss was minimal. Consequently, the weight loss trends of both hydrogels are closely aligned with those of PF127. This observation was further supported by the derivative thermogravimetric (DTG) curves, which show that the maximum decomposition rate of both hydrogels occurs near 380° C., with a slight shift to higher temperatures compared to pure PF127.

Figure 23:
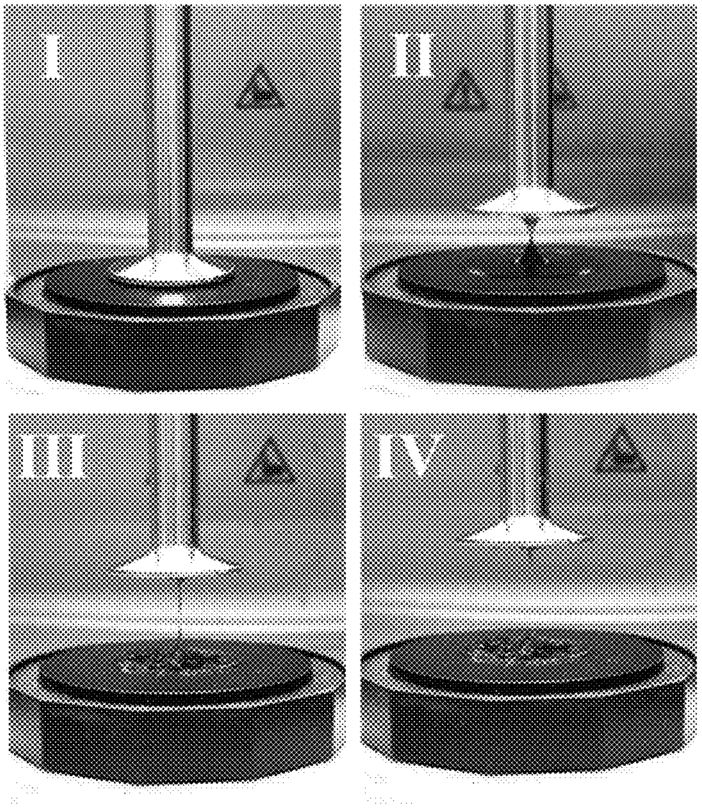
FIG. 23 shows the images of PF127/CMC/$Mo_xRe_{1-x}S_2$ hydrogel samples formed in a gel mold at 30° C. were measured using a parallel plate rheometer. Samples are shown at different heights (I-IV).
Figure 24A:
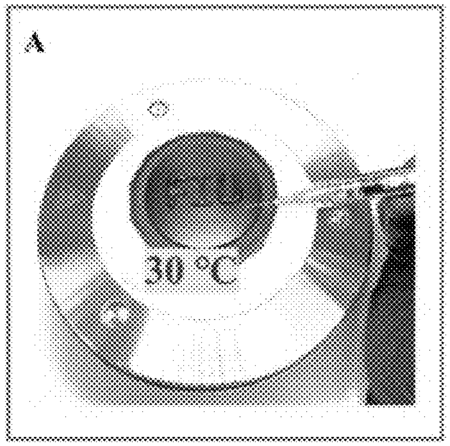
FIGS. 24A-24B show (A) Image of the injectability of PF127/CMC/$Mo_{0.66}Re_{0.34}S_{1.85}$ hydrogel by the needle at 30° C. (B) Images of the contact angle of the PF127/CMC hydrogel and PF127/CMC/$Mo_{0.66}Re_{0.34}S_{1.85}$ hydrogel at 30° C.

In addition, FIG. 23 (sections I to IV) displays images of PF127/CMC/$Mo_xRe_{1-x}S_2$ hydrogel samples during measurement of viscosity using a parallel plate rheometer. The samples, shown at different heights, were prepared at 30° C. FIG. 24A presents an image demonstrating the injectability of PF127/CMC/$Mo_{0.66}Re_{0.34}S_{1.85}$ hydrogel through a needle at 30° C. The "FIU" letters were visible on the same panel. These findings highlight the use of PF127/CMC/$Mo_{0.66}Re_{0.34}S_{1.85}$ hydrogel as injectable hydrogels.

Example 12—Contact Angle

Figure 24B:
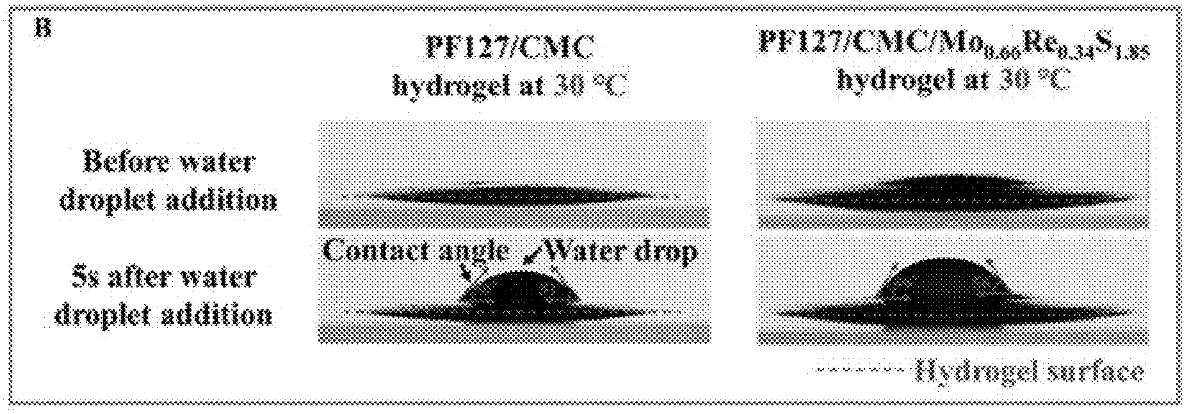
Figure 25:
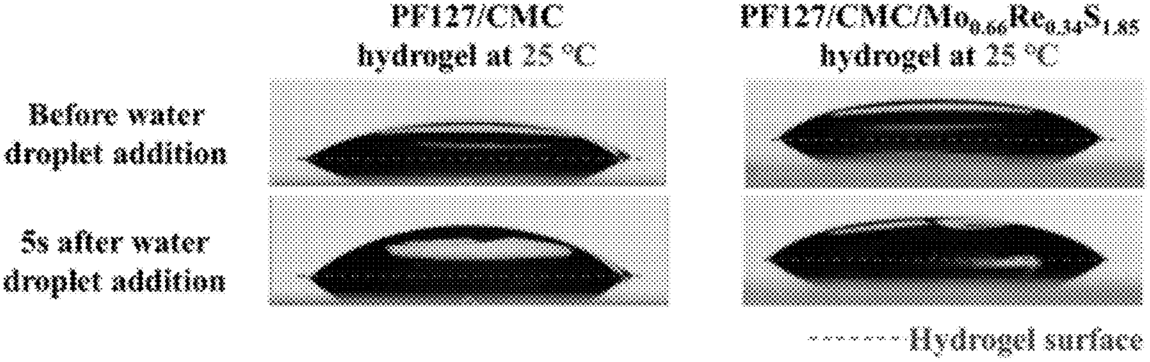
FIG. 25 shows images of the contact angle of the PF127/CMC hydrogel and PF127/CMC/$Mo_{0.66}Re_{0.34}S_{1.85}$ hydrogel at 25° C.

The liquid contact angle (θ) is a critical parameter for evaluating surface wettability, with smaller angles indicating greater water affinity. Super hydrophilic surfaces (θ<10°) enable complete water spreading, hydrophilic surfaces (10°<θ<90°) allow partial spreading, and hydrophobic surfaces (θ>90°) repel water. As illustrated in FIG. 24B, the hydrogel undergoes a phase transition from a liquid state to a gel state at 30° C., resulting in an increased contact angle of approximately 50°. The PF127/CMC/$Mo_{0.66}Re_{0.34}S_{1.85}$ hydrogel exhibits a slightly higher contact angle at 30° C. than the PF127/CMC hydrogel, likely attributable to the insolubility of the nanoparticles in water. These findings indicate that the hydrogel's contact angle increases with temperature, transitioning from super hydrophilic to hydrophilic behavior, aligning with observations reported for thermosensitive injectable hydrogels. FIG. 25 shows the contact angle of the hydrogels at 25° C.; water droplets spread rapidly across the hydrogel surface within 5 s, achieving a contact angle below 10°, which reflects high wettability.

Example 13—Morphology of the Materials

Figure 26A:
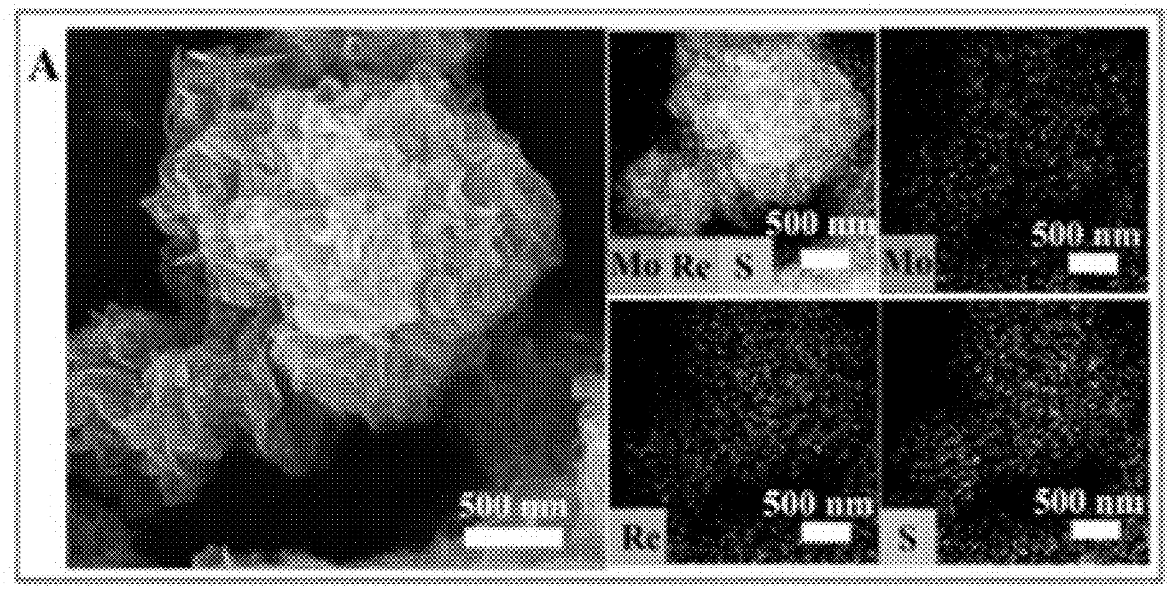
FIGS. 26A-26C show (A) SEM images and elemental mapping analysis of $Mo_{0.66}Re_{0.34}S_{1.85}$ NSs; (B) TEM images and elemental mapping analysis of $Mo_{0.66}Re_{0.34}S_{1.85}$ NSs; (C) SEM images of hydrogel, I: PF127/CMC hydrogel, II: PF127/CMC/$Mo_{0.66}Re_{0.34}S_{1.85}$ hydrogel.
Figure 26B:
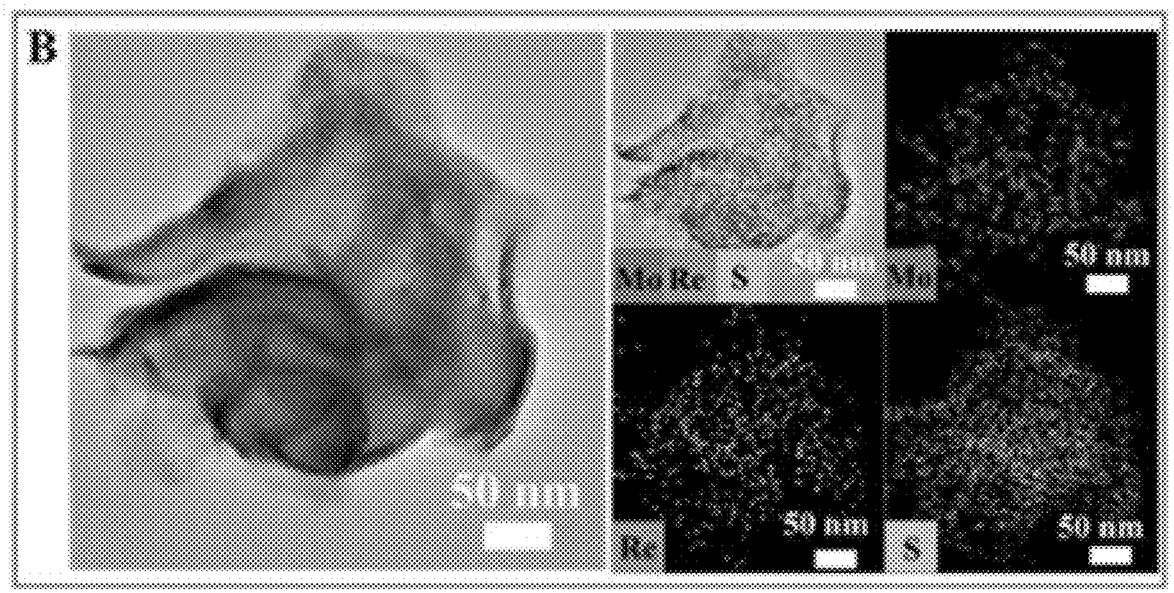
Figure 27A:
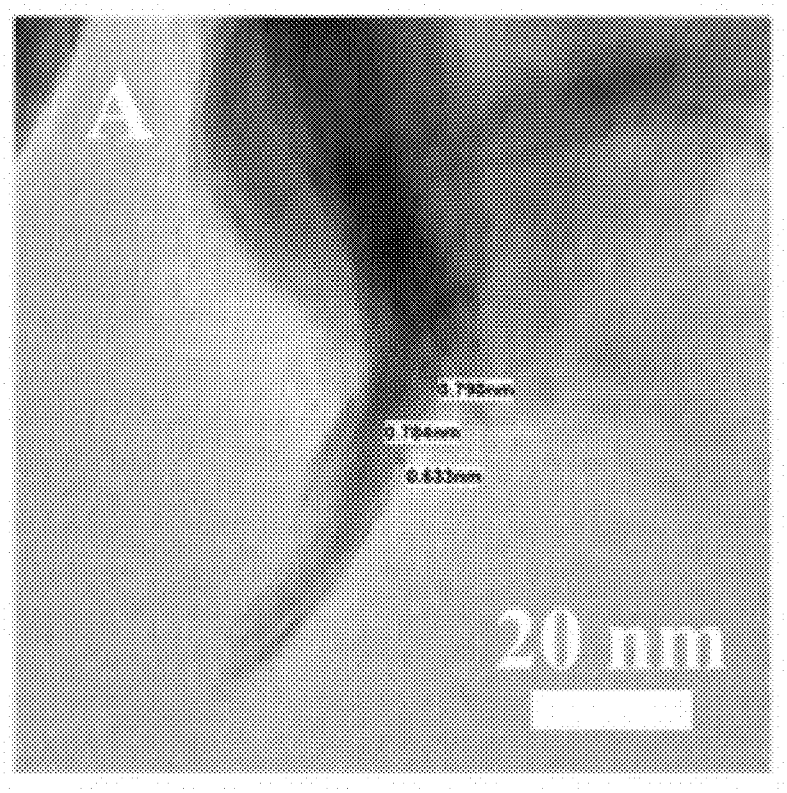
FIGS. 27A-27B show (A) High-resolution TEM (HR-TEM) and (B) SAED pattern of pristine $Mo_{0.66}Re_{0.34}S_{1.85}$ specimen.
Figure 27B:
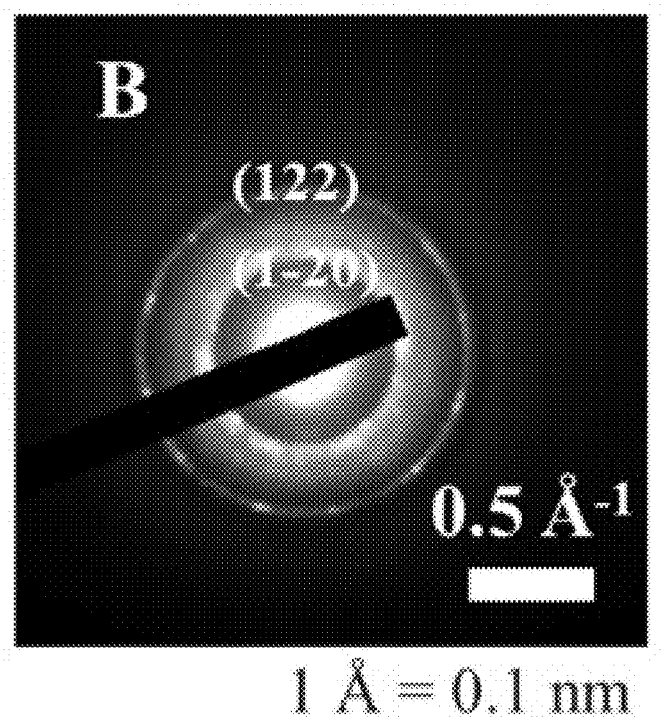

The morphology and composition of $Mo_{0.66}Re_{0.34}S_{1.85}$ nanosheets were characterized by SEM (FIG. 26A) and TEM (FIG. 26B). SEM revealed a flower-like structure of self-assembled nanosheets with a homogeneous distribution of molybdenum (Mo), rhenium (Re), and sulfur(S) elements. TEM/EDS measurements further confirmed the morphology and the uniformity of the elemental distribution. HR-TEM images in FIG. 27 show the lattice fringes with d-spacings of ~0.63 and 0.79 nm, and the SAED pattern showing diffraction rings corresponds to (1-20) and (122) crystal planes, confirming the polycrystalline nature of $Mo_{0.66}Re_{0.34}S_{1.85}$.

Figure 26C:
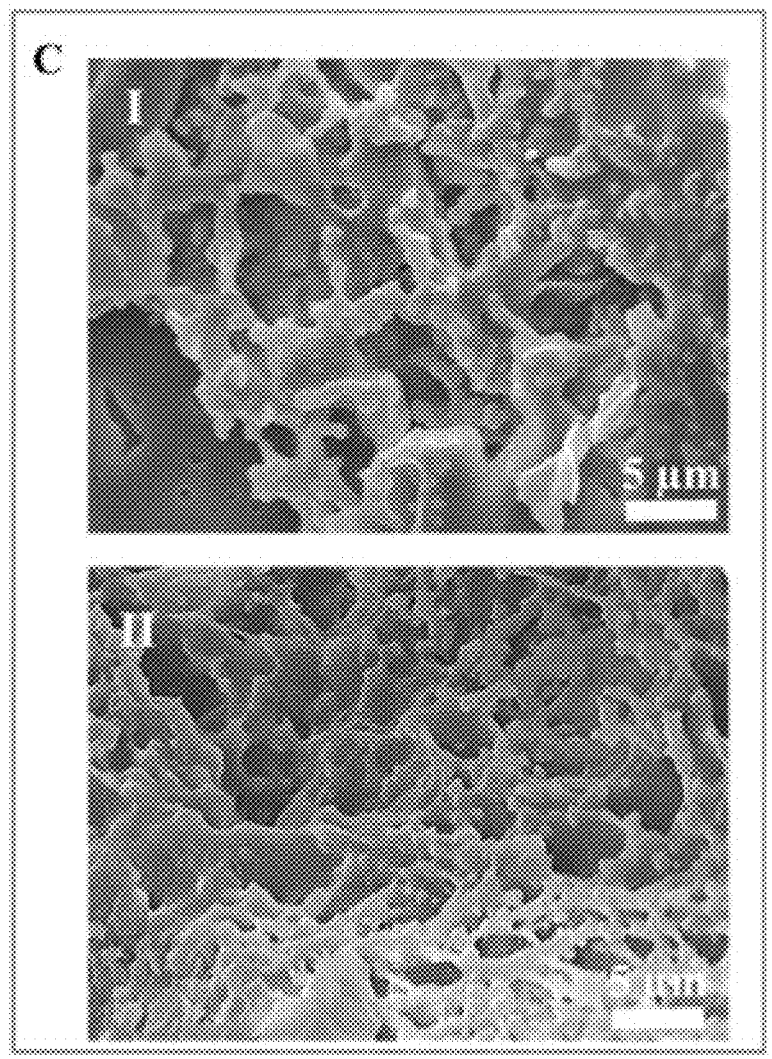

For SEM imaging of the hydrogels, the samples were freeze-dried hydrogels, sectioned into flat slices, and sputter-coated with a 20 nm thick gold layer. FIG. 26C shows that the hydrogels exhibit an interconnected 3D porous microstructure. Image analysis using ImageJ software revealed an average pore size of approximately 2.9 μm for the PF127/CMC hydrogel and 3.3 μm for the PF127/CMC/$Mo_{0.66}Re_{0.34}S_{1.85}$ hydrogel. Notably, the incorporation of $Mo_{0.66}Re_{0.34}S_{1.85}$ nanosheets did not alter the 3D structure of the hydrogel.

Example 14—Photothermal Performance

Figure 28A:
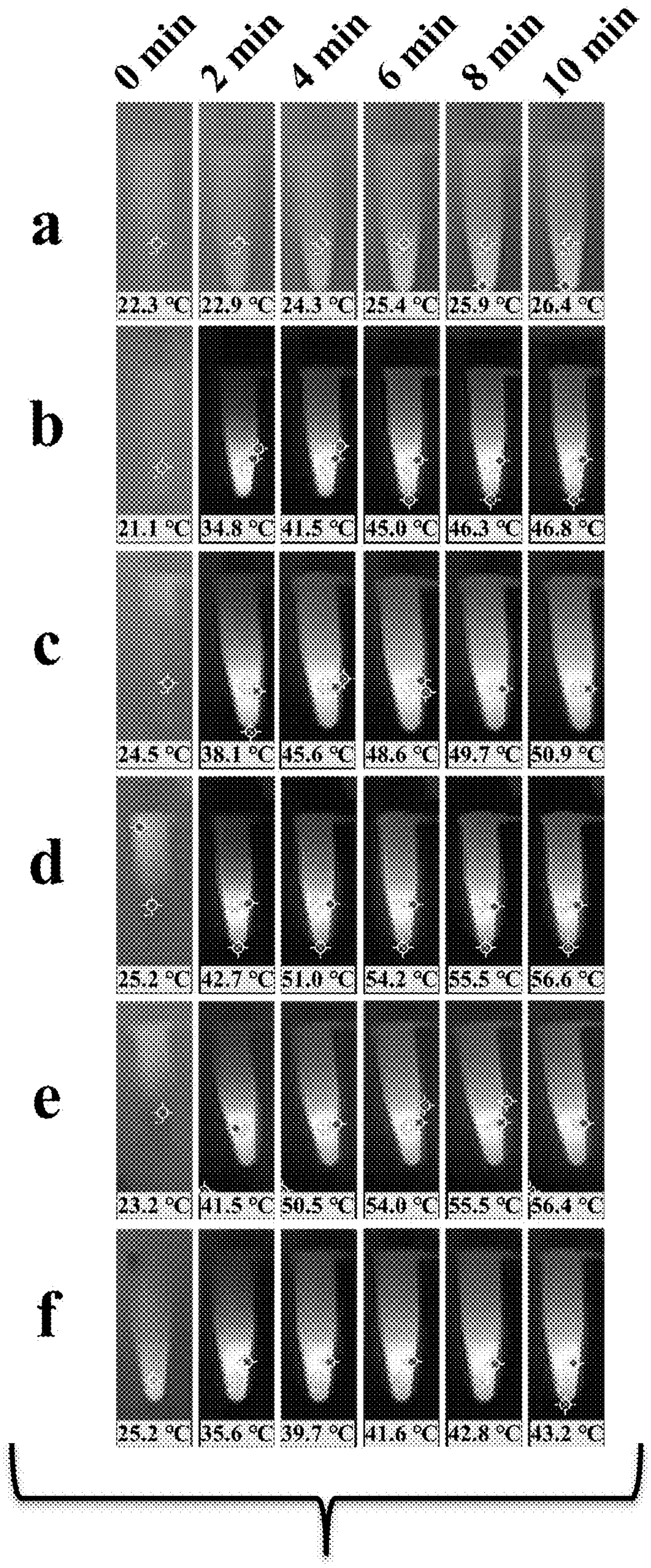
FIGS. 28A-28C show (A) Corresponding thermal images captured of different periods 0-10 min. The dark gray and light gray spots show the maximum temperature and the minimum temperature respectively in the thermal images. a: PF127/CMC hydrogel; b: PF127/CMC/$ReS_2$ hydrogel; c: PF127/CMC/$Mo_{0.42}Re_{0.58}S_{1.94}$ hydrogel; d: PF127/CMC/$Mo_{0.66}Re_{0.34}S_{1.85}$ hydrogel; e: PF127/CMC/$Mo_{0.81}Re_{0.19}S_{1.76}$ hydrogel; f: PF127/CMC/$MoS_2$ hydrogel. (B) The temperature profile of 200 μL PF127/CMC/$Mo_xRe_{1-x}S_2$ hydrogel as a function of time, when irradiated with NIR laser (808 nm, 0.6 W/$cm^2$). (C) Photothermal stability of PF127/CMC/$Mo_{0.66}Re_{0.34}S_{1.85}$ hydrogel for successive 5 cycles of irradiation.
Figure 28B:
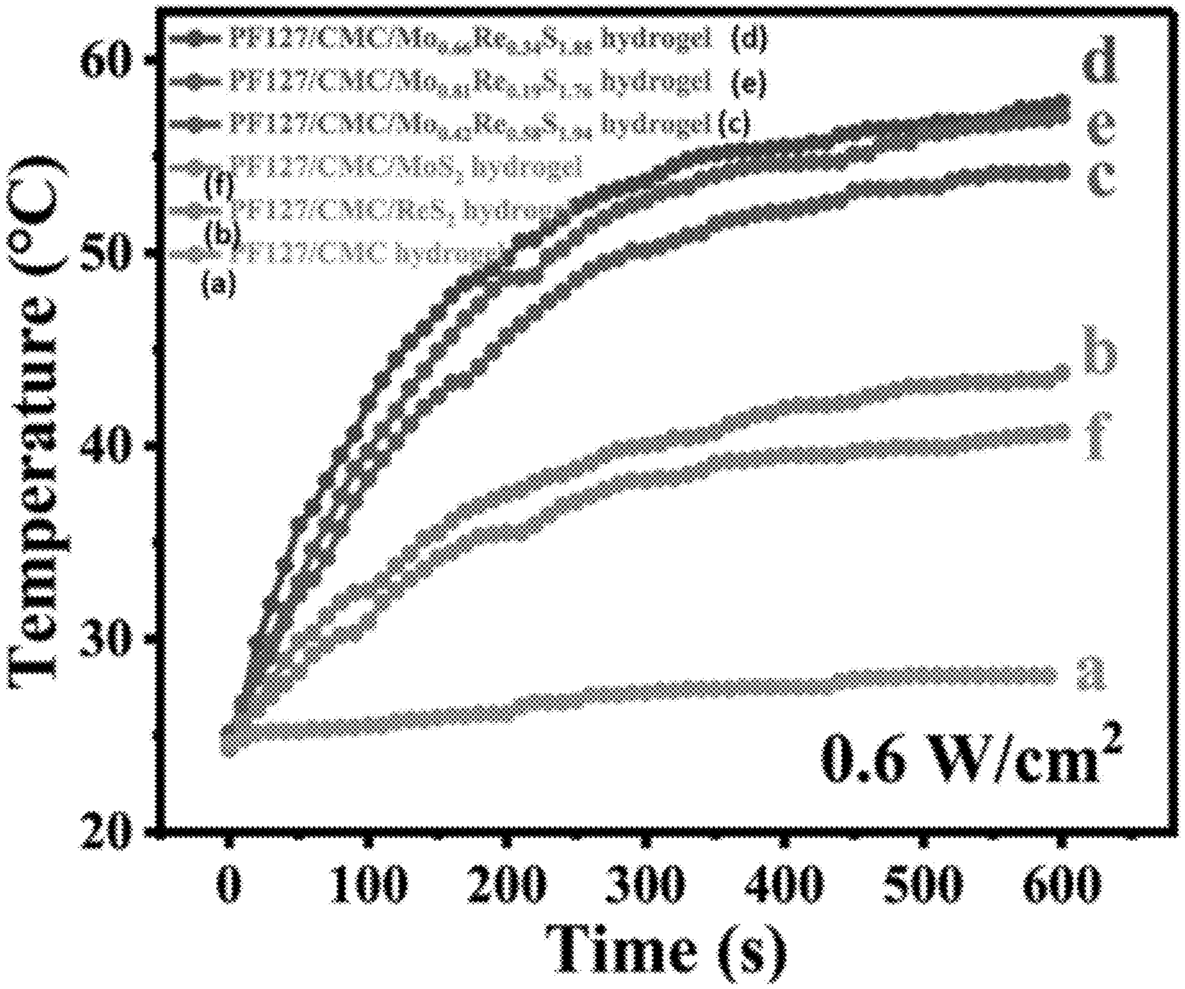

The photothermal conversion capability, the figure of merit in photothermal therapy (PTT), was evaluated for the PF127/CMC/$Mo_xRe_{1-x}S_2$ hydrogels. 200 mg PF127/CMC/$Mo_xRe_{1-x}S_2$ hydrogels were irradiated with an 808 nm near-infrared (NIR) laser at an intensity of 0.6 W/cm$^2$ and a beam diameter of 5 mm, with nanopure water serving as a control. As depicted in FIG. 28B, PF127/CMC/$Mo_xRe_{1-x}S_2$ hydrogels exhibited a rapid temperature increase under NIR irradiation. After 600 s of exposure, the PF127/CMC/$Mo_{0.81}Re_{0.19}S_{1.76}$ and PF127/CMC/$Mo_{0.66}Re_{0.34}S_{1.85}$ hydrogels both achieved the highest temperatures of ~56.6° C. with an increment of 31.4° C., while nanopure water showed a minimal rise of only 4.1° C., attaining a final temperature of 26.4° C. These results are consistent with the thermal images of the hydrogel samples shown in FIG. 28A, as well as with trends previously reported for pure nanosheets. Furthermore, prior experimental data indicate that at a nanosheet concentration of 200 μg/mL, the cell survival rate of $Mo_{0.66}Re_{0.34}S_{1.85}$ nanosheets is 20% higher than that of $Mo_{0.81}Re_{0.19}S_{1.76}$, suggesting that $Mo_{0.66}Re_{0.34}S_{1.85}$ nanosheets, which exhibit relatively lower cytotoxicity, are more suitable for preparing the target hydrogel.

Figure 28C:
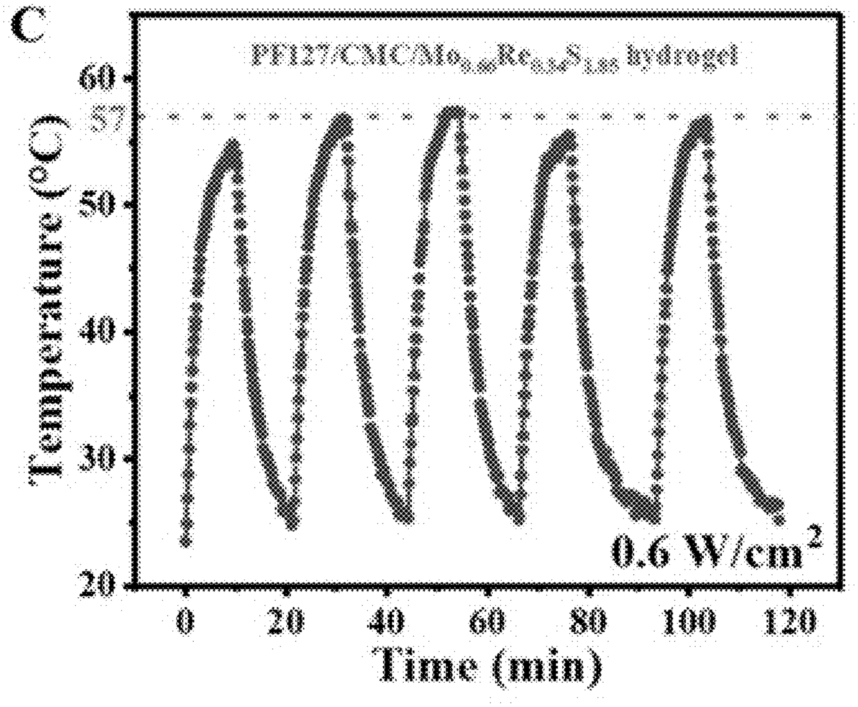

To assess the photothermal stability of the hydrogels, cyclic irradiation was performed, involving five cycles of exposure to the 808 nm NIR laser for 10 min followed by cooling to ambient temperature. The results, shown in FIG. 28C, demonstrate stable photothermal performance with maximum temperatures consistently ranging between 54 and 57° C. across cycles. The photothermal conversion efficiency (η) of the PF127/CMC/$Mo_{0.66}Re_{0.34}S_{1.85}$ hydrogel was determined to be 23.4%, as calculated using Eq. 2, and based on the average of the five cycles.

Example 15—In Vitro Experiments

Figure 29A:
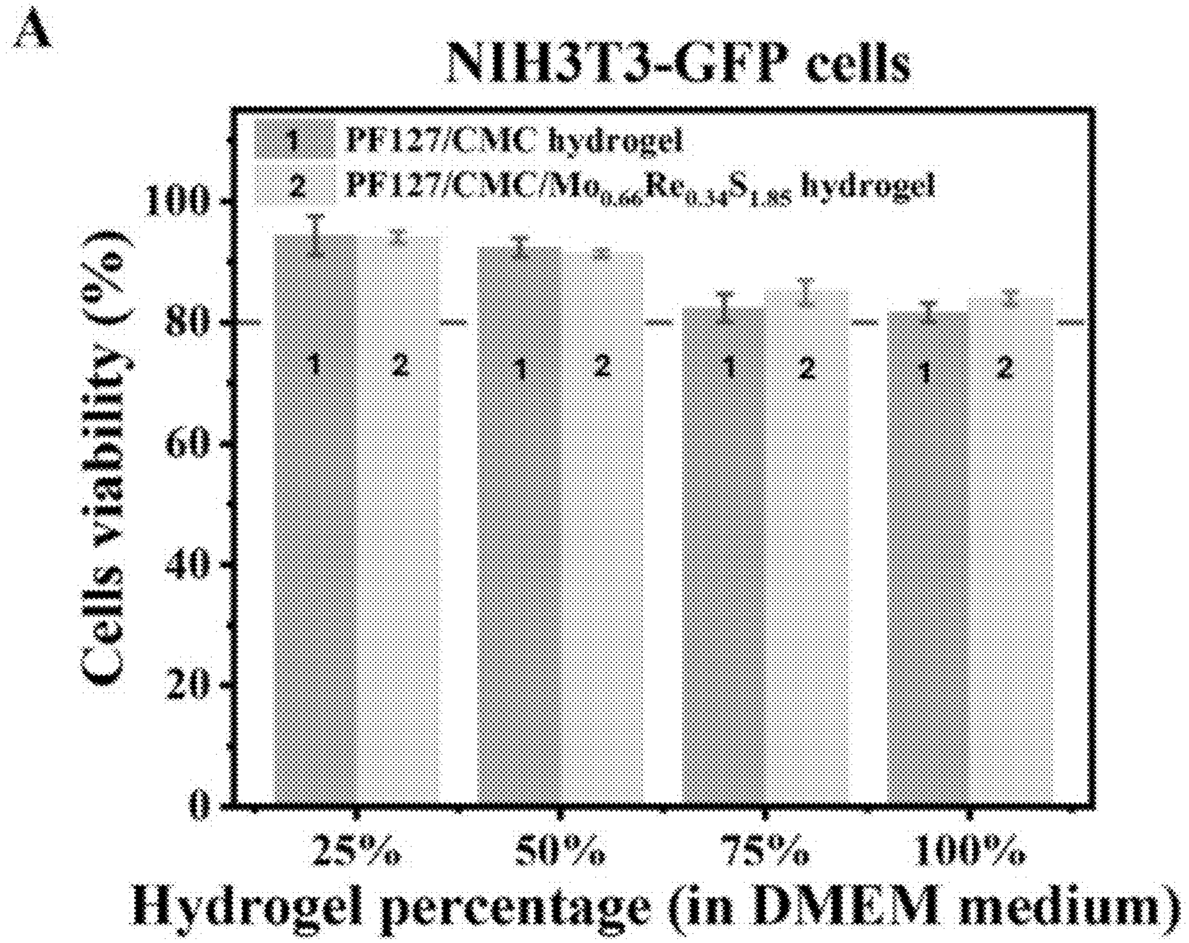
FIGS. 29A-29F show (A) Cell viability experiments in NIH3T3-GFP cell line after treatment with PF127/CMC/$Mo_{0.66}Re_{0.34}S_{1.85}$ hydrogel at different percentages of hydrogel extracts in DMEM (25%, 50%, 75%, and 100%) for 24 h. NIH3T3-GFP cells treated with PBS were used as a control. (B) The relative viability of bacteria after laser irradiation treatments was applied to the LB agar plates. (C) Images of the scratch assay in different hydrogel extract treatments from 24 to 96 h. (n=3). (D) Images of the scratch assay in different hydrogel treatments (n=3). (E) Photographs of the LB agar plates with bacteria following laser irradiation treatments with PF127/CMC hydrogel and PF127/CMC/$Mo_{0.66}Re_{0.34}S_{1.85}$ hydrogel. (F) Fluorescence staining confocal images of bacteria using AO/PI taken after 1 h of irradiation treatments with PF127/CMC hydrogel and PF127/CMC/$Mo_{0.66}Re_{0.34}S_{1.85}$ hydrogel.

Evaluating the biocompatibility of the injectable PF127/CMC/$Mo_{0.66}Re_{0.34}S_{1.85}$ hydrogel is a crucial prerequisite for subsequent in vivo studies. The biocompatibility was evaluated using a CCK-8 assay with NIH 3T3-GFP fibroblast cells, which were incubated with hydrogel extracts at varying proportions in a high-glucose DMEM medium for 24 h. As shown in FIG. 29A, the increasing proportion of the PF127/CMC hydrogel and the PF127/CMC/$Mo_{0.66}Re_{0.34}S_{1.85}$ hydrogel extracts in the DMEM increased from 25% to 100%, resulting in a gradual decline in cell viability, from ~94% to ~81%. Importantly, according to cytotoxicity standards, samples are classified as cytotoxic if cell viability is less than 70%, and as noncytotoxic if cell viability exceeds 70%. These results demonstrated that the cell viability of both hydrogel extracts in DMEM consistently exceeded 70%, indicating good biocompatibility. This favorable interaction with cells suggests that the hydrogel has promising potential for wound healing applications.

The in vitro scratch assay, a wound model for assessing cell migration in vitro, was used as a predictor of wound healing. The 100% extracts of PF127/CMC hydrogel and the PF127/CMC/$Mo_{0.66}Re_{0.34}S_{1.85}$ hydrogel were prepared for the study, with the same cell type employed throughout the experiment. As illustrated in FIG. 29C, all groups demonstrated an improvement in cell migration over 24 to 96 h. The PF127/CMC/$Mo_{0.66}Re_{0.34}S_{1.85}$ hydrogel extracts achieved the highest migration rate, reaching 86%. This finding indicates that the hydrogel can effectively support and accelerate the physiological wound-healing process.

Example 16—Application in Bacterial Killing

The bactericidal activity of the PF127/CMC/$Mo_{0.66}Re_{0.34}S_{1.85}$ hydrogel was evaluated against *S. aureus* and *E. coli* using a spread plate assay. As depicted in FIG. 29E, in the absence of near-infrared (NIR) irradiation, none of the treatment groups, including the PF127/CMC/$Mo_{0.66}Re_{0.34}S_{1.85}$ hydrogel control groups treated with PBS, exhibited significant bactericidal effects against either bacterial strain. However, following NIR irradiation, PF127/CMC/$Mo_{0.66}Re_{0.34}S_{1.85}$ hydrogel groups demonstrated pronounced bactericidal activity against both *S. aureus* and *E. coli* compared with the negative control groups and PF127/CMC hydrogel groups (FIG. 29E). This effect is attributed to the photothermal properties of $Mo_{0.66}Re_{0.34}S_{1.85}$.

Figure 29B:
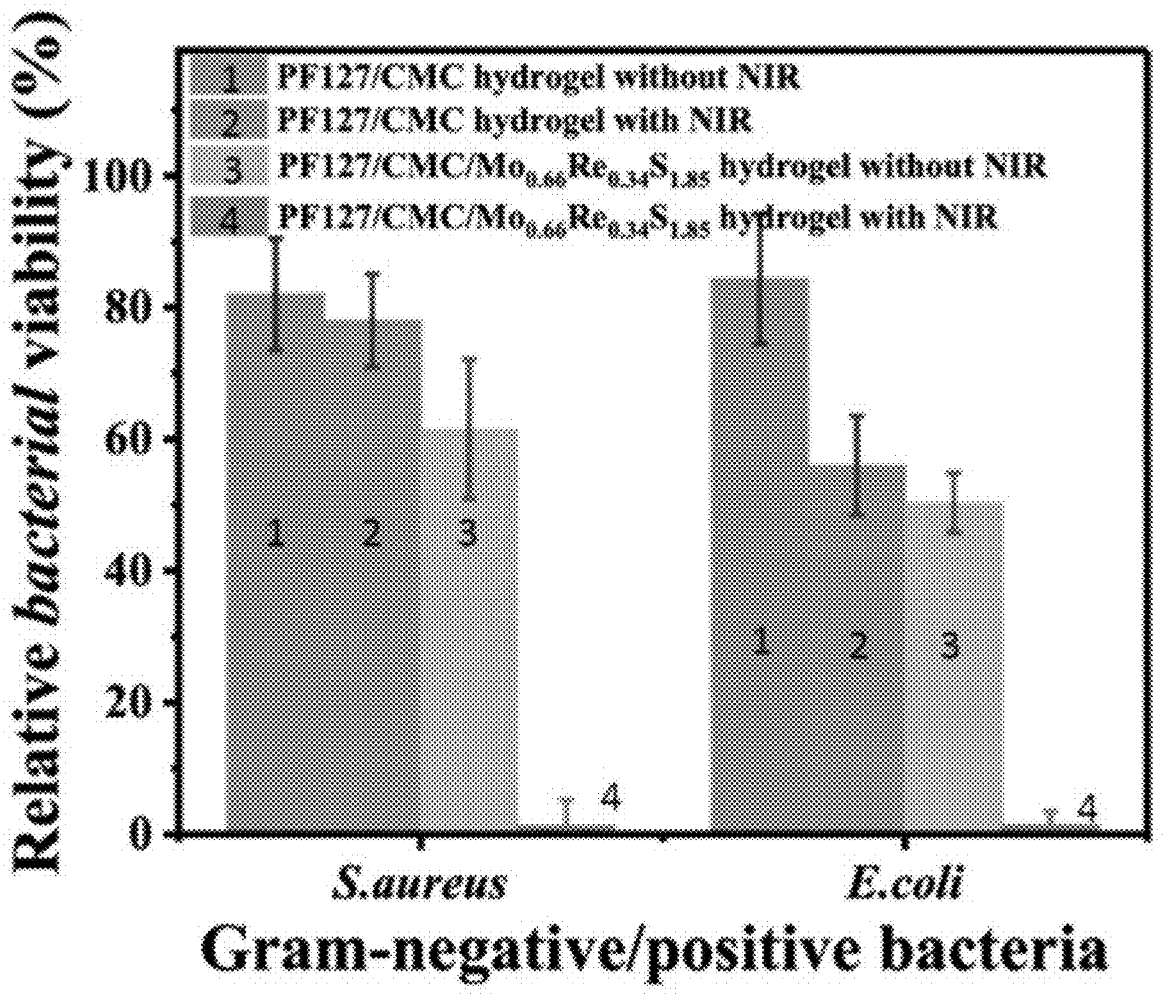
Figure 29C:
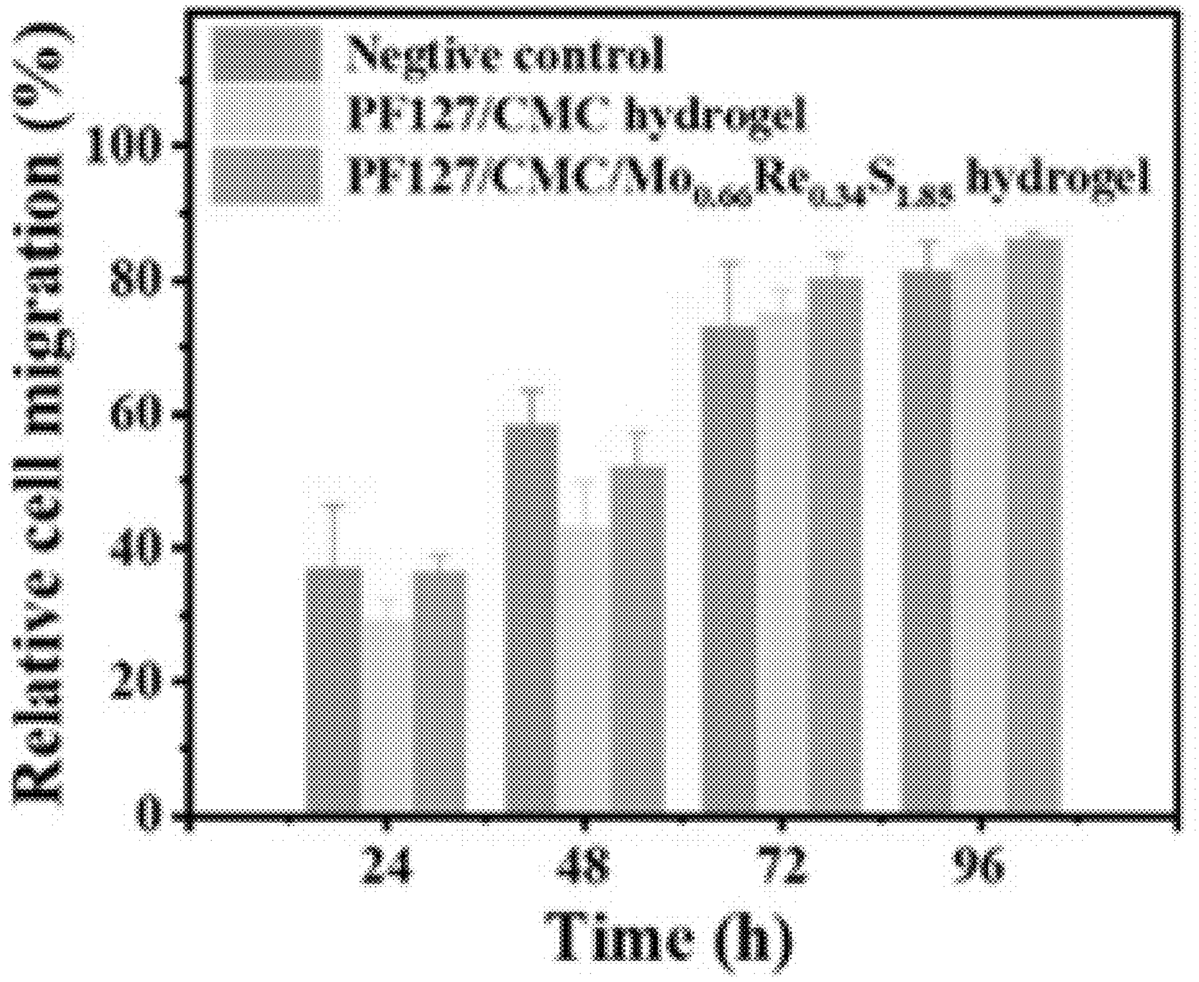
Figure 29D:
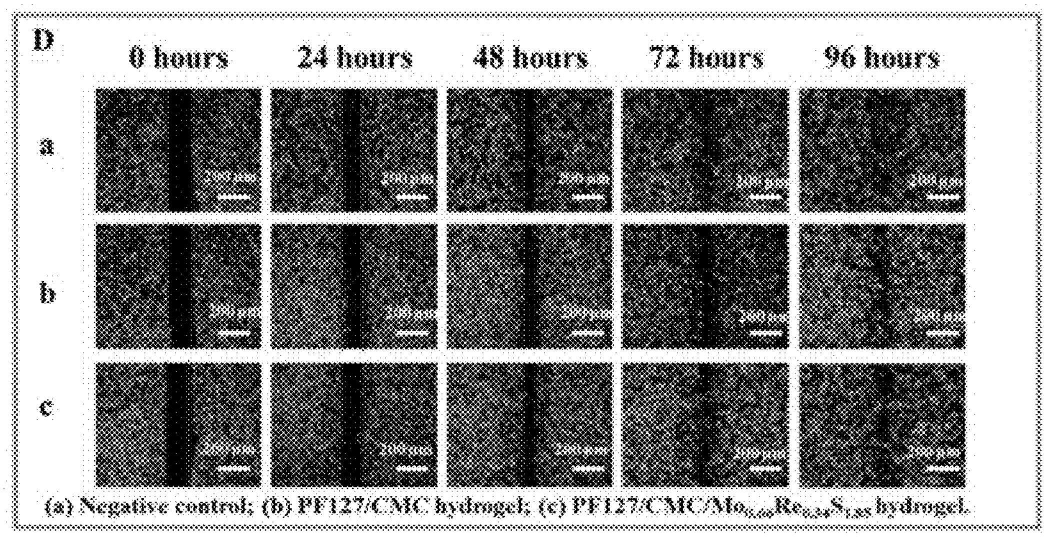
Figure 29E:
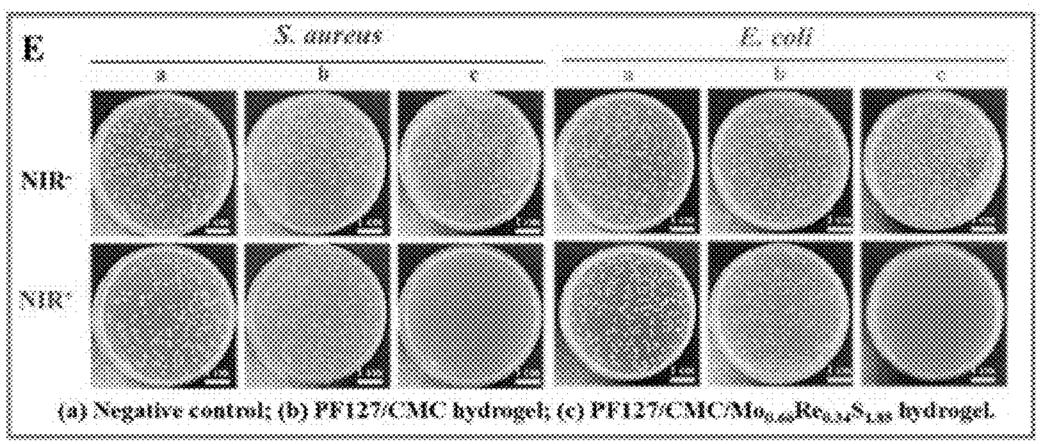

Furthermore, as shown in FIG. 29B, the relative viability of *S. aureus* and *E. coli* in the PF127/CMC hydrogel groups without NIR irradiation was 83% and 85%, respectively. The observed reduction in colony counts should not be directly attributed to the hydrogel's intrinsic antibacterial properties. To prepare samples for plate counting, all hydrogel-bacteria mixtures underwent three cycles of PBS washing and centrifugation to extract the bacterial cells. This procedure may have resulted in bacterial loss due to incomplete detachment from the hydrogel matrix or transfer inefficiencies, potentially leading to an underestimation of viable colonies.

Nevertheless, the comparative analysis of bacterial viability across different treatment conditions provides meaningful insights. Under NIR irradiation, the PF127/CMC hydrogel group showed a moderate reduction in bacterial viability, with *S. aureus* and *E. coli* decreasing to 78% and 56%, respectively. In contrast, the PF127/CMC/$Mo_{0.66}Re_{0.34}S_{1.85}$ hydrogel group without NIR irradiation demonstrated greater antibacterial efficacy, reducing viability to 62% and 50%. Notably, when the PF127/CMC/$Mo_{0.66}Re_{0.34}S_{1.85}$ hydrogel was combined with NIR irradiation, bacterial colonies were nearly undetectable, with viability dropping to approximately 1%, indicating a synergistic photothermal antibacterial effect. These findings highlight the exceptional bactericidal efficacy of the PF127/CMC/$Mo_{0.66}Re_{0.34}S_{1.85}$ hydrogel under NIR laser irradiation.

Figure 29F:
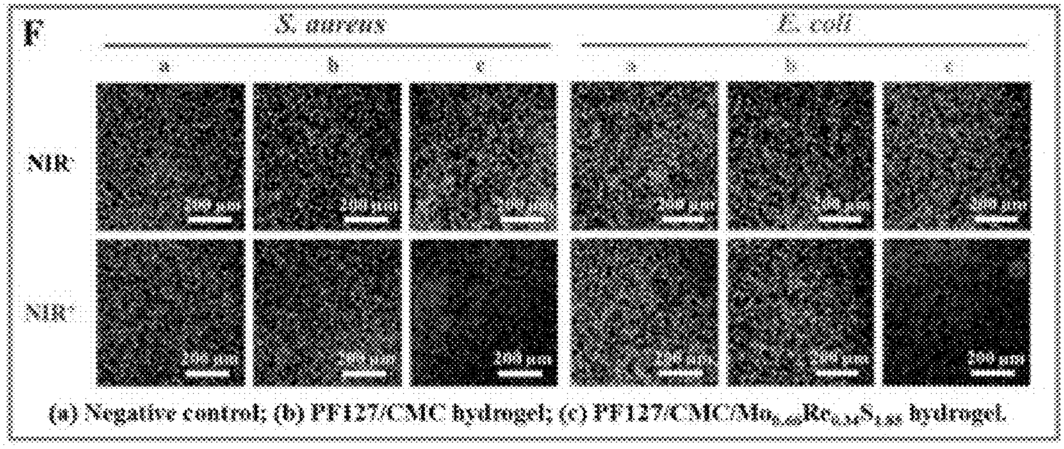

In addition, the bactericidal effect of PF127/CMC/$Mo_{0.66}Re_{0.34}S_{1.85}$ hydrogel was validated by live/dead bacterial staining using acridine orange/propidium iodide (AO/PI), showing that the results were consistent with the spread plate data. As shown in FIG. 29F, intense green fluorescence, indicative of live bacteria stained by AO, was observed in all groups except the PF127/CMC/$Mo_{0.66}Re_{0.34}S_{1.85}$ hydrogel groups under NIR laser irradiation. In this latter group, strong red fluorescence signals from PI-stained dead bacteria were predominant, confirming the hydrogel's photothermally mediated bactericidal activity under NIR irradiation.

Figure 30A:
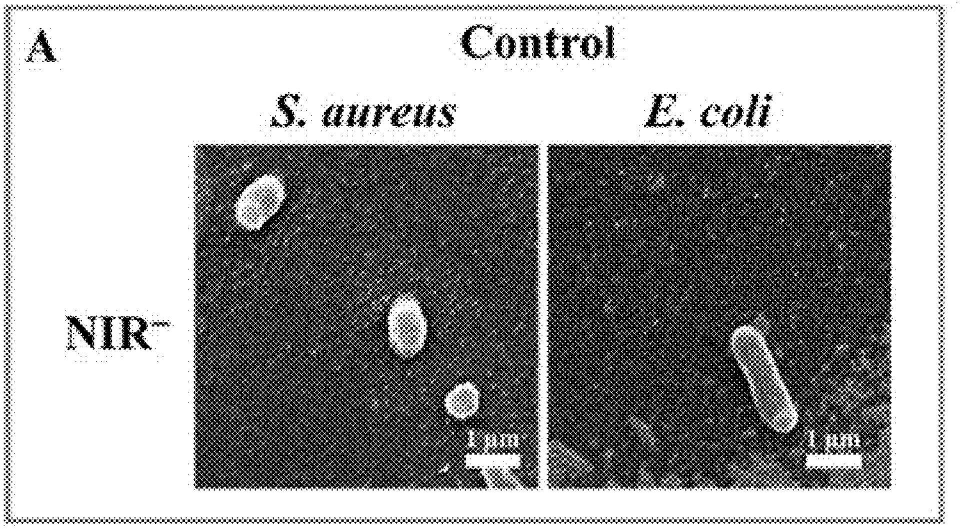
FIGS. 30A-30B show SEM images of *S. aureus* and *E. coli* after different treatments. A: *S. aureus/E. coli* control without the laser irradiation; B: *S. aureus/E. coli* treated with PF127/CMC/$Mo_{0.66}Re_{0.34}S_{1.85}$ hydrogel under 10 min laser irradiation, respectively.
Figure 30B:
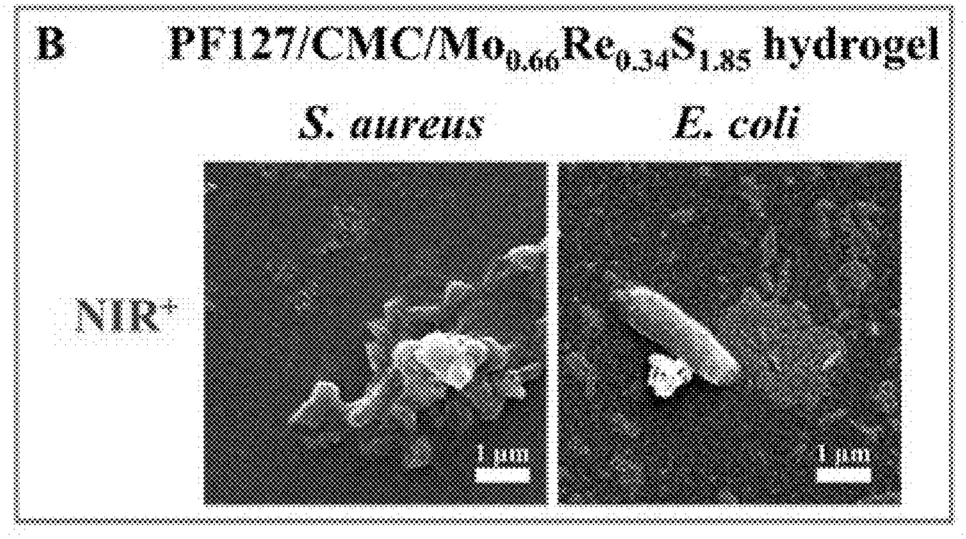

To further elucidate the interaction between the hybrid PF127/CMC/$Mo_{0.66}Re_{0.34}S_{1.85}$ hydrogel and bacteria, the morphology changes of bacterial cells were analyzed by SEM. As illustrated in FIG. 30, the antibacterial effects of PF127/CMC/$Mo_{0.66}Re_{0.34}S_{1.85}$ hydrogel under NIR laser irradiation were attributed to substantial surface collapse of bacterial cells. Following 10 min of NIR irradiation, the bacterial skeleton structures exhibited significant deformation or complete collapse. In contrast, the negative control group, consisting of untreated bacteria, displayed intact bacterial surfaces with preserved skeletal structures. These observations confirm that the photothermal effect of the PF127/CMC/$Mo_{0.66}Re_{0.34}S_{1.85}$ hydrogel is a critical mechanism in the bacteria-killing process. This property underscores the hydrogel's potential as an effective antibacterial agent for wound treatment, significantly reducing the risk of wound infections.

Figure 31:
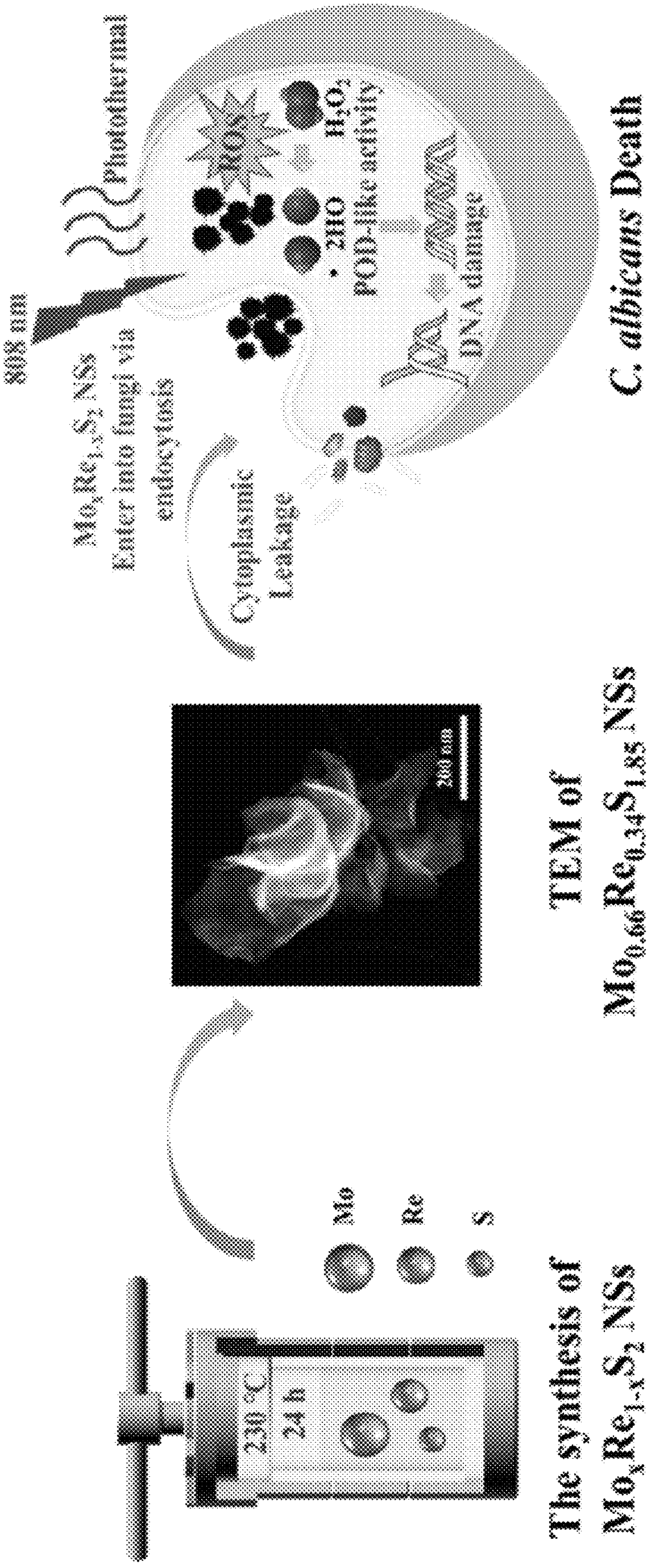
FIG. 31 shows the synthesis of $Mo_xRe_{1-x}S_2$ NSs, the TEM image of $Mo_{0.66}Re_{0.34}S_{1.85}$ NSs, and the mechanism by which $Mo_xRe_{1-x}S_2$ NSs induce the death of *C. albicans.*

As illustrated in the above embodiments and examples, as well as FIG. 31, the subject invention provides synthetic pathways for generating novel nanomaterials exhibiting biological activity. Specifically, mixed-metal chalcogenides having the formula of $Mo_xRe_{1-x}S_y$ were synthesized via a hydrothermal method. This synthesis resulted in flower-like nanostructures comprising nanosheets with uniform elemental distribution, and retained characteristic features of $MoS_2$ and $ReS_2$ two-dimensional transition metal dichalcogenides (2D TMDCs). Characterization of the resulting $Mo_xRe_{1-x}S_y$ NSs revealed particle sizes ranging from about 80 nm to about 300 nm.

The $Mo_xRe_{1-x}S_y$ NSs exhibit peroxidase-like activity, qualifying them as nanozymes. Specifically, $Mo_xRe_{1-x}S_2$ compositions including $Mo_{0.66}Re_{0.34}S_{1.85}$ and $Mo_{0.81}Re_{0.19}S_{1.76}$ demonstrated peroxidase-mimicking behavior and exhibited antifungal activity against *C. albicans* in the presence of $H_2O_2$. Furthermore, enhanced antifungal effects were observed under NIR laser irradiation, indicative of a synergistic photothermal-catalytic mechanism. These results suggest that $Mo_xRe_{1-x}S_2$ nanozymes, particularly those with the aforementioned compositions including $Mo_{0.66}Re_{0.34}S_{1.85}$ and $Mo_{0.81}Re_{0.19}S_{1.76}$, may be utilized as antimicrobial agents or fungicides in therapeutic applications.

Figure 32:
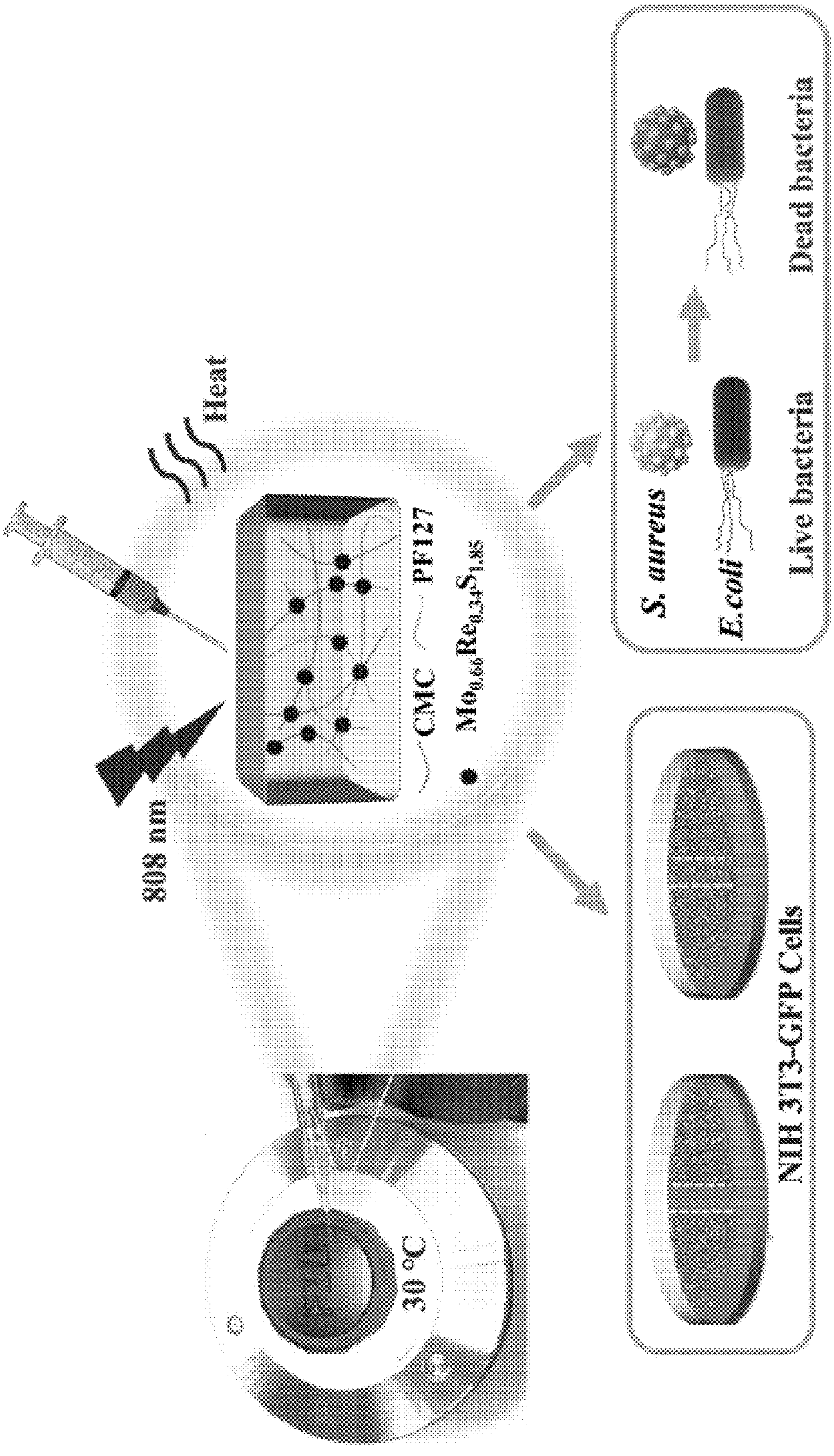
FIG. 32 shows the photothermal performance test, the injectability assessment, the in vitro wound scratch assay, and the in vitro bacterial-killing effect assay performed on the PF127/CMC/$Mo_{0.66}Re_{0.34}S_{1.85}$ hydrogel.

The subject invention further provides a nanocomposite hydrogel composition comprising PF127, CMC, and $Mo_{0.66}Re_{0.34}S_{1.85}$ NSs (also referred to as PF127/CMC/$Mo_{0.66}Re_{0.34}S_{1.85}$). The hydrogel composition integrates the structural and moisture-retention benefits of conventional wound dressings with additional functionalities imparted by the 2D nanomaterials, such as light-responsive behavior and antimicrobial activity. As shown in FIG. 32, the PF127/CMC/$Mo_{0.66}Re_{0.34}S_{1.85}$ hydrogel composition exhibits a photothermal conversion efficiency of approximately 23.4% under NIR laser irradiation (808 nm, 10 min). Rheological testing showed a pronounced increase in storage modulus (G') at 35° C., with sol-gel transition occurring at approximately 27.8° C. The hydrogel composition exhibits shear-thinning behavior, thereby enabling injectability and suitability for in situ application.

Biocompatibility assessments demonstrated cell viabilities exceeding 80% across a range of extract concentrations. In a wound healing assay, the hydrogel composition supported a cell migration rate of approximately 86% after 96 hours, indicating utility in promoting tissue regeneration. In vitro antibacterial assays confirmed effective bactericidal activity against *S. aureus* and *E. coli*, with complete bacterial eradication observed under NIR irradiation. This effect is believed to result from localized photothermal heating that increases bacterial membrane permeability.

In certain embodiments, the hydrogel composition may be optimized for enhanced responsiveness to external stimuli, such as pH, temperature, or light, thereby enabling smart, on-demand therapeutic release. In some embodiments, natural or bio-derived polymers, such as plant-based polysaccharides or peptide-based materials, may be incorporated to improve biodegradability and environmental sustainability. Accordingly, the subject invention provides a versatile platform for the development of advanced wound care materials, as well as broader biomedical applications involving stimuli-responsive and eco-friendly hydrogel systems.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

What is claimed is:

1. A hydrogel formulation comprising: (i) a mixed-metal chalcogenide having a general formula of $M_xM'_{1-x}X_y$, wherein M and M' are distinct transition metal elements, and X is a chalcogen element; and wherein $0 \leq x \leq 1$ and $1.5 \leq y \leq 2.5$; (ii) a thermo-responsive polymer; and (iii) a matrix polymer.

2. The hydrogel formulation of claim 1, the mixed-metal chalcogenide being selected from the group consisting of $Mo_{0.25}Re_{0.75}S_2$, $Mo_{0.5}Re_{0.5}S_2$, $Mo_{0.75}Re_{0.25}S_2$, $Mo_{0.42}Re_{0.58}S_{1.94}$, $Mo_{0.66}Re_{0.34}S_{1.85}$, and $Mo_{0.81}Re_{0.19}S_{1.76}$.

3. The hydrogel formulation of claim 1, the thermo-responsive polymer being selected from the poloxamer family of block copolymers M and M' being each independently selected from the group consisting of Mo, W, Re, Nb, Ta, V, Ti, Zr, and Hf, and X being selected from the group consisting of O, S, Se, and Te.

4. The hydrogel formulation of claim 1, the matrix polymer being selected from saccharide biopolymers.

5. The hydrogel formulation of claim 1, the matrix polymer being engineered to incorporate one or more functional additives selected from the group consisting of pharmaceutical agents, imaging agents, aesthetic or preservation agents, bioactive compounds, protective or stabilizing agents, genetic materials, and functional fillers.

6. A composition comprising the hydrogel formulation of claim 1.

7. A method of treating an infection in a subject, the method comprising administering to the subject, an effective amount of the composition of claim 6.

8. The method of claim 7, the infection being caused by microbial pathogens selected from the group consisting of fungal pathogens, and bacterial pathogens.

9. The method of claim 7, further comprising, before, after, or simultaneously with the administering step, treating the subject with one or more ROS-generating agents and/or exposing the subject to NIR irradiation.

10. A method of managing a wound in a subject, comprising administering to the wound, an effective amount of the composition of claim 6.

11. The method of claim 10, comprising injecting the composition into or onto the wound.

12. The method of claim 10, further comprising, before, after, or simultaneously with the administering step, treating the wound with one or more ROS-generating agents and/or exposing the wound to NIR irradiation.

13. A method of protecting a wound from an infection, the method comprising applying an injectable composition according to claim 6, into or onto the wound.

* * * * *